US006653126B1

(12) United States Patent
Steller et al.

(10) Patent No.: US 6,653,126 B1
(45) Date of Patent: Nov. 25, 2003

(54) COMPOSITIONS AND METHODS FOR THE SCREENING OF COMPOUNDS TO ENHANCE OR REDUCE APOPTOSIS

(75) Inventors: Hermann Steller, Sherborn, MA (US); Kim McCall, Chestnut Hill, MA (US); Lakshmi Goyal, Belmont, MA (US); Julie Agapite, Cambridge, MA (US)

(73) Assignee: Massachusetts Insititute of Technology, Cambridge, MA (US)

( * ) Notice: Subject to any disclaimer, the term of this patent is extended or adjusted under 35 U.S.C. 154(b) by 0 days.

(21) Appl. No.: 09/586,305

(22) Filed: Jun. 2, 2000

Related U.S. Application Data

(60) Provisional application No. 60/137,624, filed on Jun. 4, 1999.

(51) Int. Cl.[7] ........................ C12N 15/00; C12N 15/09; C12N 15/63; C12N 15/70; C12N 15/74

(52) U.S. Cl. .................................... 435/320.1; 536/23.1

(58) Field of Search .......................... 536/23.1; 514/44; 435/320.1

(56) References Cited

U.S. PATENT DOCUMENTS

| | | | |
|---|---|---|---|
| 4,241,050 | A | 12/1980 | Barth |
| 4,675,285 | A | 6/1987 | Clark et al. |
| 4,683,195 | A | 7/1987 | Mullis et al. |
| 4,728,591 | A | 3/1988 | Clark et al. |
| 4,774,339 | A | 9/1988 | Haugland et al. |
| 4,802,951 | A | 2/1989 | Clark et al. |
| 5,069,769 | A | 12/1991 | Fujimiya et al. |
| 5,137,609 | A | 8/1992 | Manian et al. |
| 5,187,288 | A | 2/1993 | Kang et al. |
| 5,190,632 | A | 3/1993 | Fujimiya et al. |
| 5,215,927 | A | 6/1993 | Berenson et al. |
| 5,248,782 | A | 9/1993 | Haugland et al. |
| 5,274,113 | A | 12/1993 | Kang et al. |
| 5,434,272 | A | 7/1995 | Corrie et al. |
| 5,451,663 | A | 9/1995 | Kang et al. |
| 5,614,386 | A | 3/1997 | Metzker et al. |
| 5,622,829 | A | 4/1997 | King et al. |
| 5,693,473 | A | 12/1997 | Shattuck-Eidens et al. |
| 5,709,998 | A | 1/1998 | Kinzler et al. |
| 5,760,207 | A | 6/1998 | Kinzler et al. |
| 5,861,494 | A | 1/1999 | Soppet et al. |
| 5,879,890 | A | 3/1999 | Laken et al. |

FOREIGN PATENT DOCUMENTS

| | | |
|---|---|---|
| EP | 0234799 A2 | 9/1987 |
| WO | WO 90/05785 | 5/1990 |

OTHER PUBLICATIONS

Abrams et al., "Programmed cell death during Drosophila embryogenesis," *Developement* 117:29–43, 1993.

Ambrosini et al., "A novel anti–apoptosis gene, survivin, expressed in cancer and lymphoma," *Nat. Med.* 3:917–921, 1997.

Birnbaum et al., "An apoptosis–inhibiting gene from nuclear polyhedrosis virus encoding a polypeptide with Cys/His sequence motifs," *J. Virol.* 68:2521–2528, 1994.

Brand and Perrimon, "Targeting gene expression as a means of altering cell fates and generating dominant phenotypes," *Development* 118:401–415, 1993.

Bumb et al., "Inhibition of ICE family proteases by baculovirus antiapoptotic protein p35," *Science* 269:1885–1888, 1995.

Chang et al., "phyllopod functions in the fate determination of a subset of photoreceptor death in rd, rds and rhodopsin mutant mice," *Cell* 80:463–472, 1995.

Chen et al., "grim, a novel cell death gene in Drosophila," *Genes Dev.* 10:1773–1782, 1996.

Chu et al., "Suppression of tumor necrosis factor–induced cell death by inhibitor of apoptosis c–IAP2 is under NF–kappaB control," *Proc. Nat. Acad. Sci.* U.S.A. 94:10057–62, 1997.

Clem and Miller, "Control of programmed cell death by the baculovirus genes p35 and iap," *Mol. Cell. Biol.* 14:5212–5222, 1994).

Cooley et al., "Insertional mutagenesis of the Drosophila genome with single P elements," *Science* 239:1121–1128, 1988.

Crook et al., "An apoptosis–inhibiting baculovirus gene with a zinc finger–like motif," *J. Virol.* 67:2168–2174, 1994.

Davidson and Steller, "Blocking Apoptosis Prevents Blindness in Drosophila Retinal Degeneration Mutants," Nature 33/91:587–591, 1998.

Devereaux et al., "X–linked IAP is a direct inhibitor of cell–death proteases," *Nature* 388:300–304, 1997.

Duckett et al., "A conserved family of cellular genes related to the baculovirus iap gene and encoding apoptosis inhibitors," *EMBO J.* 15:2685–2694, 1996.

Edman et al., "Electric field directed nucleic acid hybridization on microchips," *Nucleic Acids Res* 25:4907–4914, 1997.

Eggers and Ehrlich, "A review of microfabricated devices for gene–based diagnostics," *Hematol Pathol* 9:1–15, 1995.

Engels, "P Elements in Drosophila" http://www.wisc.edu/CATG...ents/Pt.html#PElementsinDrosophila; Modified from a chapter in Transposable Elements, edited by H. Saedler and A. Gierl. Springer–Verlag, Berlin, pp. 103–123. 1996.

(List continued on next page.)

*Primary Examiner*—James Ketter
*Assistant Examiner*—Konstantina Katcheves
(74) *Attorney, Agent, or Firm*—Medlen & Carroll, LLP

(57) ABSTRACT

Nucleotide acid sequences and corresponding translated products of novel mutant forms of the Drosophila DIAP1 gene are described. Such sequences and products are useful in screening methods for identifying and testing agonists and antagonists of DIAP1.

3 Claims, 26 Drawing Sheets

OTHER PUBLICATIONS

Golstein et al., "Homology between Reaper and the cell death domains of Fas and TNFR1," *Cell* 81:185–186, 1995.

Grether et al., "The head involution defective gene of *Drosophila melanogaster* functions in programmed cell death," *Genes & Development* 9:1694–1708, 1995.

Hay et al., "Drosophila homologs of baculovirus inhibitor of apoptosis proteins function to block cell death," *Cell* 83:1253–1262, 1995.

Hengartner, "Programmed cell death in invertebrates," *Curr. Opin. Genetics Devel.* 6:34–38, 1996.

Jacobson, M.D., et al., "Programmed Cell Death in Animal Development," *Cell* 88:347–354, 1997.

Kerr et al., "Apoptosis: a basic biological phenomenon with wide ranging implications in tissue kinetics," *Br. J. Cancer* 26:239–257, 1972.

Liston et al., "Suppression of apoptosis in mammalian cells by NAIP and a related family of IAP genes," *Nature* 379:349–353, 1996.

Lockshin, "Programmed cell death. Activation of lysis mechanism by a mechanism involving the synthesis of protein," *J. Insect Physiol. 15:1505–1516*, 1969.

Martinou, et al., "Over–expression of Bcl–2 in transgenic mice protects neurons from naturally occurring cell death and experimental ischemia," *Neuron* 13:1017–1030, 1994.

McNabb et al., "Disruption of a behavioral sequence by targeted death of peptidergic neurons in Drosophila," *Neuron* 19:813–823, 1998.

Morin et al., "Apoptosis and APC in colorectal tumorigenesis,", *Proc. Natl. Acad. Sci.*USA 93:7950–7954, 1996.

Naik et al., "The rise and fall of apoptosis during multistage tumorigenesis: down–modulation contributes to tumor progression from angiogenic progenitors," *Genes Dev.* 10:2105–2116, 1996.

Nordstrom et al., "Activation of the reaper gene defines an essential function required for both naturally–occurring apoptosis and induced cell killing in Drosophila", *Dev. Biol.* 180:227–241, 1996.

Pappalardo et al., "Microdissection, microchip arrays, and molecular analysis of tumor cells (primary and metastases)," *Semin Radiat Oncol* 8:217–223, 1998.

Pronk et al., "Requirement of an ICE–like protease for induction of apoptosis and ceramide generation by REAPER," *Science* 271:808–810, 1996.

Robinow et al., "Genes that induce apoptosis: transcriptional regulation in identified, doomed neurons of the Drosophila CNS," *Dev. Biol.* 190:206–213, 1997.

Roth et al., "The TNFR2–TRAF signaling complex contains two novel proteins related to baculovirus inhibitor of apoptosis proteins," *Cell* 83:1243–1252, 1995.

Roy et al., "The gene for neuronal apoptosis inhibitory protein is partially deleted in individuals with spinal muscular atropy," *Cell* 80:167–178, 1995.

Schmalzing et al., "Immunoassay for thyroxine (T4) in serum using capillary electrophoresis and micromachined devices," *J Chromatogr B Biomed Sci Appl* 697:175–180, 1997.

Sinha et al., "Polymer support oligonucleotide synthesis XVIII[1,2]: use of β–cyanoethyl–N,N–dialkylamino–/N–morpholino phosphoramidite of deoxynucleosides for the synthesis of DNA fragments simplifying deprotection and isolation of the final product," *Nucleic Acids Res.* 12:4539–4557 (1984).

Steller, H., "Mechanisms and Genes of Cellular Suicide," *Science* 267:1445–1446, 1995.

Thompson, "Apoptosis in the Pathogenesis and Treatment of Disease," *Science* 267:1456–1462, 1995.

Truman et al., "Programmed neuronal death in insect development," *J. Neurobiol.*23:1295–1311, 1992.

Uren et al.,"Cloning and expression of apoptosis inhibitory protein homologs that function to inhibit apoptosis and/or bind tumor necrosis factor receptor–associated factors," *Proc. Natl. Acad. Sci* U.S.A. 93:4974–4978, 1996.

Vucic et al., "Inhibition of Reaper–induced apoptosis by interaction with inhibitor of apoptosis proteins (IAPs)," *Proc. Nat. Acad. Sci.*U.S.A. 94:10183–10188, 1997.

Vucic et al., "Inhibitor of apoptosis proteins physically interact with and block apoptosis induced by Drosophila proteins HID and GRIM" *Mol. Cell Biol.*18:3300–3309, 1998.

Xue and Horvitz, "Inhibition of the *Caenorhabditis elegans* cell–death protease CED–3 by a CED–3 cleavage site in baculovirus p35 protein," *Nature* 377:248–251, 1995.

White E. ,"Life, death and the pursuit of apoptosis,", *Genes Dev.* 10:1–15, 1996.

White et al., "Genetic control of cell death in Drosophila," *Science* 264:677–683, 1994.

Zhou et al., "Cooperative functions of the reaper and head involution defective genes in programmed cell death of Drosophila CNS midline cells," *Proc. Nat. Acad. Sci. U.S.A.* 94:5131–5136, 1997.

Albarella, et al., "Monoadduct forming photochemical reagents for labeling nucleic acids for hybridization," *Nucleic Acids Research* 117(11):4293–4308 (1989).

Allen et al., *Gel Electrophoresis and Isoelectric Focusing of Proteins*, Walter de Gruyter, New York 1984, pp. 17–62.

Amit, et al., Photosensitive Protecting Groups of Amino Sugars and Their Use in Glycoside Synthesis. 2–Nitrobenzyloxcarbonylamino and 6–Nitroveratryloxycarbonylamino Derivatives, *J. Org. Chem.* 39(2):192–196 (1974).

*Antibodies: A Laboratory Manual* (E. Harlow and D. Lane, editors, Cold Spring Harbor Laboratory Press), 1988, pp. 53,72–73.

Bain et al., "Site–Specific Incorporation of Nonnatural Residues during In Vitro Protein Biosynthesis with Semisynthetic Aminoacryl–tRNAs," *Biochemistry* 30:5411–21 (1991).

Baldini, et al., "Mischarging *Escherichia coli* $tRNA^{Phe}$ with L–4'–[Trifluoromethyl)–3H–diazirin–3–yl] phenylalaine, a Photoactivatable Analogue of Phenylalanine," *Biochemistry* 27:7951–7959 (1988).

Billington, et al., "Synthesis and Photochemistry of Photolabile N–Glycine Derivatives and Efforts of One on the Glycine Receptor," *Biochemistry* 31:5500–5507 (1992).

Bruce and Uhlenbeck, "Specific Interaction of Anticodon Loop Residues with Yeast Phenylalanyl–tRNA Synthetase," *Biochemistry* 21:3921–3926 (1982).

Callaway and Katz, "Photostimulation using caged glutamate reveals functional circuitry in living brain slices," *PNAS, USA* 90:7661–7665 (1993).

*Chemical Analysis*, Hemmila, "Application of Fluorescence in Immunoassays," p139–158.

Crowley et al., "The signal sequence moves through a ribosomal tunnel into a noncytoplasmic aqueous environment at the ER membrane early in translocation," *Cell* 73:1101–1115 (1993).

*Current Protocols in Molecular Biology* (F.M. Ausubel et al. editors, Wiley Interscience, 1993), pp. 10–16, 10–77.

Czworkowski et al., "Fluroesence Study of the Topology of Messenger RNA Bound to the 30S Ribosomal Subunit of *Escherichia coli,*" *Biochemistry* 30:4821–4830 (1991).

Dawson, et al., "Affinity Isolation of Transcriptionally Active Murine Erythroleukemia Cell DNA Using a Cleavable Biotinylated Nucleotide Analog," *J. Biological Chemistry* 264:12830–12837 (1989).

DiCesare et al., "A High–Sensitivity Electrochemiluminescence–Based Detection System for Automated PCR Product Quantitation," *BioTechniques* 15:152–59 (1993).

Doty, et al., "Strand separation and Specific Recombination in Deoxyribonucleic Acids: Physical Chemical Studies," *Biochemistry* 46:461–476 (1960).

Ellis–Davies and Kaplan, "A New Class of Photolabile Chelators for the Rapid Release of Divalent Cations: Generations of Caged ca and Caged Mg," *J. Org. Chem.* 53:1966–1969 (1988).

Felgner et al., "Lipofection: A highly efficient, lipid–mediated DNA–transfection procedure," *Proc. Natl. Acad. Sci. USA* 84:7413–17 (1987).

Hall, et al., "Mapping Labeled Sites in *Escherichia coli* Ribosomal RNA: Distribution of Methyl Groups and Identification of a Photoaffinity–Labeled RNA Region Putatively at the Peptidyltransferase Center," *Biochemistry* 24:5702–5711 (1985).

Happ et al., "New Approach to the Synthesis of 2'(3')–O–Aminoacyl Oligoribonucleotides," *J. Org. Chem.* 52:5387–91 (1987).

Hardesty et al., "Extension and Folding of Nascent Peptides on Ribosomes." *The Translational Apparatus*, Nierhaus et al. ed: New York and London; Plenum Press. p. 347–358 (1993).

Hardesty et al., "Ribosome function determined by fluorescence," *Biochimie* 74:391–401 (1992).

Heckler et al., "T4 RNA Ligase Mediated Preparation of Novel "Chemically Misacylated" tRNA$^{Phe}$s," *Biochemistry* 23:1468–73 (1984).

Heckler et al., "Preparation of 2'(3')–O–Acyl–pCpA Derivatives as Substrates for T4 RNA Ligase–Mediated "Chemical Aminoacylation"," *Tetrahedron* 40:87–94 (1984).

Herman, et al., "Affinity Chromatography of DNA Labeled with Chemically Cleavable Biotinylated Nucleotide Analogs," *Analytical Biochemistry* 156:48–55 (1986).

Houlihan, et al., "Nitrobenzyl Ester Chemistry for Polymer Processes Involving Chemical Amplification," *Maromolecules* 21:2001–2006 (1988).

Hudson, "Methodological Implications of Simultaneous Solid–Phases Peptide Synthesis. 1. Comparison of Different Coupling Procedures," *J. Org. Chem.* 53:617–624 (1988).

Johnson et al., "Protein Synthesis and Secretion as seen by the Nascent Protein Chain," *The Translational Apparatus*, Nierhaus et al. ed: New York and London; Plenum Press. p. 359–370 (1993).

Kalbag and Roeske, "A Photolabile Protecting Group for Histidine," *J. Am. Chem. Soc.* 97:440–441 (1975).

Karolin et al., "Fluoresence and Absorption Spectroscopic Properties of Dipyrrometheneboron Difluoride (BODIPY) Derivatives in Liquids, Lipid Membranes, and Proteins," *J. Am. Chem. Soc.* 116:7801–7806 (1994).

Karpen, et al., "Gating kinetics of the cyclic–GMP–activated channel of retinal rods: Flash photolysis and voltage–jump studies," *PNAS, USA* 85:1287–1290 (1988).

Köpper and Zehavi, "A convenient synthesis of the branching–point trisaccharide of starch and glycogen," *Carbohydrate Research* 193:296–302 (1989).

Kozak, "Point Mutations Define a Sequence Flanking the AUG Initiator Codon that Modulates Translation by Eukaryotic Ribosomes," *Cell* 44:283–292 (1986).

Krafft, et al., "Photoactivable Fluorophores. 3. Synthesis and Photoactivation of Fluorogenic Difunctionalized Fluoresceins," *J. Am. Chem. Soc.* 110:301–303 (1988).

Krieg et al., "Photocrosslinking of the signal sequence of nascent preprolactin to the 54–kilodalton polypeptide of the signal recognition particle," *Proc. Natl. Acad. Sci. USA* 83:8604–08 (1986).

Laemmli, "Cleavage of Structural Proteins during the Assembly of the Head of Bacteriophage T4," *Nature* 227:680–685 (1970).

Lesnikowski and Jaworska, "Studies on Stereospecific Formation of P–Chiral Internucleotide Linkage. Synthesis of (Rp,Rp)– and (Sp,Sp)–Thymidylyl(3',5') Thymidylyl (3',5') Thymidine DI(o,O–Phosphorothioate) using 2–Nitrobenzyl Group as a New S–Protection," *Tetrahedron Letters* 30(29):3821–3824 (1989).

Ma et al., "In Vitro Protein Engineering Using Synthetic tRNA$^{Ala}$ with Different Anticodons," *Biochemistry* 32:7939–7945 (1993).

Markings and Tsien, "Caged Nitric Oxide, Stable organic Molecules from which Nitric Oxide can be Photoreleased," *J. Biological Chemistry* 269:6282–6285 (1994).

Marmur and Lane, "Strand Separation and Specific Recombination in Deoxyribonucleic acids: Biological Studies," *Biochemistry* 46:453–461 (1960).

McCray et al., "Properties and uses of photoreactive caged compounds," *Annu Rev Biophys Chem* 18:239–270 (1989).

Mendel, et al., "Construction of a Light–Activated Protein by Unnatural Amino Acid Mutagenesis," *J. Am. Chem. Soc.* 113:2758–2760 (1991).

Miknis and Williams, "Total Synthesis of (±)–Aspirochlorine," *J. Am. Chem. Soc.* 115:536–547 (1993).

Molecular Cell Biology, J. Darnell et al., Editors. Scientific American Books, N.Y., N.Y. pp. 119–132 1991.

Morgan, et al., "The selective isolation of novel cDNAs encoded by the regions surrounding the human interleukin 4 and 5 genes," *Nucleic Acids Research* 20(19):5173–5179 (1992).

Mouton, et al., "A Reagent for Covalently Attaching Biotin to Proteins via a Cleavable Connector Arm," *Archives of Biochemistry and Biophysics* 218(1):101–108 (1982).

Muralidharan, et al., ""Caged" phenylephrine: Development and application to probe the mechanism of α–receptor–mediated vasoconstriction," *PNAS, USA* 90:5199–5203 (1993).

Neu and Heppel, "Nucleotide Sequence Analysis of Polyribonucleotides by Means of Periodate Oxidation Followed by Cleavage with an Amine," *J. Biol. Chem.* 239:2927–34 (1964).

Noren et al., "A General Method for Site–Specific Incorporation of Unnatural Amino Acids into Proteins," *Science* 244:182–188 (1989).

Nishikubo, et al., "Study of Photopolymers. XXXIV. Etherification and Esterification Reactions of Polymers with (o, m, or p)–Bromomethylnitrobenzene Using the DBU Method and the Photochemical Properties of the Resulting Polymers," *J. Polymer Science: Part A: Polymer Chemistry* 28:105–117 (1990).

Odom, et al., *Methods in Molecular Biology* "In Vitro Engineering Using Acyl–Derivatized tRNAs," edited by:R. Matin Humana Press Inc., Totowa, NJ 77:93–103.

Odom et al., "Movement of tRNA but Not the Nascent Peptide during Peptide Bond Formation on Ribosomes," *Biochemistry* 29:10734–10744 (1990).

Oesterhelt et. al., "Bacteriorhodopsin: a biological material for information processing," *Quart. Rev. Biophys.* 4:425–78 (1991).

Ohtsuka, et al., "Studies on Transfer Ribonucleic Acids and Related Compounds. 20. A New Versatile Ribooligonucleotide Block with 2'–(o–Nitrobenzyl) and 3'–Phosphorodianilidate Groups Suitable for Elongation of Chains in the 3' and 5' Directions," *J. Am. Chem. Soc.* 100(14):4580–4584 (1978).

Ohtsuka, et al., "Studies on Transfer Ribonucleic Acids and Related Compounds; XVIII. A Photolabile 2'–Ether of Guanosine as an Intermediate for Oligonucleotide Synthesis," *Synthesis* 7:453–454 (1977).

Patchornik et al.,"Photosensitive Protecting Groups," *J. Am. Chem. Soc.* 92:6333–35 (1970).

Pavlopoulos, et al., "Laser action from a tetramethylpyromethene–$BF_2$ complex," *Applied Optics* 27(24):4998–4999 (1988).

Perri, et al., "Tandem Photochemical Synthesis of N–Amino β–Lactams from Pyrazolidin–3–ones," *J. Org. Chem.* 55:6037–6047 (1990).

Perrin and Dwyer, et al., "Proton Exchange in Biotin: A Reinvestigation, with Implications for the Mechanism of $CO_2$ Transfer," *J. Am. Chem. Soc.* 109:5163–5167 (1987).

Peyser and Flechtner, "N–(α–Hydroxy–2–nitrosobenzyl)–1–napththamide: A Photochemical Intermediate," *J. Org. Chem.* 25:4645–4646 (1987).

Picking et al., "The use of synthetic tRNA as probes for examining nascent peptides on *Escherichia coli* ribosomes," *Biochimie* 73:1101–1107 (1991).

Picking et al., "Evidence for RNA in the Peptidyl Transferase Center of *Escherichia coli* Ribosomes as Indicated by Fluorescence," *Biochemistry* 31:12565–12570 (1992).

Picking et al., "The Conformation of Nascent Polylysine and Polyphenylalanine Peptides on Ribosomes," *J. of Biological Chemistry* 266:1534–1542 (1991).

Picking et al., "Fluoresence Characterization of the Environment Encountered by Nascent Polyalanine and Polyserine as They Exit *Escherichia coli* Ribosomes during Translation," *Biochemistry* 31:2368–2375 (1992).

Picking et al., "A synthetic alanyl–initiator tRNA with initiator tRNA properties as determined by fluorescence measurements: Comparison to a synthetic alanyl–elongator tRNA," *Nucleic Acids Research* 19:5749–5754 (1991).

Pillai, "Photoremovable Protecting Groups in Organic Synthesis," *Synthesis* 1–26 (1980).

Powell et al., "Molecular Diagnosis of Familial Adenomatous Polyposis," *N. Engl. J. Med.* 329:1982–87 (1993).

Pratt, "Coupled Transcription—Translation in Prokaryotic Cell–Free System," (*Transcription and Translation*, B.D. Hames and S.J. Higgins, Editors, p. 179–209, IRL Press, Oxford, 1984).

Promega Technical Bulletin No. 182; $tRNA^{nacendTM}$: Non–Radioactive Translation Detection System. Sep. 1–16, 1993.

Renil and Pillai, "Synthesis of fully Protected Peptides on a Tetraethyleneglycol Diacrylate (TTEGDA)–Crosslinked Polystyrene support with a Photolytically Detachable 2–Nitrobenzyl Anchoring group," *Tetrahedron Letters* 35(22):3809–3812 (1994).

Rhoer–Moja, et al., "Detection of Quantitative Polymerase Chain Reaction Products by Hybridization on Magnetic Support with $^{125}$1–Radiolabeled Probes: Quantification of c–myc Copy Numbers," *Analytical Biochemistry* 213:12–18 (1993).

Robertson, et al., "A General and Efficient Route for Chemical Aminoacylation of Transfer RNAs," *J. Am. Chem. Soc.* 113:2722–2729 (1991).

Robertson, et al., "The use of 5'–phospho–2 deoxyribocytidylylriboadenosine as a facile route to chemical aminoacylation of tRNA," *Nucleic Acids Research* 17(23):9649–9660 (1989).

Sampson and Uhlenbeck, "Biochemical and physical characterization of an unmodified yeast phenylalanine transfer RNA transcribed in vitro," *Proc. Natl. Acad. Sci. USA* 85:1033–37 (1988).

Seong and RajBhandary, "*Escherichia coli* formylmethione tRNA: Mutations in $^{GGG}$ sequence conserved in anticodon stem of initiator tRNAs affect initiation of protein synthesis and conformation of anticodon loop," *Proc. Natl. Acad. Sci. USA* 84:334–338 (1987).

Spirin et al., "A Continuous Cell–Free Translation System Capable of Producing Polypeptides in High Yield," *Sci.* 242:1162–64 (1988).

Stephen, "High–Resolution Preparative SDS–Polyacrylamide Gel Electrophoresis: Fluorescent Visualization and Electrophoretic Elution–Concentration of Protein Bands," *Anal. Biochem.* 65:369–79 (1975).

Thiele and Fahernholz, "Photocleavable Biotinylated Ligands for Affinity Chromatography," *Analytical Biochemistry* 218:330–337 (1994).

Thompson, et al., "Photocleavable Nitrobenzyl–Protein Conjugates," *Biochemical and Biophysical Research Communications* 201(3):1213–1219 (1994).

Treibs et al., "Difluorboryl–Komplexe von Di– und Tripyrrylmethenen," *Liebigs Ann. Chem.* 718:208–223 (1968).

Varshney, et al., "Initiation of protein synthesis from a termination codon," *PNAS* 87:1586–1590 (1990).

Varshney, et al., "Direct Analysis of Aminoacylation Levels of tRNAs in Vivo," *J. Biological Chemistry* 266(36):24712–24718 (1991).

Whitney, "A Photochemical approach to the synthesis of (±)–biotin," *Can. J. Chem.* 59:2650–2653 (1981).

Widder et. al., "Magnetic Microspheres: A Model System for Site Specific Drug Delivery in Vivo," *Proc. Soc. Exp. Biol. & Med.* 58:141–46 (1978).

Wieboldt, et al., "Synthesis and Photochemistry of Photolabile Derivatives of γ–Aminobutyric Acid for Chemical Kinetic Investigations of the γ–Aminobutyric Acid Receptor in the Millisecond Time Region," *Biochemistry* 33:1526–1533 (1994).

Wilchek and Bayer, "Applications of Avidin–Biotin Technology: Literature Survey," *Methods in Enzymology* 184:14–45 (1990).

Yen, et al., "Optically controlled ligand delivery, 1," *Makromol. Chem.* 190:69–82 (1989).

Zehavi, et al., "Light–Sensitive Glycosides. I. 6–Nitroveratryl β–D–Glucopyranoside and 2–Nitrobenzyl β–D–Glucopyranoside," *J. Org. Chem.* 37(14):2281–2285 (1972).

Zehavi and Herchman, "Enzymic synthesis of oligosaccharides on a polymer support, light–sensitive, water–soluble substituted poly(vinyl alcohol)," *Carbohydrate Research* 128:160–164 (1984).

Zehavi, et al., "Enzymic Synthesis of Oligosaccharides on a Polymer Support Light–Sensitive, Substituted Polyacrylamide Beads," *Carbohydrate Research* 124:23–34 (1983).

```
WT SEQUENCE  ->  1-PHASE TRANSLATION
DNA SEQUENCE    1317  B.P.   ATGGCATCTGTT ... TATTTTTCTTAA LINEAR

1/1                                     31/11                                   61/21
ATG GCA TCT GTT GTA GCT GAT CTT CCG TCT TAT GGA CCT ATC GCT TTT GAT CAG GTG GAT AAC AAC ACG AAC GCG ACC CAG CTA TTC AAA
M   A   S   V   V   A   D   L   P   S   Y   G   P   I   A   F   D   Q   V   D   N   N   T   N   A   T   Q   L   F   K
91/31                                   121/41                                  151/51
AAT AAT ATA AAC AAA ACC AGA ATG AAC GAT TTA AAC CGC GAG GAG ACG CGA TTA AAA ACC TTC ACC GAC TGG CCG CTG GAT TGG CTG GAT
N   N   I   N   K   T   R   M   N   D   L   N   R   E   E   T   R   L   K   T   F   T   D   W   P   L   D   W   L   D
181/61                                  211/71                                  241/81
AAA CGC CAA TTG GCC CAA ACC GGC ATG TAC TTC ACA CAC GCC GGC GAC AAA GTT AAA TGC TTT TTC TGC GGC GTG GAA ATC GGT TGC TGG
K   R   Q   L   A   Q   T   G   M   Y   F   T   H   A   G   D   K   V   K   C   F   F   C   G   V   E   I   G   C   W
271/91                                  301/111                                 331/111
GAG CAG GAG GAT CAG CCC GTG CCG GAA CAT CAG CGA TGG TCG CCC AAC TGT CCA CTG TTG CGC CGG CGC ACT ACC AAC AAT GTG CCG ATC
E   Q   E   D   Q   P   V   P   E   H   Q   R   W   S   P   N   C   P   L   L   R   R   R   T   T   N   N   V   P   I
361/121                                 391/131                                 421/141
AAT GCC GAA GCA TTA GAT CGC ATC CTG CCG CCA ATA AGC TAC GAT ATC TGC GGC GCC AAC GAC TCG ACG CTG GAG ATG AGG GAG CAT GCC
N   A   E   A   L   D   R   I   L   P   P   I   S   Y   D   I   C   G   A   N   D   S   T   L   E   M   R   E   H   A
451/151                                 481/161                                 511/171
TAC GCA GAA GGC GTC ATA CCC ATG TCG CAG CTA ATT CAG TCG ATT GGC ATG AAT GCA GTA AAT GCG GCA GGC AGT GTA ACT GGG ACC GCA
Y   A   E   G   V   I   P   M   S   Q   L   I   Q   S   I   G   M   N   A   V   N   A   A   G   S   V   T   G   T   A
541/181                                 571/191                                 601/201
GCC CCG CAG CCG AGG GTA ACG GTC GCC ACC CAT GCG TCG ACG GCG ACA CAG GCC ACT GGC GAT GTC CAG CCG GAG ACG TGT CGT CCT TCA
A   P   Q   P   R   V   T   V   A   T   H   A   S   T   A   T   Q   A   T   G   D   V   Q   P   E   T   C   R   P   S
631/211                                 661/221                                 691/231
GCC GCC AGT GGC AAT TAT TTT CCC CAG TAT CCC GAA TAC GCC ATC GAG ACG GCA CGC CTG CGC ACC TTC GAG GCT TGG CCG AGG AAC CTG
A   A   S   G   N   Y   F   P   Q   Y   P   E   Y   A   I   E   T   A   R   L   R   T   F   E   A   W   P   R   N   L
```

FIG. 7A

```
721/241                                                     751/251                                                     781/261
AAA CAG AAG CCC CAC CAG CTG GCC GAG GCG GGT TTC TTC TAT ACA GGC GTT GGG GAT CGC GTC CGC TGC TTC AGT TGC GGC GGT GGT CTC
K   Q   K   P   H   Q   L   A   E   A   G   F   F   Y   T   G   V   G   D   R   V   R   C   F   S   C   G   G   G   L
811/271                                                     841/281                                                     871/291
ATG GAT TGG AAC GAC AAC GAC GAG CCC TGG GAA CAG CAC GCT CTC TGG CTA AGT CAG TGC CGA TTC GTC AAA CTG ATG AAG GGT CAG CTC
M   D   W   N   D   N   D   E   P   W   E   Q   H   A   L   W   L   S   Q   C   R   F   V   K   L   M   K   G   Q   L
901/301                                                     931/311                                                     961/321
TAT ATC GAT ACG GTG GCC GCC AAA CCA GTG CTG GCC GAG GAG AAG GAG GAG AGC TCT TCG ATT GGA GGG GAC GCG GTG GCC AGC ACA CAG
Y   I   D   T   V   A   A   K   P   V   L   A   E   E   K   E   E   S   S   S   I   G   G   D   A   V   A   S   T   Q
991/331                                                     1021/341                                                    1051/351
GCT TCA GAG GAA GAG CAG CAG ACA TCA CTC TCA TCG GAG GAG GCC GTT TCG GGG GAT GTG GCT CCG TCC GTA GCT CCC ACG GCA GCC ACA
A   S   E   E   E   Q   Q   T   S   L   S   S   E   E   A   V   S   G   D   V   A   P   S   V   A   P   T   A   A   T
1081/361                                                    1111/371                                                    1141/381
CGC ATC TTC AAC AAG ATC GTC GAG GCG ACA GCG GTG GCT ACT CCC TCG ACA AAC AGC AGC GGC TCC ACC TCC ATA CCC GAG GAA AAG TTG
R   I   F   N   K   I   V   E   A   T   A   V   A   T   P   S   T   N   S   S   G   S   T   S   I   P   E   E   K   L
1171/391                                                    1201/401                                                    1231/411
TGC AAG ATC TGC TAC GGC GCC GAG TAC AAT ACG GCA TTC CTG CCA TGC GGT CAT GTG GTG GCC TGC GCC AAG TGC GCC TCC TCT GTG ACA
C   K   I   C   Y   G   A   E   Y   N   T   A   F   L   P   C   G   H   V   V   A   C   A   K   C   A   S   S   V   T
1261/421                                                    1291/431
AAG TGT CCG CTG TGC CGG AAG CCC TTC ACC GAT GTG ATG CGC GTA TAT TTT TCT TAA
K   C   P   L   C   R   K   P   F   T   D   V   M   R   V   Y   F   S   *
```

FIG. 7B

```
6-3S SEQUENCE  -> 1-PHASE TRANSLATION
DNA SEQUENCE   1317 B.P.  ATGGCATCTGTT ... TATTTTTCTTAA LINEAR

1/1                                     31/11                                   61/21
ATG GCA TCT GTT GTA GCT GAT CTT CCG TCT TAT GGA CCT ATC GCT TTT GAT CAG GTG GAT AAC AAC ACG AAC GCG ACC CAG CTA TTC AAA
M   A   S   V   V   A   D   L   P   S   Y   G   P   I   A   F   D   Q   V   D   N   N   T   N   A   T   Q   L   F   K
91/31                                   121/41                                  151/51
AAT AAT ATA AAC AAA ACC AGA ATG AAC GAT TTA AAC CGC GAG GAG ACG CGA TTA AAA ACC TTC ACC GAC TGG CCG CTG GAT TGG CTG GAT
N   N   I   N   K   T   R   M   N   D   L   N   R   E   E   T   R   L   K   T   F   T   D   W   P   L   D   W   L   D
181/61                                  211/71                                  241/81
AAA CGC CAA TTG GCC CAA ACC GGC ATG TAC TTC ACA CAC GCC GGC GAC AAA GTT AAA TGC TTT TTC TGC GGC GTG GAA ATC aGT TGC TGG
K   R   Q   L   A   Q   T   G   M   Y   F   T   H   A   G   D   K   V   K   C   F   F   C   G   V   E   I   S   C   W
271/91                                  301/111                                 331/111
GAG CAG GAG GAT CAG CCC GTG CCG GAA CAT CAG CGA TGG TCG CCC AAC TGT CCA CTG TTG CGC CGG CGC ACT ACC AAC AAT GTG CCG ATC
E   Q   E   D   Q   P   V   P   E   H   Q   R   W   S   P   N   C   P   L   L   R   R   R   T   T   N   N   V   P   I
361/121                                 391/131                                 421/141
AAT GCC GAA GCA TTA GAT CGC ATC CTG CCG CCA ATA AGC TAC GAT ATC TGC GGC GCC AAC GAC TCG ACG CTG GAG ATG AGG GAG CAT GCC
N   A   E   A   L   D   R   I   L   P   P   I   S   Y   D   I   C   G   A   N   D   S   T   L   E   M   R   E   H   A
451/151                                 481/161                                 511/171
TAC GCA GAA GGC GTC ATA CCC ATG TCG CAG CTA ATT CAG TCG ATT GGC ATG AAT GCA GTA AAT GCG GCA GGC AGT GTA ACT GGG ACC GCA
Y   A   E   G   V   I   P   M   S   Q   L   I   Q   S   I   G   M   N   A   V   N   A   A   G   S   V   T   G   T   A
541/181                                 571/191                                 601/201
GCC CCG CAG CCG AGG GTA ACG GTC GCC ACC CAT GCG TCG ACG GCG ACA CAG GCC ACT GGC GAT GTC CAG CCG GAG ACG TGT CGT CCT TCA
A   P   Q   P   R   V   T   V   A   T   H   A   S   T   A   T   Q   A   T   G   D   V   Q   P   E   T   C   R   P   S
631/211                                 661/221                                 691/231
GCC GCC AGT GGC AAT TAT TTT CCC CAG TAT CCC GAA TAC GCC ATC GAG ACG GCA CGC CTG CGC ACC TTC GAG GCT TGG CCG AGG AAC CTG
A   A   S   G   N   Y   F   P   Q   Y   P   E   Y   A   I   E   T   A   R   L   R   T   F   E   A   W   P   R   N   L
```

FIG. 8A

```
721/241                                                     751/251                                                     781/261
AAA CAG AAG CCC CAC CAG CTG GCC GAG GCG GGT TTC TTC TAT ACA GGC GTT GGG GAT CGC GTC CGC TGC TTC AGT TGC GGC GGT GGT CTC
K   Q   K   P   H   Q   L   A   E   A   G   F   F   Y   T   G   V   G   D   R   V   R   C   F   S   C   G   G   G   L
811/271                                                     841/281                                                     871/291
ATG GAT TGG AAC GAC AAC GAC GAG CCC TGG GAA CAG CAC GCT CTC TGG CTA AGT CAG TGC CGA TTC GTC AAA CTG ATG AAG GGT CAG CTC
M   D   W   N   D   N   D   E   P   W   E   Q   H   A   L   W   L   S   Q   C   R   F   V   K   L   M   K   G   Q   L
901/301                                                     931/311                                                     961/321
TAT ATC GAT ACG GTG GCC GCC AAA CCA GTG CTG GCC GAG GAG AAG GAG GAG AGC TCT TCG ATT GGA GGG GAC GCG GTG GCC AGC ACA CAG
Y   I   D   T   V   A   A   K   P   V   L   A   E   E   K   E   E   S   S   S   I   G   G   D   A   V   A   S   T   Q
991/331                                                     1021/341                                                    1051/351
GCT TCA GAG GAA GAG CAG CAG ACA TCA CTC TCA TCG GAG GAG GCC GTT TCG GGG GAT GTG GCT CCG TCC GTA GCT CCC ACG GCA GCC ACA
A   S   E   E   E   Q   Q   T   S   L   S   S   E   E   A   V   S   G   D   V   A   P   S   V   A   P   T   A   A   T
1081/361                                                    1111/371                                                    1141/381
CGC ATC TTC AAC AAG ATC GTC GAG GCG ACA GCG GTG GCT ACT CCC TCG ACA AAC AGC AGC GGC TCC ACC TCC ATA CCC GAG GAA AAG TTG
R   I   F   N   K   I   V   E   A   T   A   V   A   T   P   S   T   N   S   S   G   S   T   S   I   P   E   E   K   L
1171/391                                                    1201/401                                                    1231/411
TGC AAG ATC TGC TAC GGC GCC GAG TAC AAT ACG GCA TTC CTG CCA TGC GGT CAT GTG GTG GCC TGC GCC AAG TGC GCC TCC TCT GTG ACA
C   K   I   C   Y   G   A   E   Y   N   T   A   F   L   P   C   G   H   V   V   A   C   A   K   C   A   S   S   V   T
1261/421                                                    1291/431
AAG TGT CCG CTG TGC CGG AAG CCC TTC ACC GAT GTG ATG CGC GTA TAT TTT TCT TAA
K   C   P   L   C   R   K   P   F   T   D   V   M   R   V   Y   F   S   *
```

FIG. 8B

```
45-2S SEQUENCE  ->  1-PHASE TRANSLATION
DNA SEQUENCE    1317  B.P.   ATGGCATCTGTT ... TATTTTTCTTAA LINEAR

1/1                                         31/11                                       61/21
ATG GCA TCT GTT GTA GCT GAT CTT CCG TCT TAT GGA CCT ATC GCT TTT GAT CAG GTG GAT AAC AAC ACG AAC GCG ACC CAG CTA TTC AAA
M   A   S   V   V   A   D   L   P   S   Y   G   P   I   A   F   D   Q   V   D   N   N   T   N   A   T   Q   L   F   K
91/31                                       121/41                                      151/51
AAT AAT ATA AAC AAA ACC AGA ATG AAC GAT TTA AAC CGC GAG GAG ACG CGA TTA AAA ACC TTC ACC GAC TGG CCG CTG GAT TGG CTG GAT
N   N   I   N   K   T   R   M   N   D   L   N   R   E   E   T   R   L   K   T   F   T   D   W   P   L   D   W   L   D
181/61                                      211/71                                      241/81
AAA CGC CAA TTG GCC CAA ACC GGC ATG TAC TTC ACA CAC GCC GGC GAC AAA GTT AAA TGC TTT TTC TGC GGC GTG GAA ATC GaT TGC TGG
K   R   Q   L   A   Q   T   G   M   Y   F   T   H   A   G   D   K   V   K   C   F   F   C   G   V   E   I   D   C   W
271/91                                      301/111                                     331/111
GAG CAG GAG GAT CAG CCC GTG CCG GAA CAT CAG CGA TGG TCG CCC AAC TGT CCA CTG TTG CGC CGG CGC ACT ACC AAC AAT GTG CCG ATC
E   Q   E   D   Q   P   V   P   E   H   Q   R   W   S   P   N   C   P   L   L   R   R   R   T   T   N   N   V   P   I
361/121                                     391/131                                     421/141
AAT GCC GAA GCA TTA GAT CGC ATC CTG CCG CCA ATA AGC TAC GAT ATC TGC GGC GCC AAC GAC TCG ACG CTG GAG ATG AGG GAG CAT GCC
N   A   E   A   L   D   R   I   L   P   P   I   S   Y   D   I   C   G   A   N   D   S   T   L   E   M   R   E   H   A
451/151                                     481/161                                     511/171
TAC GCA GAA GGC GTC ATA CCC ATG TCG CAG CTA ATT CAG TCG ATT GGC ATG AAT GCA GTA AAT GCG GCA GGC AGT GTA ACT GGG ACC GCA
Y   A   E   G   V   I   P   M   S   Q   L   I   Q   S   I   G   M   N   A   V   N   A   A   G   S   V   T   G   T   A
541/181                                     571/191                                     601/201
GCC CCG CAG CCG AGG GTA ACG GTC GCC ACC CAT GCG TCG ACG GCG ACA CAG GCC ACT GGC GAT GTC CAG CCG GAG ACG TGT CGT CCT TCA
A   P   Q   P   R   V   T   V   A   T   H   A   S   T   A   T   Q   A   T   G   D   V   Q   P   E   T   C   R   P   S
631/211                                     661/221                                     691/231
GCC GCC AGT GGC AAT TAT TTT CCC CAG TAT CCC GAA TAC GCC ATC GAG ACG GCA CGC CTG CGC ACC TTC GAG GCT TGG CCG AGG AAC CTG
A   A   S   G   N   Y   F   P   Q   Y   P   E   Y   A   I   E   T   A   R   L   R   T   F   E   A   W   P   R   N   L
```

FIG. 9A

```
721/241                                       751/251                                       781/261
AAA CAG AAG CCC CAC CAG CTG GCC GAG GCG GGT TTC TTC TAT ACA GGC GTT GGG GAT CGC GTC CGC TGC TTC AGT TGC GGC GGT GGT CTC
K   Q   K   P   H   Q   L   A   E   A   G   F   F   Y   T   G   V   G   D   R   V   R   C   F   S   C   G   G   G   L
811/271                                       841/281                                       871/291
ATG GAT TGG AAC GAC AAC GAC GAG CCC TGG GAA CAG CAC GCT CTC TGG CTA AGT CAG TGC CGA TTC GTC AAA CTG ATG AAG GGT CAG CTC
M   D   W   N   D   N   D   E   P   W   E   Q   H   A   L   W   L   S   Q   C   R   F   V   K   L   M   K   G   Q   L
901/301                                       931/311                                       961/321
TAT ATC GAT ACG GTG GCC GCC AAA CCA GTG CTG GCC GAG GAG AAG GAG GAG AGC TCT TCG ATT GGA GGG GAC GCG GTG GCC AGC ACA CAG
Y   I   D   T   V   A   A   K   P   V   L   A   E   E   K   E   E   S   S   S   I   G   G   D   A   V   A   S   T   Q
991/331                                       1021/341                                      1051/351
GCT TCA GAG GAA GAG CAG CAG ACA TCA CTC TCA TCG GAG GAG GCC GTT TCG GGG GAT GTG GCT CCG TCC GTA GCT CCC ACG GCA GCC ACA
A   S   E   E   E   Q   Q   T   S   L   S   S   E   E   A   V   S   G   D   V   A   P   S   V   A   P   T   A   A   T
1081/361                                      1111/371                                      1141/381
CGC ATC TTC AAC AAG ATC GTC GAG GCG ACA GCG GTG GCT ACT CCC TCG ACA AAC AGC AGC GGC TCC ACC TCC ATA CCC GAG GAA AAG TTG
R   I   F   N   K   I   V   E   A   T   A   V   A   T   P   S   T   N   S   S   G   S   T   S   I   P   E   E   K   L
1171/391                                      1201/401                                      1231/411
TGC AAG ATC TGC TAC GGC GCC GAG TAC AAT ACG GCA TTC CTG CCA TGC GGT CAT GTG GTG GCC TGC GCC AAG TGC GCC TCC TCT GTG ACA
C   K   I   C   Y   G   A   E   Y   N   T   A   F   L   P   C   G   H   V   V   A   C   A   K   C   A   S   S   V   T
1261/421                                      1291/431
AAG TGT CCG CTG TGC CGG AAG CCC TTC ACC GAT GTG ATG CGC GTA TAT TTT TCT TAA
K   C   P   L   C   R   K   P   F   T   D   V   M   R   V   Y   F   S   *
```

FIG. 9B

```
23-4S AND 23-8S SEQUENCE  ->  1-PHASE TRANSLATION
DNA SEQUENCE    1317  B.P.   ATGGCATCTGTT ... TATTTTTCTTAA LINEAR

1/1                                       31/11                                     61/21
ATG GCA TCT GTT GTA GCT GAT CTT CCG TCT TAT GGA CCT ATC GCT TTT GAT CAG GTG GAT AAC AAC ACG AAC GCG ACC CAG CTA TTC AAA
M   A   S   V   V   A   D   L   P   S   Y   G   P   I   A   F   D   Q   V   D   N   N   T   N   A   T   Q   L   F   K
91/31                                     121/41                                    151/51
AAT AAT ATA AAC AAA ACC AGA ATG AAC GAT TTA AAC CGC GAG GAG ACG CGA TTA AAA ACC TTC ACC GAC TGG CCG CTG GAT TGG CTG GAT
N   N   I   N   K   T   R   M   N   D   L   N   R   E   E   T   R   L   K   T   F   T   D   W   P   L   D   W   L   D
181/61                                    211/71                                    241/81
AAA CGC CAA TTG GCC CAA ACC GGC ATG TAC TTC ACA CAC GCC GGC GAC AAA GTT AAA TGC TTT TTC TGC GGC GTG GAA ATC GGT TGC TGG
K   R   Q   L   A   Q   T   G   M   Y   F   T   H   A   G   D   K   V   K   C   F   F   C   G   V   E   I   G   C   W
271/91                                    301/111                                   331/111
GAG CAG GAG GAT CAG CCC GTG CCG GAA CAT CAG CGA TGG TCG CCC AAC TGT CCA CTG TTG CGC CGG CGC ACT ACC AAC AAT GTG CCG ATC
E   Q   E   D   Q   P   V   P   E   H   Q   R   W   S   P   N   C   P   L   L   R   R   R   T   T   N   N   V   P   I
361/121                                   391/131                                   421/141
AAT GCC GAA GCA TTA GAT CGC ATC CTG CCG CCA ATA AGC TAC GAT ATC TGC GGC GCC AAC GAC TCG ACG CTG GAG ATG AGG GAG CAT GCC
N   A   E   A   L   D   R   I   L   P   P   I   S   Y   D   I   C   G   A   N   D   S   T   L   E   M   R   E   H   A
451/151                                   481/161                                   511/171
TAC GCA GAA GGC GTC ATA CCC ATG TCG CAG CTA ATT CAG TCG ATT GGC ATG AAT GCA GTA AAT GCG GCA GGC AGT GTA ACT GGG ACC GCA
Y   A   E   G   V   I   P   M   S   Q   L   I   Q   S   I   G   M   N   A   V   N   A   A   G   S   V   T   G   T   A
541/181                                   571/191                                   601/201
GCC CCG CAG CCG AGG GTA ACG GTC GCC ACC CAT GCG TCG ACG GCG ACA CAG GCC ACT GGC GAT GTC CAG CCG GAG ACG TGT CGT CCT TCA
A   P   Q   P   R   V   T   V   A   T   H   A   S   T   A   T   Q   A   T   G   D   V   Q   P   E   T   C   R   P   S
631/211                                   661/221                                   691/231
GCC GCC AGT GGC AAT TAT TTT CCC CAG TAT CCC GAA TAC GCC ATC GAG ACG GCA CGC CTG CGC ACC TTC GAG GCT TGG CCG AGG AAC CTG
A   A   S   G   N   Y   F   P   Q   Y   P   E   Y   A   I   E   T   A   R   L   R   T   F   E   A   W   P   R   N   L
```

FIG. 10A

721/241 751/251 781/261
AAA CAG AAG CCC CAC CAG CTG GCC GAG GCG GGT TTC TTC TAT ACA GGC GTT GGG GAT CGC GTC CGC TGC TTC AGT TGC GGC GGT AGT CTC
K Q K P H Q L A E A G F F Y T G V G D R V R C F S C G G S L
811/271 841/281 871/291
ATG GAT TGG AAC GAC AAC GAC GAG CCC TGG GAA CAG CAC GCT CTC TGG CTA AGT CAG TGC CGA TTC GTC AAA CTG ATG AAG GGT CAG CTC
M D W N D N D E P W E Q H A L W L S Q C R F V K L M K G Q L
901/301 931/311 961/321
TAT ATC GAT ACG GTG GCC GCC AAA CCA GTG CTG GCC GAG GAG AAG GAG GAG AGC TCT TCG ATT GGA GGG GAC GCG GTG GCC AGC ACA CAG
Y I D T V A A K P V L A E E K E E S S S I G G D A V A S T Q
991/331 1021/341 1051/351
GCT TCA GAG GAA GAG CAG CAG ACA TCA CTC TCA TCG GAG GAG GCC GTT TCG GGG GAT GTG GCT CCG TCC GTA GCT CCC ACG GCA GCC ACA
A S E E E Q Q T S L S S E E A V S G D V A P S V A P T A A T
1081/361 1111/371 1141/381
CGC ATC TTC AAC AAG ATC GTC GAG GCG ACA GCG GTG GCT ACT CCC TCG ACA AAC AGC AGC GGC TCC ACC TCC ATA CCC GAG GAA AAG TTG
R I F N K I V E A T A V A T P S T N S S G S T S I P E E K L
1171/391 1201/401 1231/411
TGC AAG ATC TGC TAC GGC GCC GAG TAC AAT ACG GCA TTC CTG CCA TGC GGT CAT GTG GTG GCC TGC GCC AAG TGC GCC TCC TCT GTG ACA
C K I C Y G A E Y N T A F L P C G H V V A C A K C A S S V T
1261/421 1291/431
AAG TGT CCG CTG TGC CGG AAG CCC TTC ACC GAT GTG ATG CGC GTA TAT TTT TCT TAA
K C P L C R K P F T D V M R V Y F S *

FIG. 10B

```
11-3E SEQUENCE  -> 1-PHASE TRANSLATION
DNA SEQUENCE    1317 B.P.   ATGGCATCTGTT ... TATTTTTCTTAA LINEAR

1/1                                     31/11                                   61/21
ATG GCA TCT GTT GTA GCT GAT CTT CCG TCT TAT GGA CCT ATC GCT TTT GAT CAG GTG GAT AAC AAC ACG AAC GCG ACC CAG CTA TTC AAA
M   A   S   V   V   A   D   L   P   S   Y   G   P   I   A   F   D   Q   V   D   N   N   T   N   A   T   Q   L   F   K
91/31                                   121/41                                  151/51
AAT AAT ATA AAC AAA ACC AGA ATG AAC GAT TTA AAC CGC GAG GAG ACG CGA TTA AAA ACC TTC ACC GAC TGG CCG CTG GAT TGG CTG GAT
N   N   I   N   K   T   R   M   N   D   L   N   R   E   E   T   R   L   K   T   F   T   D   W   P   L   D   W   L   D
181/61                                  211/71                                  241/81
AAA CGC CAA TTG GCC CAA ACC GGC ATG TAC TTC ACA CAC GCC GGC GAC AAA GTT AAA TGC TTT TTC TGC GGC GTG GAA ATC GGT TGC TGG
K   R   Q   L   A   Q   T   G   M   Y   F   T   H   A   G   D   K   V   K   C   F   F   C   G   V   E   I   G   C   W
271/91                                  301/111                                 331/111
GAG CAG GAG GAT CAG CCC GTG CCG GAA CAT CAG CGA TGG TCG CCC AAC TGT CCA CTG TTG CGC CGG CGC ACT ACC AAC AAa GTG CCG ATC
E   Q   E   D   Q   P   V   P   E   H   Q   R   W   S   P   N   C   P   L   L   R   R   R   T   T   N   K   V   P   I
361/121                                 391/131                                 421/141
AAT GCC GAA GCA TTA GAT CGC ATC CTG CCG CCA ATA AGC TAC GAT ATC TGC GGC GCC AAC GAC TCG ACG CTG GAG ATG AGG GAG CAT GCC
N   A   E   A   L   D   R   I   L   P   P   I   S   Y   D   I   C   G   A   N   D   S   T   L   E   M   R   E   H   A
451/151                                 481/161                                 511/171
TAC GCA GAA GGC GTC ATA CCC ATG TCG CAG CTA ATT CAG TCG ATT GGC ATG AAT GCA GTA AAT GCG GCA GGC AGT GTA ACT GGG ACC GCA
Y   A   E   G   V   I   P   M   S   Q   L   I   Q   S   I   G   M   N   A   V   N   A   A   G   S   V   T   G   T   A
541/181                                 571/191                                 601/201
GCC CCG CAG CCG AGG GTA ACG GTC GCC ACC CAT GCG TCG ACG GCG ACA CAG GCC ACT GGC GAT GTC CAG CCG GAG ACG TGT CGT CCT TCA
A   P   Q   P   R   V   T   V   A   T   H   A   S   T   A   T   Q   A   T   G   D   V   Q   P   E   T   C   R   P   S
631/211                                 661/221                                 691/231
GCC GCC AGT GGC AAT TAT TTT CCC CAG TAT CCC GAA TAC GCC ATC GAG ACG GCA CGC CTG CGC ACC TTC GAG GCT TGG CCG AGG AAC CTG
A   A   S   G   N   Y   F   P   Q   Y   P   E   Y   A   I   E   T   A   R   L   R   T   F   E   A   W   P   R   N   L
```

FIG. 11A

721/241 751/251 781/261
AAA CAG AAG CCC CAC CAG CTG GCC GAG GCG GGT TTC TTC TAT ACA GGC GTT GGG GAT CGC GTC CGC TGC TTC AGT TGC GGC GGT GGT CTC
K Q K P H Q L A E A G F F Y T G V G D R V R C F S C G G G L
811/271 841/281 871/291
ATG GAT TGG AAC GAC AAC GAC GAG CCC TGG GAA CAG CAC GCT CTC TGG CTA AGT CAG TGC CGA TTC GTC AAA CTG ATG AAG GGT CAG CTC
M D W N D N D E P W E Q H A L W L S Q C R F V K L M K G Q L
901/301 931/311 961/321
TAT ATC GAT ACG GTG GCC GCC AAA CCA GTG CTG GCC GAG GAG AAG GAG GAG AGC TCT TCG ATT GGA GGG GAC GCG GTG GCC AGC ACA CAG
Y I D T V A A K P V L A E E K E E S S S I G G D A V A S T Q
991/331 1021/341 1051/351
GCT TCA GAG GAA GAG CAG CAG ACA TCA CTC TCA TCG GAG GAG GCC GTT TCG GGG GAT GTG GCT CCG TCC GTA GCT CCC ACG GCA GCC ACA
A S E E E Q Q T S L S S E E A V S G D V A P S V A P T A A T
1081/361 1111/371 1141/381
CGC ATC TTC AAC AAG ATC GTC GAG GCG ACA GCG GTG GCT ACT CCC TCG ACA AAC AGC AGC GGC TCC ACC TCC ATA CCC GAG GAA AAG TTG
R I F N K I V E A T A V A T P S T N S S G S T S I P E E K L
1171/391 1201/401 1231/411
TGC AAG ATC TGC TAC GGC GCC GAG TAC AAT ACG GCA TTC CTG CCA TGC GGT CAT GTG GTG GCC TGC GCC AAG TGC GCC TCC TCT GTG ACA
C K I C Y G A E Y N T A F L P C G H V V A C A K C A S S V T
1261/421 1291/431
AAG TGT CCG CTG TGC CGG AAG CCC TTC ACC GAT GTG ATG CGC GTA TAT TTT TCT TAA
K C P L C R K P F T D V M R V Y F S *

FIG. 11B

```
22-8S SEQUENCE  ->  1-PHASE TRANSLATION
DNA SEQUENCE    1317  B.P.   ATGGCATCTGTT ... TATTTTTCTTAA LINEAR

1/1                                         31/11                                       61/21
ATG GCA TCT GTT GTA GCT GAT CTT CCG TCT TAT GGA CCT ATC GCT TTT GAT CAG GTG GAT AAC AAC ACG AAC GCG ACC CAG CTA TTC AAA
M   A   S   V   V   A   D   L   P   S   Y   G   P   I   A   F   D   Q   V   D   N   N   T   N   A   T   Q   L   F   K
91/31                                       121/41                                      151/51
AAT AAT ATA AAC AAA ACC AGA ATG AAC GAT TTA AAC CGC GAG GAG ACG CGA TTA AAA ACC TTC ACC GAC TGG CCG CTG GAT TGG CTG GAT
N   N   I   N   K   T   R   M   N   D   L   N   R   E   E   T   R   L   K   T   F   T   D   W   P   L   D   W   L   D
181/61                                      211/71                                      241/81
AAA CGC CAA TTG GCC CAA ACC GGC ATG TAC TTC ACA CAC GCC GGC GAC AAA GTT AAA TGC TTT TTC TGC GGC GTG GAA ATC GGT TGC TGG
K   R   Q   L   A   Q   T   G   M   Y   F   T   H   A   G   D   K   V   K   C   F   F   C   G   V   E   I   G   C   W
271/91                                      301/111                                     331/111
GAG CAG GAG GAT CAG CCC GTG CCG GAA CAT CAG CGA TGG TCG CCC AAC TGT CCA CTG TTG CGC CGG CGC ACT ACC AAC AAT GTG CCG ATC
E   Q   E   D   Q   P   V   P   E   H   Q   R   W   S   P   N   C   P   L   L   R   R   R   T   T   N   N   V   P   I
361/121                                     391/131                                     421/141
AAT GCC GAA GCA TTA GAT CGC ATC CTG CCG CCA ATA AGC TAC GAT ATC TGC GGC GCC AAC GAC TCG ACG CTG GAG ATG AGG GAG CAT GCC
N   A   E   A   L   D   R   I   L   P   P   I   S   Y   D   I   C   G   A   N   D   S   T   L   E   M   R   E   H   A
451/151                                     481/161                                     511/171
TAC GCA GAA GGC GTC ATA CCC ATG TCG CAG CTA ATT CAG TCG ATT GGC ATG AAT GCA GTA AAT GCG GCA GGC AGT GTA ACT GGG ACC GCA
Y   A   E   G   V   I   P   M   S   Q   L   I   Q   S   I   G   M   N   A   V   N   A   A   G   S   V   T   G   T   A
541/181                                     571/191                                     601/201
GCC CCG CAG CCG AGG GTA ACG GTC GCC ACC CAT GCG TCG ACG GCG ACA CAG GCC ACT GGC GAT GTC CAG CCG GAG ACG TGT CGT CCT TCA
A   P   Q   P   R   V   T   V   A   T   H   A   S   T   A   T   Q   A   T   G   D   V   Q   P   E   T   C   R   P   S
631/211                                     661/221                                     691/231
GCC GCC AGT GGC AAT TAT TTT CCC CAG TAT CCC GAA TAC GCC ATC GAG ACG GCA CGC CTG CGC ACC TTC GAG GCT TGG CCG AGG AAC CTG
A   A   S   G   N   Y   F   P   Q   Y   P   E   Y   A   I   E   T   A   R   L   R   T   F   E   A   W   P   R   N   L
```

FIG. 12A

```
721/241                                     751/251                                     781/261
AAA CAG AAG CCC CAC CAG CTG GCC GAG GCG GGT TTC TTC TAT ACA GGC GTT GGG GAT CGC GTC CGC TGC TTC AGT TGC GGC GGT GGT CTC
K   Q   K   P   H   Q   L   A   E   A   G   F   F   Y   T   G   V   G   D   R   V   R   C   F   S   C   G   G   G   L
811/271                                     841/281                                     871/291
ATG GAT TGG AAC GAC AAC GAC GAG CCC TGG GAA CAG CAC GCT CTC TGG CTA AGT CAG TGC CGA TTC GTC AAA CTG ATG AAG GGT CAG CTC
M   D   W   N   D   N   D   E   P   W   E   Q   H   A   L   W   L   S   Q   C   R   F   V   K   L   M   K   G   Q   L
901/301                                     931/311                                     961/321
TAT ATC GAT ACG GTG GCC GCC AAA CCA GTG CTG GCC GAG GAG AAG GAG GAG AGC TCT TCG ATT GGA GGG GAC GCG GTG GCC AGC ACA CAG
Y   I   D   T   V   A   A   K   P   V   L   A   E   E   K   E   E   S   S   S   I   G   G   D   A   V   A   S   T   Q
991/331                                     1021/341                                    1051/351
GCT TCA GAG GAA GAG CAG CAG ACA TCA CTC TCA TCG GAG GAG GCC GTT TCG GGG GAT GTG GCT CCG TCC GTA GCT CCC ACG GCA GCC ACA
A   S   E   E   E   Q   Q   T   S   L   S   S   E   E   A   V   S   G   D   V   A   P   S   V   A   P   T   A   A   T
1081/361                                    1111/371                                    1141/381
CGC ATC TTC AAC AAG ATC GTC GAG GCG ACA GCG GTG GCT ACT CCC TCG ACA AAC AGC AGC GGC TCC ACC TCC ATA CCC GAG GAA AAG TTG
R   I   F   N   K   I   V   E   A   T   A   V   A   T   P   S   T   N   S   S   G   S   T   S   I   P   E   E   K   L
1171/391                                    1201/401                                    1231/411
TGC AAG ATC TGC TAC GGC GCC GAG TAC AAT ACG GCA TTC CTG CCA TGC GGT CAT GTG GTG GCC TGC GCC AAG TAC GCC TCC TCT GTG ACA
C   K   I   C   Y   G   A   E   Y   N   T   A   F   L   P   C   G   H   V   V   A   C   A   K   Y   A   S   S   V   T
1261/421                                    1291/431
AAG TGT CCG CTG TGC CGG AAG CCC TTC ACC GAT GTG ATG CGC GTA TAT TTT TCT TAA
K   C   P   L   C   R   K   P   F   T   D   V   M   R   V   Y   F   S   *
```

FIG. 12B

```
21-4S SEQUENCE  ->  1-PHASE TRANSLATION
DNA SEQUENCE    1317  B.P.   ATGGCATCTGTT ... TATTTTTCTTAA LINEAR

1/1                                         31/11                                       61/21
ATG GCA TCT GTT GTA GCT GAT CTT CCG TCT TAT GGA CCT ATC GCT TTT GAT CAG GTG GAT AAC AAC ACG AAC GCG ACC CAG CTA TTC AAA
M   A   S   V   V   A   D   L   P   S   Y   G   P   I   A   F   D   Q   V   D   N   N   T   N   A   T   Q   L   F   K
91/31                                       121/41                                      151/51
AAT AAT ATA AAC AAA ACC AGA ATG AAC GAT TTA AAC CGC GAG GAG ACG CGA TTA AAA ACC TTC ACC GAC TGG CCG CTG GAT TGG CTG GAT
N   N   I   N   K   T   R   M   N   D   L   N   R   E   E   T   R   L   K   T   F   T   D   W   P   L   D   W   L   D
181/61                                      211/71                                      241/81
AAA CGC CAA TTG GCC CAA ACC GGC ATG TAC TTC ACA CAC GCC GGC GAC AAA GTT AAA TGC TTT TTC TGC GGC GTG GAA ATC GGT TGC TGG
K   R   Q   L   A   Q   T   G   M   Y   F   T   H   A   G   D   K   V   K   C   F   F   C   G   V   E   I   G   C   W
271/91                                      301/111                                     331/111
GAG CAG GAG GAT CAG CCC GTG CCG GAA CAT CAG CGA TGG TCG CCC AAC TGT CCA CTG TTG CGC CGG CGC ACT ACC AAC AAT GTG CCG ATC
E   Q   E   D   Q   P   V   P   E   H   Q   R   W   S   P   N   C   P   L   L   R   R   R   T   T   N   N   V   P   I
361/121                                     391/131                                     421/141
AAT GCC GAA GCA TTA GAT CGC ATC CTG CCG CCA ATA AGC TAC GAT ATC TGC GGC GCC AAC GAC TCG ACG CTG GAG ATG AGG GAG CAT GCC
N   A   E   A   L   D   R   I   L   P   P   I   S   Y   D   I   C   G   A   N   D   S   T   L   E   M   R   E   H   A
451/151                                     481/161                                     511/171
TAC GCA GAA GGC GTC ATA CCC ATG TCG CAG CTA ATT CAG TCG ATT GGC ATG AAT GCA GTA AAT GCG GCA GGC AGT GTA ACT GGG ACC GCA
Y   A   E   G   V   I   P   M   S   Q   L   I   Q   S   I   G   M   N   A   V   N   A   A   G   S   V   T   G   T   A
541/181                                     571/191                                     601/201
GCC CCG CAG CCG AGG GTA ACG GTC GCC ACC CAT GCG TCG ACG GCG ACA CAG GCC ACT GGC GAT GTC CAG CCG GAG ACG TGT CGT CCT TCA
A   P   Q   P   R   V   T   V   A   T   H   A   S   T   A   T   Q   A   T   G   D   V   Q   P   E   T   C   R   P   S
631/211                                     661/221                                     691/231
GCC GCC AGT GGC AAT TAT TTT CCC CAG TAT CCC GAA TAC GCC ATC GAG ACG GCA CGC CTG CGC ACC TTC GAG GCT TGG CCG AGG AAC CTG
A   A   S   G   N   Y   F   P   Q   Y   P   E   Y   A   I   E   T   A   R   L   R   T   F   E   A   W   P   R   N   L
```

FIG. 13A

```
721/241                                751/251                                781/261
AAA CAG AAG CCC CAC CAG CTG GCC GAG GCG GGT TTC TTC TAT ACA GGC GTT GGG GAT CGC GTC CGC TGC TTC AGT TGC GGC GGT GGT CTC
K   Q   K   P   H   Q   L   A   E   A   G   F   F   Y   T   G   V   G   D   R   V   R   C   F   S   C   G   G   G   L
811/271                                841/281                                871/291
ATG GAT TGG AAC GAC AAC GAC GAG CCC TGG GAA CAG CAC GCT CTC TGG CTA AGT CAG TGC CGA TTC GTC AAA CTG ATG AAG GGT CAG CTC
M   D   W   N   D   N   D   E   P   W   E   Q   H   A   L   W   L   S   Q   C   R   F   V   K   L   M   K   G   Q   L
901/301                                931/311                                961/321
TAT ATC GAT ACG GTG GCC GCC AAA CCA GTG CTG GCC GAG GAG AAG GAG GAG AGC TCT TCG ATT GGA GGG GAC GCG GTG GCC AGC ACA CAG
Y   I   D   T   V   A   A   K   P   V   L   A   E   E   K   E   E   S   S   S   I   G   G   D   A   V   A   S   T   Q
991/331                                1021/341                               1051/351
GCT TCA GAG GAA GAG CAG CAG ACA TCA CTC TCA TCG GAG GAG GCC GTT TCG GGG GAT GTG GCT CCG TCC GTA GCT CCC ACG GCA GCC ACA
A   S   E   E   E   Q   Q   T   S   L   S   S   E   E   A   V   S   G   D   V   A   P   S   V   A   P   T   A   A   T
1081/361                               1111/371                               1141/381
CGC ATC TTC AAC AAG ATC GTC GAG GCG ACA GCG GTG GCT ACT CCC TCG ACA AAC AGC AGC GGC TCC ACC TCC ATA CCC GAG GAA AAG TTG
R   I   F   N   K   I   V   E   A   T   A   V   A   T   P   S   T   N   S   S   G   S   T   S   I   P   E   E   K   L
1171/391                               1201/401                               1231/411
TGC AAG ATC TGC TAC GGC GCC GAG TAC AAT ACG GCA TTC CTG CCA TAC GGT CAT GTG GTG GCC TGC GCC AAG TGC GCC TCC TCT GTG ACA
C   K   I   C   Y   G   A   E   Y   N   T   A   F   L   P   Y   G   H   V   V   A   C   A   K   C   A   S   S   V   T
1261/421                               1291/431
AAG TGT CCG CTG TGC CGG AAG CCC TTC ACC GAT GTG ATG CGC GTA TAT TTT TCT TAA
K   C   P   L   C   R   K   P   F   T   D   V   M   R   V   Y   F   S   *
```

FIG. 13B

```
33-1S SEQUENCE  ->  1-PHASE TRANSLATION
DNA SEQUENCE    1304  B.P.   ATGGCATCTGTT ... tatttttcttaa LINEAR

1/1                                     31/11                                   61/21
ATG GCA TCT GTT GTA GCT GAT CTT CCG TCT TAT GGA CCT ATC GCT TTT GAT CAG GTG GAT AAC AAC ACG AAC GCG ACC CAG CTA TTC AAA
M   A   S   V   V   A   D   L   P   S   Y   G   P   I   A   F   D   Q   V   D   N   N   T   N   A   T   Q   L   F   K
91/31                                   121/41                                  151/51
AAT AAT ATA AAC AAA ACC AGA ATG AAC GAT TTA AAC CGC GAG GAG ACG CGA TTA AAA ACC TTC ACC GAC TGG CCG CTG GAT TGG CTG GAT
N   N   I   N   K   T   R   M   N   D   L   N   R   E   E   T   R   L   K   T   F   T   D   W   P   L   D   W   L   D
181/61                                  211/71                                  241/81
AAA CGC CAA TTG GCC CAA ACC GGC ATG TAC TTC ACA CAC GCC GGC GAC AAA GTT AAA TGC TTT TTC TGC GGC GTG GAA ATC GGT TGC TGG
K   R   Q   L   A   Q   T   G   M   Y   F   T   H   A   G   D   K   V   K   C   F   F   C   G   V   E   I   G   C   W
271/91                                  301/111                                 331/111
GAG CAG GAG GAT CAG CCC GTG CCG GAA CAT CAG CGA TGG TCG CCC AAC TGT CCA CTG TTG CGC CGG CGC ACT ACC AAC AAT GTG CCG ATC
E   Q   E   D   Q   P   V   P   E   H   Q   R   W   S   P   N   C   P   L   L   R   R   R   T   T   N   N   V   P   I
361/121                                 391/131                                 421/141
AAT GCC GAA GCA TTA GAT CGC ATC CTG CCG CCA ATA AGC TAC GAT ATC TGC GGC GCC AAC GAC TCG ACG CTG GAG ATG AGG GAG CAT GCC
N   A   E   A   L   D   R   I   L   P   P   I   S   Y   D   I   C   G   A   N   D   S   T   L   E   M   R   E   H   A
451/151                                 481/161                                 511/171
TAC GCA GAA GGC GTC ATA CCC ATG TCG CAG CTA ATT CAG TCG ATT GGC ATG AAT GCA GTA AAT GCG GCA GGC AGT GTA ACT GGG ACC GCA
Y   A   E   G   V   I   P   M   S   Q   L   I   Q   S   I   G   M   N   A   V   N   A   A   G   S   V   T   G   T   A
541/181                                 571/191                                 601/201
GCC CCG CAG CCG AGG GTA ACG GTC GCC ACC CAT GCG TCG ACG GCG ACA CAG GCC ACT GGC GAT GTC CAG CCG GAG ACG TGT CGT CCT TCA
A   P   Q   P   R   V   T   V   A   T   H   A   S   T   A   T   Q   A   T   G   D   V   Q   P   E   T   C   R   P   S
631/211                                 661/221                                 691/231
GCC GCC AGT GGC AAT TAT TTT CCC CAG TAT CCC GAA TAC GCC ATC GAG ACG GCA CGC CTG CGC ACC TTC GAG GCT TGG CCG AGG AAC CTG
A   A   S   G   N   Y   F   P   Q   Y   P   E   Y   A   I   E   T   A   R   L   R   T   F   E   A   W   P   R   N   L
```

FIG. 14A

```
721/241                                     751/251                                     781/261
AAA CAG AAG CCC CAC CAG CTG GCC GAG GCG GGT TTC TTC TAT ACA GGC GTT GGG GAT CGC GTC CGC TGC TTC AGT TGC GGC GGT GGT CTC
K   Q   K   P   H   Q   L   A   E   A   G   F   F   Y   T   G   V   G   D   R   V   R   C   F   S   C   G   G   G   L
811/271                                     841/281                                     871/291
ATG GAT TGG AAC GAC AAC GAC GAG CCC TGG GAA CAG CAC GCT CTC TGG CTA AGT CAG TGC CGA TTC GTC AAA CTG ATG AAG GGT CAG CTC
M   D   W   N   D   N   D   E   P   W   E   Q   H   A   L   W   L   S   Q   C   R   F   V   K   L   M   K   G   Q   L
901/301                                     931/311                                     961/321
TAT ATC GAT ACG GTG GCC GCC AAA CCA GTG CTG GCC GAG GAG AAG GAG GAG AGC TCT TCG ATT GGA GGG GAC GCG GTG GCC AGC ACA CAG
Y   I   D   T   V   A   A   K   P   V   L   A   E   E   K   E   E   S   S   S   I   G   G   D   A   V   A   S   T   Q
991/331                                     1021/341                                    1051/351
GCT TCA GAG GAA GAG CAT CAT CGG AGG AGG CCG TTT CGG GGG ATG TGG CTC CGT CCG TAG CTC CCA CGG CAG CCA CAC GCA TCT TCA ACA
A   S   E   E   E   H   H   R   R   R   P   F   R   G   M   W   L   R   P   *   L   P   R   Q   P   H   A   S   S   T
1081/361                                    1111/371                                    1141/381
AGA TCG TCG AGG CGA CAG CGG TGG CTA CTC CCT CGA CAA ACA GCA GCG GCT CCA CCT CCA TAC CCG AGG AAA AGT TGT GCA AGA TCT GCT
R   S   S   R   R   Q   R   W   L   L   P   R   Q   T   A   A   A   P   P   P   Y   P   R   K   S   C   A   R   S   A
1171/391                                    1201/401                                    1231/411
ACG GCG CCG AGT ACA ATA CGG CAT TCC TGC CAT GCG GTC ATG TGG TGG CCT GCG CCA AGT GCG CCT CCT CTG TGA CAA AGT GTC CGC TGT
T   A   P   S   T   I   R   H   S   C   H   A   V   M   Q   W   P   A   P   S   A   P   P   L   *   Q   S   V   R   C
1261/421                                    1291/431
GCC GGA AGC CCT TCA CCG ATG TGA TGC GCG TAT ATT TTT CTT AA
A   G   S   P   S   P   M   *   C   A   Y   I   F   L
```

FIG. 14B

```
1/1                                     31/11                                   61/21
ATG GCA TCT GTT GTA GCT GAT CTT CCG TCT TAT GGA CCT ATC GCT TTT GAT CAG GTG GAT AAC AAC ACG AAC GCG ACC CAG CTA TTC AAA
M   A   S   V   V   A   D   L   P   S   Y   G   P   I   A   F   D   Q   V   D   N   N   T   N   A   T   Q   L   F   K
91/31                                   121/41                                  151/51
AAT AAT ATA AAC AAA ACC AGA ATG AAC GAT TTA AAC CGC GAG GAG ACG CGA TTA AAA ACC TTC ACC GAC TGG CCG CTG GAT TGG CTG GAT
N   N   I   N   K   T   R   M   N   D   L   N   R   E   E   T   R   L   K   T   F   T   D   W   P   L   D   W   L   D
181/61                                  211/71                                  241/81
AAA CGC CAA TTG GCC CAA ACC GGC ATG TAC TTC ACA CAC GCC GGC GAC AAA GTT AAA TGC TTT TTC TGC GGC GTG GAA ATC GGT TGC TGG
K   R   Q   L   A   Q   T   G   M   Y   F   T   H   A   G   D   K   V   K   C   F   F   C   G   V   E   I   G   C   W
271/91                                  301/111                                 331/111
GAG CAG GAG GAT CAG CCC GTG CCG GAA CAT CAG CGA TGG TCG TCC AAC TGT CCA CTG TTG CGC CGG CGC ACT ACC AAC AAT GTG CCG ATC
E   Q   E   D   Q   P   V   P   E   H   Q   R   W   S   S   N   C   P   L   L   R   R   R   T   T   N   N   V   P   I
361/121                                 391/131                                 421/141
AAT GCC GAA GCA TTA GAT CGC ATC CTG CCG CCA ATA AGC TAC GAT ATC TGC GGC GCC AAC GAC TCG ACG CTG GAG ATG AGG GAG CAT GCC
N   A   E   A   L   D   R   I   L   P   P   I   S   Y   D   I   C   G   A   N   D   S   T   L   E   M   R   E   H   A
451/151                                 481/161                                 511/171
TAC GCA GAA GGC GTC ATA CCC ATG TCG CAG CTA ATT CAG TCG ATT GGC ATG AAT GCA GTA AAT GCG GCA GGC AGT GTA ACT GGG ACC GCA
Y   A   E   G   V   I   P   M   S   Q   L   I   Q   S   I   G   M   N   A   V   N   A   A   G   S   V   T   G   T   A
541/181                                 571/191                                 601/201
GCC CCG CAG CCG AGG GTA ACG GTC GCC ACC CAT GCG TCG ACG GCG ACA CAG GCC ACT GGC GAT GTC CAG CCG GAG ACG TGT CGT CCT TCA
A   P   Q   P   R   V   T   V   A   T   H   A   S   T   A   T   Q   A   T   G   D   V   Q   P   E   T   C   R   P   S
631/211                                 661/221                                 691/231
GCC GCC AGT GGC AAT TAT TTT CCC CAG TAT CCC GAA TAC GCC ATC GAG ACG GCA CGC CTG CGC ACC TTC GAG GCT TGG CCG AGG AAC CTG
A   A   S   G   N   Y   F   P   Q   Y   P   E   Y   A   I   E   T   A   R   L   R   T   F   E   A   W   P   R   N   L
```

FIG. 15A

```
721/241                                 751/251                                 781/261
AAA CAG AAG CCC CAC CAG CTG GCC GAG GCG GGT TTC TTC TAT ACA GGC GTT GGG GAT CGC GTC CGC TGC TTC AGT TGC GGC GGT GGT CTC
K   Q   K   P   H   Q   L   A   E   A   G   F   F   Y   T   G   V   G   D   R   V   R   C   F   S   C   G   G   G   L
811/271                                 841/281                                 871/291
ATG GAT TGG AAC GAC AAC GAC GAG CCC TGG GAA CAG CAC GCT CTC TGG CTA AGT CAG TGC CGA TTC GTC AAA CTG ATG AAG GGT CAG CTC
M   D   W   N   D   N   D   E   P   W   E   Q   H   A   L   W   L   S   Q   C   R   F   V   K   L   M   K   G   Q   L
901/301                                 931/311                                 961/321
TAT ATC GAT ACG GTG GCC GCC AAA CCA GTG CTG GCC GAG GAG AAG GAG GAG AGC TCT TCG ATT GGA GGG GAC GCG GTG GCC AGC ACA CAG
Y   I   D   T   V   A   A   K   P   V   L   A   E   E   K   E   E   S   S   S   I   G   G   D   A   V   A   S   T   Q
991/331                                 1021/341                                1051/351
GCT TCA GAG GAA GAG CAG CAG ACA TCA CTC TCA TCG GAG GAG GCC GTT TCG GGG GAT GTG GCT CCG TCC GTA GCT CCC ACG GCA GCC ACA
A   S   E   E   E   Q   Q   T   S   L   S   S   E   E   A   V   S   G   D   V   A   P   S   V   A   P   T   A   A   T
1081/361                                1111/371                                1141/381
CGC ATC TTC AAC AAG ATC GTC GAG GCG ACA GCG GTG GCT ACT CCC TCG ACA AAC AGC AGC GGC TCC ACC TCC ATA CCC GAG GAA AAG TTG
R   I   F   N   K   I   V   E   A   T   A   V   A   T   P   S   T   N   S   S   G   S   T   S   I   P   E   E   K   L
1171/391                                1201/401                                1231/411
TGC AAG ATC TGC TAC GGC GCC GAG TAC AAT ACG GCA TTC CTG CCA TGC GGT CAT GTG GTG GCC TGC GCC AAG TGC GCC TCC TCT GTG ACA
C   K   I   C   Y   G   A   E   Y   N   T   A   F   L   P   C   G   H   V   V   A   C   A   K   C   A   S   S   V   T
1261/421                                1291/431
AAG TGT CCG CTG TGC CGG AAG CCC TTC ACC GAT GTG ATG CGC GTA TAT TTT TCT TAA
K   C   P   L   C   R   K   P   F   T   D   V   M   R   V   Y   F   S   *
```

FIG. 15B

```
1/1                                        31/11                                      61/21
ATG GCA TCT GTT GTA GCT GAT CTT CCG TCT TAT GGA CCT ATC GCT TTT GAT CAG GTG GAT AAC AAC ACG AAC GCG ACC CAG CTA TTC AAA
M   A   S   V   V   A   D   L   P   S   Y   G   P   I   A   F   D   Q   V   D   N   N   T   N   A   T   Q   L   F   K
91/31                                      121/41                                     151/51
AAT AAT ATA AAC AAA ACC AGA ATG AAC GAT TTA AAC CGC GAG GAG ACG CGA TTA AAA ACC TTC ACC GAC TGG CCG CTG GAT TGG CTG GAT
N   N   I   N   K   T   R   M   N   D   L   N   R   E   E   T   R   L   K   T   F   T   D   W   P   L   D   W   L   D
181/61                                     211/71                                     241/81
AAA CGC CAA TTG GCC CAA ACC GGC ATG TAC TTC ACA CAC GCC GGC GAC AAA GTT AAA TGC TTT TTC TGC GGC GTG GAA ATC GGT TGC TGG
K   R   Q   L   A   Q   T   G   M   Y   F   T   H   A   G   D   K   V   K   C   F   F   C   G   V   E   I   G   C   W
271/91                                     301/111                                    331/111
GAG CAG GAG GAT CAG CCC GTG CCG GAA CAT CAG CGA TGG TCG CCC AAC TGT CCA CTG TTG CGC CGG CGC ACT ACC AAC AAT GTG CCG ATC
E   Q   E   D   Q   P   V   P   E   H   Q   R   W   S   P   N   C   P   L   L   R   R   R   T   T   N   N   V   P   I
361/121                                    391/131                                    421/141
AAT GCC GAA GCA TTA GAT CGC ATC CTG CCG CCA ATA AGC TAC GAT ATC TGC GGC GCC AAC GAC TCG ACG CTG GAG ATG AGG GAG CAT GCC
N   A   E   A   L   D   R   I   L   P   P   I   S   Y   D   I   C   G   A   N   D   S   T   L   E   M   R   E   H   A
451/151                                    481/161                                    511/171
TAC GCA GAA GGC GTC ATA CCC ATG TCG CAG CTA ATT CAG TCG ATT GGC ATG AAT GCA GTA AAT GCG GCA GGC AGT GTA ACT GGG ACC GCA
Y   A   E   G   V   I   P   M   S   Q   L   I   Q   S   I   G   M   N   A   V   N   A   A   G   S   V   T   G   T   A
541/181                                    571/191                                    601/201
GCC CCG CAG CCG AGG GTA ACG GTC GCC ACC CAT GCG TCG ACG GCG ACA CAG GCC ACT GGC GAT GTC CAG CCG GAG ACG TGT CGT CCT TCA
A   P   Q   P   R   V   T   V   A   T   H   A   S   T   A   T   Q   A   T   G   D   V   Q   P   E   T   C   R   P   S
631/211                                    661/221                                    691/231
GCC GCC AGT GGC AAT TAT TTT CCC CAG TAT CCC GAA TAC GCC ATC GAG ACG GCA CGC CTG CGC ACC TTC GAG GCT TGG CCG AGG AAC CTG
A   A   S   G   N   Y   F   P   Q   Y   P   E   Y   A   I   E   T   A   R   L   R   T   F   E   A   W   P   R   N   L
```

FIG. 16A

```
721/241                                                     751/251                                                     781/261
AAA CAG AAG CCC CAC CAG CTG GCC GAG GCG GGT TTC TTC TAT ACA GGC GTT GGG GAT CGC GTC CGC TGC TTC AGT TGC GGC GGT GGT CTC
K   Q   K   P   H   Q   L   A   E   A   G   F   F   Y   T   G   V   G   D   R   V   R   C   F   S   C   G   G   G   L
811/271                                                     841/281                                                     871/291
ATG GAT TGG AAC GAC AAC GAC GAG CCC TGG GAA CAG CAC GCT CTC TGG CTA AGT CAG TGC CGA TTC GTC AAA CTG ATG AAG GGT CAG CTC
M   D   W   N   D   N   D   E   P   W   E   Q   H   A   L   W   L   S   Q   C   R   F   V   K   L   M   K   G   Q   L
901/301                                                     931/311                                                     961/321
TAT ATC GAT ACG GTG GCC GCC AAA CCA GTG CTG GCC GAG GAG AAG GAG GAG AGC TCT TCG ATT GGA GGG GAC GCG GTG GCC AGC ACA CAG
Y   I   D   T   V   A   A   K   P   V   L   A   E   E   K   E   E   S   S   S   I   G   G   D   A   V   A   S   T   Q
991/331                                                     1021/341                                                    1051/351
GCT TCA GAG GAA GAG CAG CAG ACA TCA CTC TCA TCG GAG GAG GCC GTT TCG GGG GAT GTG GCT CCG TCC GTA GCT CCC ACG GCA GCC ACA
A   S   E   E   E   Q   Q   T   S   L   S   S   E   E   A   V   S   G   D   V   A   P   S   V   A   P   T   A   A   T
1081/361                                                    1111/371                                                    1141/381
CGC ATC TTC AAC AAG ATC GTC GAG GCG ACA GCG GTG GCT ACT CCC TCG ACA AAC AGC AGC GGC TCC ACC TCC ATA CCC GAG GAA AAG TTG
R   I   F   N   K   I   V   E   A   T   A   V   A   T   P   S   T   N   S   S   G   S   T   S   I   P   E   E   K   L
1171/391                                                    1201/401                                                    1231/411
TGC AAG ATC TGC TAC GGC GCC GAG TAC AAT ACG GCA TTC CTG CCA TGC GGT CAT GTG GTG GCC TGC GCC AAG TGC GCC TCC TCT GTG ACA
C   K   I   C   Y   G   A   E   Y   N   T   A   F   L   P   C   G   H   V   V   A   C   A   K   C   A   S   S   V   T
1261/421                                                    1291/431
AAG TGT CTG CTG TGC CGG AAG CCC TTC ACC GAT GTG ATG CGC GTA TAT TTT TCT TAA
K   C   L   L   C   R   K   P   F   T   D   V   M   R   V   Y   F   S   *
```

FIG. 16B

COMPOSITIONS AND METHODS FOR THE SCREENING OF COMPOUNDS TO ENHANCE OR REDUCE APOPTOSIS

This is a Continuation of copending application No. 60/137,624 filed on Jun. 4, 1999.

FIELD OF THE INVENTION

This invention generally relates to the nucleic acid sequences (and corresponding translated products) of novel mutant forms of the Drosophila DIAP1 gene and methods of identifying and testing agonists and antagonists of DIAP1 that enhance or reduce the apoptotic process.

BACKGROUND

Essentially all animal cells have the ability to activate an intrinsic cell suicide program, called programmed cell death (Steller, H. "Mechanisms and Genes of Cellular Suicide", *Science* 267:1445–1446, 1995; White E. "Life, death and the pursuit of apoptosis", *Genes Dev.* 10:1–15, 1996; Jacobson, M. D., et al. "Programmed Cell Death in Animal Development", *Cell* 88:347–354, 1997). The execution of this program leads to a morphologically distinct form of cell death termed apoptosis (Kerr et al. "Apoptosis: a basic biological phenomenon with wide ranging implications in tissue kinetics", *Br. J. Cancer* 26:239–257, 1972; Wyllie et al. "Cell Death: the significance of apoptosis", *Int. Rev. Cytol.*" 68:251–306, 1980). It is now generally accepted that apoptosis is of central importance for the development and homeostasis of metazoan animals. The roles of apoptosis include the sculpting of structures during development, deletion of unneeded cells and tissues, regulation of growth and cell number, and the elimination of abnormal and potentially dangerous cells. In this way, apoptosis provides a stringent and highly effective "quality control mechanism" that limits the accumulation of harmful cells, such as self-reactive lymphocytes, virus-infected cells and tumor cells (Reed "Regulation of apoptosis by bcl-2 family proteins and its role in cancer and chemoresistance", *Curr. Opin. Oncol* 7:541–546, 1995; Thompson "Apoptosis in the Pathogenesis and Treatment of Disease", *Science* 267:1456–1462, 1995; Naik et al. "The rise and fall of apoptosis during multistage tumorigenesis: down-modulation contributes to tumor progression from angiogenic progenitors" *Genes Dev.* 10:2105–2116, 1996; Morin et al. "Apoptosis and APC in colorectal tumorigenesis", *Proc. Natl. Acad. Sci.* USA 93:7950–7954, 1996; White "Life, death and the pursuit of apoptosis" *Genes Dev.* 10:1–15. 1996). On the other hand, inappropriate apoptosis is associated with a wide variety of diseases, including AIDS, neurodegenerative disorders, and ischemic stroke (Martinou et al. "Over-expression of Bcl-2 in transgenic mice protects neurons from naturally occurring cell death and experimental ischemia" *Neuron* 13:1017–1030, 1994; Thompson "Apoptosis in the Pathogenesis and Treatment of Disease", *Science* 267:1456–1462, 1995; Pettmann and Henderson "Neuronal Cell Death" *Neuron* 20:808–810, 1998).

Because it is now clear that apoptosis is the result of an active, gene-directed process, it should be possible to manipulate this form of death by developing drugs that interact with cell death proteins. Prior attempts at drug screening have been hampered by the lack of reagents that allow for the identification of compounds that interact with known regulatory constituents of the cell death mechanism. There is a pressing need for new reagents that help identify cell death agonistic or antagonistic compounds that act with specificity at known cell death modulating proteins. Knowing specifically where the compounds interact in the cell death pathway will allow for the modification of those compounds found to be agonistic or antagonistic thereby allow for the development of improved versions of the compound.

SUMMARY OF THE INVENTION

The present invention generally relates to compositions and methods of identifying and testing DIAP1 pathway agonists and antagonists. In addition, the invention relates to methods to identify other members of the DIAP1 signal pathway, methods to identify homologs of DIAP1 which are native to other tissue or cell types, methods to identify tissues that may harbor tumors expressing similar or homologous genes with simular mutations and methods to generate reagents derived from the invention.

The present invention contemplates employing novel mutant forms of the wild-type Drosophila DIAP1 gene (SEQ ID NO:1) in these screening methods. In one embodiment, the present invention contemplates generating chemically induced mutants that modulate the partial eye abolation phenotype of the GMRreaper and/or GMRHid of trangenic *Drosophila melanogaster*. In this way it is possible to screen for gof and lof mutations. In one embodiment, the present invention contemplates a composition comprising isolated and purified DNA having an oligonucleotide sequence selected from the group consisting of: DIAP1$^{6\text{-}3S}$ cDNA having the nucleotide sequence of SEQ ID NO: 2; DIAP1$^{45\text{-}2S}$ cDNA having the nucleotide sequence of SEQ ID NO: 3; DIAP1$^{23\text{-}4S}$ cDNA having the nucleotide sequence of SEQ ID NO: 4; DIAP1$^{11\text{-}3E}$ cDNA having the nucleotide sequence of SEQ ID NO: 5; DIAP1$^{22\text{-}8S}$ cDNA having the nucleotide sequence of SEQ ID NO: 6; DIAP1$^{21\text{-}4S}$ cDNA having the nucleotide sequence of SEQ ID NO: 7; DIAP1$^{33\text{-}1S}$ cDNA having the nucleotide sequence of SEQ ID NO: 8; DIAP1$^{21\text{-}2S}$ cDNA having the nucleotide sequence of SEQ ID NO: 9; DIAP1$^{41\text{-}8S}$ cDNA having the nucleotide sequence of SEQ ID NO: 10. Such DNA may readily be inserted into expression constructs and the present invention contemplates such constructs as well as their use. The present invention also contemplates RNA transcribed from the above-indicated cDNAs as well as protein (typically purified protein) translated from this RNA. Moreover, the present invention contemplates antibodies produced from immunizing with this translated protein.

The present invention also contemplates transgenic animals comprising the above-indicated DNA (i.e. the "transgene") or portions thereof. In a particular embodiment, the transgenic animal of the present invention may be generated with the transgene contained in an inducible, tissue specific promotor.

The present invention also contemplates using the above-named compositions in screening assays. The present invention is not limited by the particular method of screening. In one embodiment insect cells are used such as, but not limited to, Drosophila SL2 cells. In another embodiment mammalian cells may be used. The present invention is not limited to the nature of the transfection construct. The transfection constructs utilized will be the optimal constructs available for the cell line chosen at the time of setting up the assay. In one embodiment, the present invention contemplates screening suspected compounds in a system utilizing transfected cell lines. In one embodiment, the cells may be transfected transiently. In another embodiment, the cells may be stably transfected. In yet another embodiment translation products of the invention may be used in a cell-free assay system. In yet another embodiment, antibodies generated to the translation products of the invention may be used in immunoprecipitation assays.

The present invention may also be used to screen for tumors which manifest mutations in genes similar to, or homologous with, the cDNA encoding the invention. In, one embodiment cDNA encoding the invention may be used in microchip assays. The present invention contemplates a method of screening, comprising: a) providing in any order: i) a first solid support (e.g. microchip) comprising cDNA encoding at least a portion of the oligonucleotide sequence of SEQ ID NOS: 2, 3, 4, 5, 6, 7, 8, 9 or 10, ii) a second solid support (e.g. a second microchip) comprising at least a portion of the wild type Drosophila DAIP1 gene oligonucleotide sequence (SEQ ID NO:1), and iii) sample DNA from at least one tissue sample suspected of having mutations in genes similar to (or homologous with) SEQ ID NOS: 2, 3, 4, 5, 6, 7, 8, 9 or 10; b) contacting said first and second microassay microchips with said sample DNA under conditions such that hybridization can take place.

The present invention may also be used to identify new constituents of the DIAP1 signaling pathway. In one embodiment, antibodies generated to translation products of the invention may be used in immunoprecipitation experiments to isolate novel DIAP1 pathway constituents or natural mutations thereof. In another embodiment, the invention may be used to generate fusion proteins that could also be used to isolate novel DIAP1 pathway constituents or natural mutations thereof. In yet another embodiment screens may be conducted using the yeast two-hybrid system.

The present invention may also be used to identify new homologs of DIAP1 or natural mutations thereof. The present invention contemplates screening for homologs using standard molecular procedures. In one embodiment screens are conducted using Northern and Southern blotting.

The present invention contemplates a method of screening a compound, said method comprising: a) providing in any order: i) a first group of cells comprising a recombinant expression vector, wherein said vector comprises at least a portion of the oligonucleotide sequence of SEQ ID NOS: 2, 3, 4, 5, 6, 7, 8, 9 or 10, ii) a second group of cells comprising a recombinant expression vector, wherein said vector comprises at least a portion of the wild-type Drosophila DIAP1 gene oligonucleotide sequence (SEQ ID NO:1), and iii) at least one compound suspected of having the ability to modulate DIAP1 pathway activity; b) contacting said first and second groups of cells with said compound; and c) detecting programmed cell death modulation effects of said compound.

The present invention also contemplates a method of screening for homologs, said method comprising: a) providing in any order: i) first nucleic acid comprising at least a portion of the sequence of SEQ ID NOS: 2, 3, 4, 5, 6, 7, 8, 9 or 10, ii) second nucleic acid comprising at least a portion of the sequence of SEQ ID NO:1; and iii) DNA libraries from cells or tissues suspected to comprise said homolog; and b) hybridizing said first or second nucleic acid with said DNA of said library under conditions such that said DNA suspected of coding for said homolog is detected.

The present invention also contemplates a method of screening for interactive peptides, said method comprising: a) providing in any order: i) a peptide comprising at least a portion of the peptide sequence of SEQ ID NOS: 12, 13, 14, 15, 16, 17, 18, 19 or 20 (including but not limited to portions that are part of fusion proteins, i.e. proteins that contain another portion, such as a portion useful for protein purification) and b) an extract from source (e.g. cells or tissues) suspected of having said interactive peptides; and c) mixing said peptide with said extract under conditions such that said interactive peptide is detected.

The present invention contemplates another approach for screening for interactive peptides, said method comprising: a) providing in any order: i) antibodies reactive with (and usually specific for) at least a portion of a peptide having the sequence of SEQ ID NOS: 12, 13, 14, 15, 16, 17, 18, 19 or 20, and ii) an extract from a source (e.g. cells or tissues) suspected of having said interactive peptide(s); and b) mixing said antibody with said extract under conditions such that said interactive peptide is detected.

DESCRIPTION OF THE FIGURES

FIG. 7 shows the DNA sequence (diap$^{wt}$, SEQ ID NO:1) and peptide sequence (SEQ ID NO:11) of wild type DIAP1.

FIG. 8 shows the DNA sequence (SEQ ID NO:2) and peptide sequence (SEQ ID NO:12) of DIAP$^{6\text{-}3S}$.

FIG. 9 shows the DNA sequence (SEQ ID NO:3) and peptide sequence (SEQ ID NO:13) of DIAP$^{45\text{-}2S}$.

FIG. 10 shows the DNA sequence (SEQ ID NO:4) and peptide sequence (SEQ ID NO:14) of DIAP$^{23\text{-}4S}$.

FIG. 11 shows the DNA sequence (SEQ ID NO:5) and peptide sequence (SEQ ID NO:15) of DIAP$^{22\text{-}8S}$.

FIG. 12 shows the DNA sequence (SEQ ID NO:6) and peptide sequence (SEQ ID NO:16) of DIAP$^{22\text{-}8S}$.

FIG. 13 shows the DNA sequence (SEQ ID NO:7) and peptide sequence (SEQ ID NO: 17) of DIAP$^{21\text{-}4S}$.

FIG. 14 shows the DNA sequence (SEQ ID NO:8) and peptide sequence (SEQ ID NO:18) of DIAP$^{33\text{-}1S}$.

FIG. 15 shows the DNA sequence (SEQ ID NO:9) and peptide sequence (SEQ ID NO:19) of DIAP$^{21\text{-}2S}$.

FIG. 16 shows the DNA sequence (SEQ ID NO:10) and peptide sequence (SEQ ID NO:20) of DIAP$^{41\text{-}8S}$.

DEFINITIONS

Figure 1:
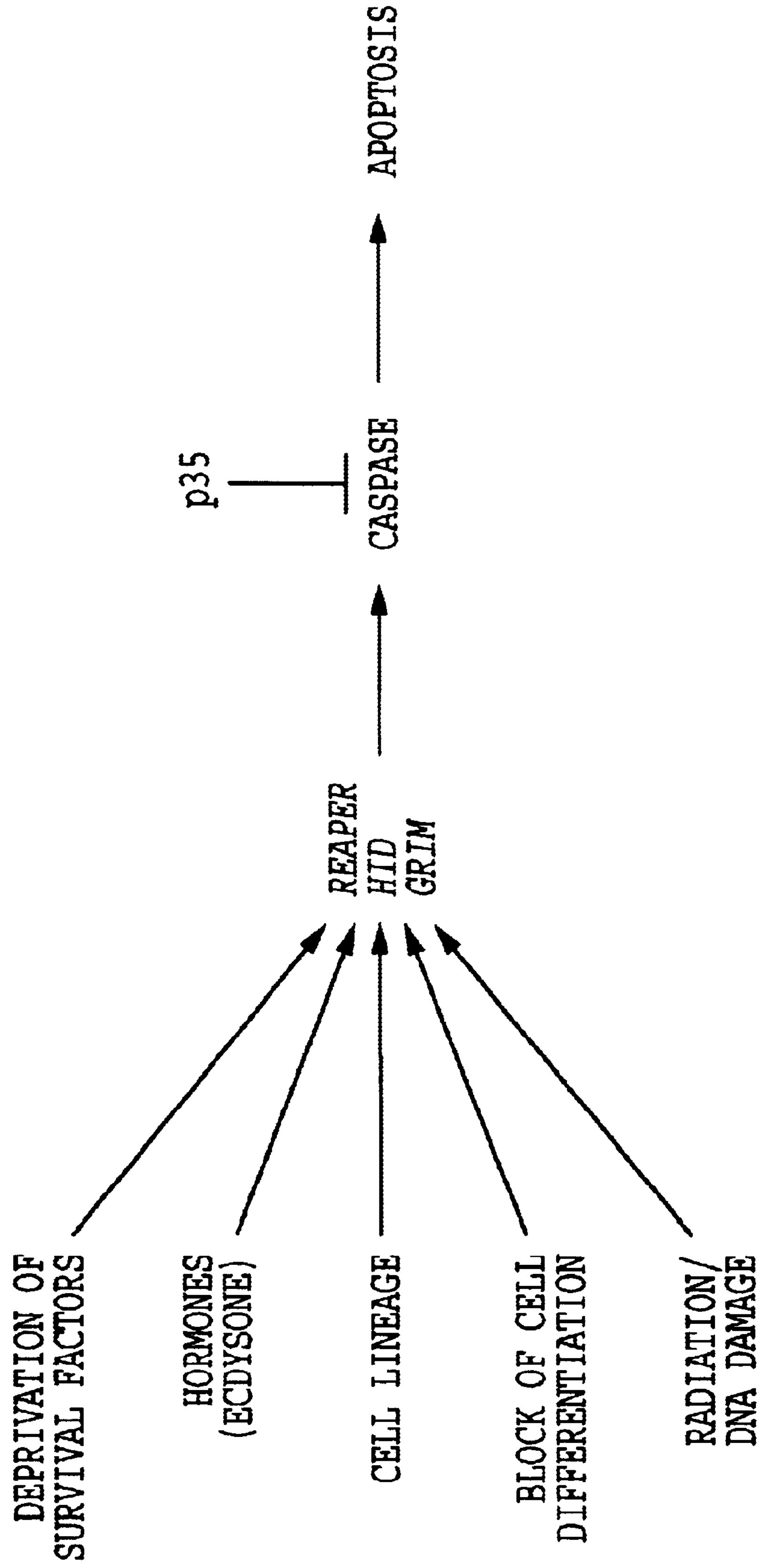
FIG. 1 shows a model for the integration of different death-inducing signals in Drosophila.

To facilitate understanding of the invention, a number of terms are defined below. The term "gene" refers to a DNA sequence that comprises control and coding sequences necessary for the production of a polypeptide or its precursor. The polypeptide can be encoded by a full length coding sequence or by any portion of the coding sequence.

The term "nucleic acid sequence of interest" refers to any nucleic acid sequence the manipulation of which may be deemed desirable for any reason by one of ordinary skill in the art.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

As used herein, the terms "vector" and "vehicle" are used interchangeably in reference to nucleic acid molecules that transfer DNA segment(s) from one cell to another.

The term "expression construct", "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "hybridization" as used herein refers to any process by which a strand of nucleic acid joins with a complementary strand through base pairing.

As used herein, the terms "complementary" or "complementarity" when used in reference to polynucleotides refer to polynucleotides which are related by the base-pairing rules. For example, for the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target. The present invention contemplates hybridization (in the various assays described above) at both low and high stringency conditions.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

As used herein, the term "fusion protein" refers to a chimeric protein containing the protein of interest (i.e., DIAP1 and fragments thereof) joined to an exogenous protein fragment (the fusion partner which consists of a non-DIAP1 sequence). The fusion partner may provide a detectable moiety, may provide an affinity tag to allow purification of the recombinant fusion protein from the host cell, or both. If desired, the fusion protein may be removed from the protein of interest by a variety of enzymatic or chemical means known to the art. The present invention contemplates such fusion proteins in some of the assays described above.

As used herein, the term "purified" or "to purify" refers to the removal of contaminants from a sample. The present invention contemplates purified compositions (discussed above).

As used herein the term "portion" when in reference to a protein (as in "a portion of a given protein") refers to fragments of that protein. The fragments may range in size from four amino acid residues to the entire amino acid sequence minus one amino acid. When used in reference to nucleic acid, a "portion" may range in size from approximately 12–100 bases and more preferably approximately 15–70 bases.

The term "DIAP1" shall refer to Drosophila inhibitor of apoptosis protein 1, a Drosophila homolog of the mammalian inhibitor of apoptosis proteins (IAPs).

The term "apoptosis" is understood by those in the art to refer to the morphological changes that are observed in a cell as the cell undergoes a non-accidental death.

The term "programmed cell death" as used herein is defined as the term to describe the genetically controlled process that is executed in a cell that has been induced to undergo apoptosis. The phrase "programmed cell death modulation effects" means the alteration of the normal course of events associated with programmed cell death as a result of an external influence (e.g. transfection of a gene into the cell) on the cell.

The phrase "gain-of-function" (gof) as used herein is applicable to the situation where a modified oligonucleotide that, when transfected into a host organism and translated into a peptide, results in a peptide that will function with increased efficiency (e.g. rate of reaction, affinity, etc.) as compared to the wild type peptide. For example, the modified oligonucleotide (or "gof nucleotide") may, in effect, function as an augmenter of the natural gene if the natural gene is present and functional in the host into which the gof oligonucleotide was transfected, or it may add that function to the host if the natural gene is not present or is non-functional.

The phrase "loss-of-function" (lof) as used herein is applicable to the situation where a modified oligonucleotide, when transfected into a host organism and translated into a peptide, results in a peptide that function with decreased efficiency (e.g. rate of reaction, affinity, etc.) as compared to the wild type peptide. For example, the modified oligonucleotide (or "lof" oligonucleotide") may, in effect, function as a diminisher of natural gene function if the natural gene is present and functional in the host into which the lof oligonucleotide was transfected, or may negatively interfere with processes in the host if the natural gene is not present or is non-functional.

"Antibody" shall be defined as a glycoprotein produced by B cells that binds with high specificity to the agent (usually, but not always, a peptide), or a structurally similar agent, that generated its production. Antibodies may be produced by any of the known methodologies (reference) and may be either polyclonal or monoclonal.

"Mutant" shall be defined as any changes made to a wild type nucleotide sequence, either naturally or artificially, that produces a translation product that functions with enhanced or decreased efficiency in at least one of a number of ways including, but not limited to, specificity for various interactive molecules, rate of reaction and longevity of the mutant molecule.

"Staining" shall be defined as any number of processes known to those in the field that are used to better visualize a specific component(s) and/or feature(s) of a cell or cells.

"TUNEL" shall be defined as terminal deoxynucleotidyl transferase (TdT)-mediated FITC-dUTP nick end labeling, a technique to quantitate apoptosis known to those in the field.

"Morphology" shall be defined as the visual appearance of a cell or organism when viewed with the eye, a light microscope or eletronmicroscope, as appropriate.

"Blebbing", in relation to cell morphology, shall be described as a ruffled appearance of the cell surface when the cell is viewed by either light or electron microscopy.

GENERAL DESCRIPTION OF THE INVENTION

The present invention pertains to the screening of compounds for agonistic or antagonistic affects on apoptosis, particularly with compounds that exert their effect at the level of IAPs. The present invention also pertains to the development of drug therapies, the screening for DIAP interactive proteins and the screening of DIAP intra- and interspecific homologs.

A. Modulation of Apoptosis via IAPs

IAPs have recently emerged as important regulators of cells death. IAPs were originally discovered in baculovirus strains by their ability to functionally substitute for (baculovirus)-p35 in blocking apoptosis (Crook et al. "An apoptosis-inhibiting baculovirus gene with a zinc finger-like motif" *J. Virol.* 67:2168–2174, 1994; Birnbaum et al. "An apoptosis-inhibiting gene from nuclear polyhedrosis virus encoding a polypeptide with Cys/His sequence motifs" *J. Virol.* 68:2521–2528, 1994; Clem and Miller "Control of programmed cell death by the baculocirus genes p35 and iap" *Mol. Cell. Biol.* 14:5212–5222, 1994). Subsequently a number of related genes were discovered in Drosophila and mammals (Roth et al. "The TNFR2-TRAF signaling conplex contains two novel proteins related to baculovirus inhibitor of apoptosis proteins" *Cell* 83:1243–1252, 1995; Liston et al. "Suppression of apoptosis in mammalian cells by NAIP and a related family of IAP genes" *Nature* 379:349–353, 1996; Uren et al. "Cloning and expression of apoptosis inhibitory protein homologs that function to inhibit apoptosis and/or bind tumor necrosis factor receptor-associated factors" *Proc. Natl. Acad. Sci* U.S.A. 93:4974–4978, 1996; Ambrosini et al. "A novel anti-apoptosis gene, survivin, expressed in cancer and lymphoma" *Nat. Med.* 3:917–921, 1997). IAPs share several structural motifs: they contain at least one and usually two or three tandem baculovirus IAP repeat (BIR) motifs, and most have a carboxy-terminal RING finger domain. Several, but not all IAPs have been shown to inhibit apoptosis. For example, loss of DIAP1 function leads to the enhancement of reaper/hid mediated cell death (Hay et al. "Drosophila homologs of baculocirus inhibitor of apoptosis proteins function to block cell death" *Cell* 83:1253–1262, 1995). Furthermore, loss-of-function (lof) mutations in diap1, one of the two known Drosophila IAPs, enhance reaper, grim and hid-induced cell death. The overexpression of diap1 and gain-of-function (gof) mutations suppress apoptosis in insect cells (Uren et al. "Cloning and expression of apoptosis inhibitory protein homologs that function to inhibit apoptosis and/or bind tumor necrosis factor receptor-associated factors" *Proc. Natl. Acad. Sci* U.S.A. 93:4974–4978, 1996; Vucic et al., "Inhibition of Reaper-inducded apoptosis by interaction with inhibitor of apoptosis proteins (IAPs)" *Proc. Nat. Acad. Sci.* U.S.A. 94:10183–10188, 1997; Vucic et al., "IAPs physically interact with and block apoptosis induced by Drosophila proteins HID and GRIM" *Mol. Cell Biol.* 18:3300–3309, 1998). Gof mutations have been shown to be the result of a single amino acid change in the BIR domain. Both baculovirus and Drosophila IAPs physically interact with REAPER and HID (Vucic et al., "Inhibition of Reaper-inducded apoptosis by interaction with inhibitor of apoptosis proteins (IAPs)" *Proc. Nat. Acad. Sci.* U.S.A. 94:10183–10188, 1997; Vucic et al., "IAPs physically interact with and block apoptosis induced by Drosophila proteins HID and GRIM" *Mol. Cell Biol.* 18:3300–3309, 1998).

B. IAPs as a Reagent for Drug Screens

Several human IAP homologs have been discovered. Ectopic expression of human IAP genes can suppress apoptosis in several systems (Duckett et al. "A conserved family of cellular genes related to the baculovirus iap gene and encoding apoptosis inhibitors" *EMBO J.* 15:2685–2694, 1996; Liston et al. "Suppression of apoptosis in mammalian cells by NAIP and a related family of IAP genes" *Nature* 379:349–353, 1996; Uren et al. "Cloning and expression of apoptosis inhibitory protein homologs that function to inhibit apoptosis and/or bind tumor necrosis factor receptor-associated factors" *Proc. Natl. Acad. Sci* U.S.A. 93:4974–4978, 1996; Ambrosini et al. "A novel anti-apoptosis gene, survivin, expressed in cancer and lymphoma" *Nat. Med.* 3:917–921, 1997; Chu et al. "Suppression of tumor necrosis factor-induced cell death by inhibitor of apoptosis c-IAP2 is under NF-kappaB control" *Proc. Nat. Acad. Sci.* U.S.A. 94:10057–62, 1997; Devereaux et al. "X-linked IAP is a direct inhibitor of cell-death proteases" *Nature* 388:300–304, 1997), and the expression of survivin, a human IAP homolog, correlates with oncogenic transformation (Ambrosini et al. "A novel anti-apoptosis gene, survivin, expressed in cancer and lymphoma" *Nat. Med.* 3:917–921, 1997). Additionally, mutations in NIAP, another human IAP gene, are thought to contribute to spinal muscular atrophy (SMA) which involves inappropriate neuronal apoptosis (Roy et al., "The gene for neuronal apoptosis inhibitory protein is partially deleted in individuals with spinal muscular atropy" *Cell* 80:167–178, 1995). The present invention consists of 9 naturally occurring mutations of the diap1 gene and includes both lof and gof varieties. As such, these mutants can be employed in screens for compound which modulate the mutants abilities to inhibit or augment the apoptotic process. Since both gof and lof mutants are available, the invention will make it possible to determine if a compound modulates cell death at the level of the IAPs or up stream in the IAP pathway. This is because modulators of apoptosis that are nonspecific for IAPs or the pathway upstream of IAPs would not be affected by either mutation.

C. Mutant DIAP1s as Reagents for the Screening of Tumors

One of the most pressing problems associated with present day technology in the treatment of tumors is the nonspecificity of treatment (e.g. chemotherapy and radiation). To develop tumor specific treatments, it may be necessary to identify the specific gene mutation that causes the tumor. Currently, there are few reagents for the identification of specific gene mutations in tumor cells. This invention would allow for the screening of tumors containing mutations in genes similar to, or homologous with, the gene mutations encoded in the invention. The identification of tumors expressing such gene mutations may allow for the development of specific treatments for those tumors.

D. Mutant DIAP1s as Reagents for the Identification of Interactive Proteins

The availability of novel, mutant Drosophila diap1 genes make it possible to screen for DIAP1 interactive proteins that bind preferentially to DIAP1 when in the active or nonactive state. Such interactive proteins hitherto would have been difficult to isolate since it would not have been possible to ensure that DIAP1 could be maintained in an active or nonactive state providing the quantities necessary to assure for reasonable success.

E. Mutant DIAP1s as Reagents for the Identification of Homologs

The availability of novel, mutant Drosophila diap1 genes make it possible to screen for unique, naturally occurring gof or lof DIAP1 homologs. The invention will allow for screening techniques directed towards finding mutations suspected of functioning as natural regulators of apoptosis.

F. IAPs as a Target for Drug and Gene Therapies

Currently, there are few regents available for the design of assays suitable for measuring the affect of compounds suspected of modulating specific components of the apoptotic pathway. The discovery of mutant DIAP1 genes provide reagents for an assay that can be used to identify compounds that specifically interact at or upstream of DIAP1 modulation of apoptosis. Since aberrant apoptosis has been identified as a component in numerous diseases such as neurodegenerative diseases, cancer, autoimmune diseases and AIDS, the ability to identify compounds specific for a known regulatory point in the apoptotic process will allow for the development of compounds with varying therapeutic specificity and potency.

With regard to gene therapy, it is contemplated that gene targeting resulting in the mutation, deletion or replacement of particular IAP proteins can be used to treat certain diseases. In diseases where the rate of apoptosis is affected by naturally mutated iap genes, it may be possible to restore the ability of these cells to live or die. For example, eye sight has been restored to otherwise blind flies by inhibiting apoptosis in cells destined to die as the result of a neurodegenerative disease (Davidson and Steller, "Blocking Apoptosis Prevents Blindness in Drosophila Retinal Degeneration Mutants", *Nature* 33\91:587–591, 1998).

DETAILED DESCRIPTION OF PREFERRED EMBODIMENTS

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references [See, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y.].

Oligonucleotides can be synthesized on an Applied Bio-Systems oligonucleotide synthesizer [for details see Sinha et al., Nucleic Acids Res. 12:4539 (1984)], according to specifications provided by the manufacturer. Complementary oligonucleotides are annealed by heating them to 90° C. in a solution of 10 mM Tris-HCl buffer (pH 8.0) containing NaCl (200 mM) and then allowing them to cool slowly to room temperature. For binding and turnover assays, duplex DNA is purified from native polyacrylamide (15% w/v) gels. The band corresponding to double-stranded DNA is excised and soaked overnight in 0.30 M sodium acetate buffer (pH 5.0) containing EDTA (1 mM). After soaking, the supernatant is extracted with phenol/chloroform (1/1 v/v) and precipitated with ethanol. DNA substrates are radiolabeled on their 5'-OH group by treatment with [g-$^{32}$P]ATP and T4 polynucleotide kinase. Salts and unincorporated nucleotides are removed by chromatography on Sephadex G columns.

The present invention contemplates assays for detecting the ability of agents to inhibit or enhance DIAP1-mediated modulation of apoptosis where high-throughput screening formats are employed together with large agent banks (e.g., compound libraries, peptide libraries, and the like) to identify antagonists or agonists. Such DIAP1 pathway antagonists and agonists may be further developed as potential therapeutics and diagnostic or prognostic tools for diverse types of cancers, autoimmune diseases and hereditary diseases.

1. Screens to Identify Agonists of Antagonists of DIAP1

There are several different approaches contemplated by the present invention to look for small molecules that specifically inhibit or enhance the ability of the various DIAP1 mutants to modulate apoptosis. One approach is to transfect expression constructs comprising nucleic acid encoding the DIAP1 mutants into cells and measure changes in the rate of apoptosis as compared to controls after the cells have been exposed to the compound suspected of modulating mediating DIAP1 activity. Cells may be transiently transfected or stably transfected with the construct under control of an inducible promoter. Other embodiments would include translation of the invention and purification of the peptide. The purified peptide could then be used to test specific compound:protein interactions. Additionally, it is possible to generate antibodies to the translated invention allowing for the development of immunological assays such as, but not limited to, RIA, ELISA or Western blot. Furthermore, transgenic animal could be produced allowing for in vivo assays to be conducted.

A. In vitro Assays a. Transfection Assays

Transfection assays allow for a great deal of flexibility in assay development. The wide range of commercially available transfection vectors will permit the expression of the DIAP1 mutants of the present invention in a extensive number of cell types. Additionally, DIAP1 has been shown to initiate apoptosis in insect cells and in mammalian HeLa cells. In one embodiment, cells are transiently transfected with an expression construct comprising nucleic acid encoding DIAP1 mutants of the present invention that included an inducible promotor allowing for the initiation of translation and transcription when needed. Cells are exposed to the agent suspected of modulating DIAP1 activity, DIAP1 expression is turned on and apoptosis is measured. Rates of apoptosis in cells expressing the invention are compared to rates of apoptosis in cells transfected with a construct expressing a wild type diap1 gene and cells expressing a control expression vector (e.g. an empty expression vector). Rates of apoptosis can be quantitated by any of a number of ways reported in the literature and known to those practiced in the art.

In another embodiment, stably transfected cells lines are developed, i.e. cell lines stably expressing the DIAP1 mutants of the present invention. The use of an inducible promoter would be utilized in these systems. Screening assays for compounds suspected of modulating DIAP1 activity are conducted in the same manner as with the transient transfection assays. Using stably transfected cell lines allows for greater consistency between experiments and allows for inter-experimental comparisons.

B. In Vivo Assays a. Transgenic Animal Assays

In one embodiment transgenic animals will be constructed using standard protocols (see example 5). The generation of transgenic animals will allow for the investigation of diseases for which the mutated forms of DIAP1 may provide the means for determining the physiology of the disease or its treatment.

2. Screen to Identify Tumors Expressing Similar or Homologous Gene Mutations

In one embodiment tumor screens will be constructed using solid supports such as microassay microchip techniques. This will allow for the development of a high-through-put screen for the identification of tumors expressing mutant genes similar to, or homologous with, the mutated Drosophila DIAP1 genes.

3. Screens to Identify DIAP1 Signal Pathway Constituents

A. In vitro Assays

There are several different approaches to identifying DIAP1 interactive molecules. The invention would allow the identification of proteins that may only associated with nonactive (or reduced activity) DIAP1 or constitutively active DIAP1 molecules. Such proteins may regulate DIAP1 function. Techniques that may be used are, but not limited to, immunoprecipitation of DIAP1 with antibodies generated to the transcription product of the invention. This would also bring down any associated bound proteins. Another method is to generate fusion proteins containing the mutant form of DIAP1 connected to a generally recognized pull-down protein such as glutathione S-transferase. Bound proteins can then be eluded and analyzed.

a. Immunoprecipitation

After the generation of antibodies to wild type and mutant DIAP1, cells expressing transfected DIAP1 are lysed and then incubated with one of the antibodies. Antibodies with the bound DIAP1 and any associated proteins can then be pulled down with protein-A Sepharose or protein-G Sepharose beads, using standard techniques.

b. Fusion Protein Pull-down

A method similar to immunoprecipitation is to construct fusion proteins of the mutant and wild type DIAP1 and glutathione S-transferase (GST). The DIAP1 fusion proteins are then incubated with cell extracts and then removed with glutathione Sepharose beads. Any bound, DIAP1 proteins are then characterized.

B. In Vivo Assays a. Yeast Two-hybrid System

The yeast two-hybrid system that identifies the interaction between two proteins by reconstructing active transcription factor dimers. The dimers are formed between two fusion proteins, one of which contains a DNA-binding domain (DB) fused to the first protein of interest (DB-X) and the other, an activation domain (AD) fused to the second protein of interest (AD-Y). The DB-X:AD-Y interaction reconstitutes a functional transcription factor that activates chromosomally-integrated reporter genes driven by promoters containing the relevant DB binding sites. Large cDNA libraries can be easily screened with the yeast-two hybrid system. Yeast cDNA libraries are commercially available. Standard molecular biological techniques can be employed to isolate and characterize the interacting protein.

Screens to Identify Hid Homologs

Standard molecular biological techniques can be used to identify DIAP1 homologs in Drosophila or other species. For example, the present invention contemplates a variety of approaches including, but are not limited to, DNA-DNA hybridization techniques (e.g. Southern blots) and DNA-RNA hybridization techniques (e.g. Northern blots). Additional techniques may include, for example, immunoscreening of proteins made from library stocks with antibodies generated to translation products of SEQ ID NOS: 2, 3, 4, 5, 6, 7, 8, 9 or 10. Futhermore, immunoprecipitation of known or suspected interactive proteins of DIAP1 can be followed by the indentification of possible mutant DIAP1 homologs with antibodies generated to translation products of SEQ ID NOS: 2, 3, 4, 5, 6, 7, 8, 9 or 10.

Experimental

EXAMPLE 1

Drosophila as a Model for Cell Death

This example details the establishment of Drosophila as a model system for the study of apoptosis. Previous studies of apoptosis in insects had almost exclusively focused on cell death during metamorphosis (Truman et al. "Programmed neuronal death in insect development" *J. Neurobiol.* 23:1295–1311, 1992). While that work has provided many important insights, including some of the first evidence that programmed cell death is an active process (Lockshin "Programmed cell death. Activation of lysis mechanism by a mechanism involving the aynthesis of protein" *J. Insect Physiol.* 15:1505–1516, 1969), no systematic efforts to identify cell death defective mutants have been reported. During the last few years, Drosophila has been established as one of the prime model systems for investigating the control and mechanism of apoptotic cell death (Hengartner "Programmed cell death in invertebrates" *Curr. Opinion Genetics Devel.* 6:34–38, 1996, Jacobson et al. "Programmed cell death in animal development" *Cell* 88:347–354, 1997). We screened a large fraction of the Drosophila genome for genes that are required for apoptotic cell death. Our goal was to identify mutants that were globally defective in cell death, since such a phenotype would be consistent with the inactivation of genes that function downstream of the signaling pathways regulating apoptosis. We chose to focus on cell death in the Drosophila embryo, since this stage appeared particularly amenable to genetic analysis, and since we did not want to assume that a cell death defective mutant would reach advanced development stages. Thw present inventors begun by describing the morphology and pattern of cell death as it normally occurs during embryogenesis, and by adopting protocols for the quick and reliable detection of apoptotic cell in embryos (Abrams et al. "Programmed cell death during Drosophila embryogenesis" *Developement* 117:29–43, 1993). Next, we examined the pattern of cell death in embryos homozygous for previously identified chromosomal deletions (White et al. "Genetic control of cell death in Drosophila" *Science* 264:677–683, 1994). From this screen, one region (75C1,2) was found to be essential for virtually all cell deaths that normally occur during embryogenesis. In addition, these deletion mutant embryos were also protected against the ectopic cell deaths that are normally induced in developmental mutants or following irradiation. Significantly, the morphology and kinetics of the few cell deaths observed under these circumstances was indistinguishable from that seen in wild type. This suggested that the 75C1,2 region was specifically required for the activation, but not for the execution of the cell death program.

EXAMPLE 2

Reaper, Hid and Grim Encode Important Apoptotic Activators

This example details the establishment of reaper, hid and grim as death regulatory genes in Drosophila. The molecular characterization of the 75C1,2 interval led to the identification of three genes that play a central role in the activation of apoptosis in Drosophila (White et al. "Genetic control of cell death in Drosophila" *Science* 264:677–683, 1994; Grether et al. "The head involution defective gene of *Drosophila melanogaster* functions in programmed cell death" *Genes & Development* 9:1694–1708, 1995; Chen et al. "grim, a novel cell death gene in Drosophila" *Genes Dev.* 10:1773–1782, 1996). All three genes are contained with in a 300 kb interval that is deleted by Df(3L)H99 (abbreviated H99), the smallest cell death-defective deletion in this region. All three genes encode novel proteins of 65 amino acids (REAPER), 138 amino acids (GRIM) and 410 amino acids (HID). REAPER has some weak homology to the mammalian "death domain" of the type-1 tumor necrosis factor receptor (TNFR1) and Fas, but the significance of this is not yet clear (Golstein et al. "Homology between Reaper and the cell death domains of Fas and TNFR1" *Cell* 81:185–186, 1995). Interestingly, like the "death domain", REAPER, protein has strong self-aggregation properties in vitro. This suggests that the active form of REAPER, like TNFR1 and Fas, may be a multimer. Careful examination of the deduced protein sequences of REAPER, HID and GRIM revealed a small region of similarity at the N-terminus (Grether et al. "The head involution defective gene of *Drosophila melanogaster* functions in programmed cell death" *Genes & Development* 9:1694–1708, 1995; Chen et al. "grim, a novel cell death gene in Drosophila" *Genes Dev.* 10:1773–1782, 1996). As discussed in more detail below, this N-terminal region can physically interact with a domain of baculovirus IAP proteins (Vucic et al. "Inhibition of Reaper-induced apoptosis by interaction with inhibitor of apoptosis proteins (IAPs)" *Proc. Nat. Acad. Sci. U.S.A.* 94:10183–10188, 1997; Vucic et al. "IAPs physically interact with and block apoptosis induced by Drosophila proteins HID and GRIM" *Mol. Cell Biol.* 18:3300–3309, 1998). Several of the experiments described in specific aim 1 are designed to test the functional significance of the physical association of HID, GRIM and REAPER with IAPs.

Unlike any other cell death gene identified to date, reaper is specifically expressed in cells that are doomed to die, anticipating death by several hours (White et al. "Genetic control of cell death in Drosophila" *Science* 264:677–683, 1994; Robinow et al. "Genes that induce apoptosis: transcriptional regulation in identified, doomed neurons of the Drosophila CNS" *Dev. Biol.* 190:206–213, 1997). The expression of this gene is also induced in response to a variety of other death-inducing stimuli, including X-irradiation, block of cellular differentiation and steroid hormone regulated deaths (Nordstrom et al. "Activation of the reaper gene defines an essential function required for both naturally-occuring apoptosis and induced cell killing in Drosophila" *Dev. Biol.* 180:227–241, 1996; Robinow et al. "Genes that induce apoptosis: transcriptional regulation in identified, doomed neurons of the Drosophila CNS" *Dev. Biol.* 190:206–213, 1997; Lamblin and Steller "Integration of apoptotic stimuli by the Drosophila cell death gene reaper" in preparation, 1998). This indicates that the integration of different death inducing signals occurs, at least in part, by a transcriptional mechanism (see below). Furthermore, since the apoptotic program appears to be expressed in both live and dying cells, reaper can not be part of such a program. Consistent with our earlier hypothesis, it rather appears that reaper, hid and grim encode apoptotic activators that link many different signaling pathways with the death program. FIG. 1 shows a schematic that illustrates the integration of apoptotic stimuli at the level of reaper, hid and grim translation and activation.

EXAMPLE 3

Integration of Different Death Signals Occurs by a Transcriptional Mechanism

This example details the establishment of reaper as an integrator of apoptosic death signaling. A fundamental unresolved question in apoptosis research is how distinct death-inducing stimuli converge to activate a common apoptotic program. Our finding that reaper is specifically expressed in doomed cells suggested that this convergence may occur via a transcriptional mechanism. In order to examine this possibility further, we have initiated studies on the reaper promotor (Nordstrom et al. "Activation of the reaper gene defines an essential function required for both naturally-occuring apoptosis and induced cell killing in Drosophila" *Dev. Biol.* 180:227–241, 1996; Lamblin and Steller "Integration of apoptotic stimuli by the Drosophila cell death gene reaper" in preparation, 1998). Using lacZ reporter constructs, we found that the transcription of reaper is sensitive to diverse death-inducing signals. Furthermore, we have defined specific regions in the upstream control region of reaper that are required for the transcriptional activation in response to distinct signals, such as ionizing radiation and steroid hormone regulation (Lamblin and Steller "Integration of apoptotic stimuli by the Drosophila cell death gene reaper" in preparation, 1998). These results indicate that diverse signals converge upon discrete reaper-associated transcriptional control elements to initiate a common apoptotic pathway (FIG. 1). The detailed characteristics of these regulatory elements and associated transcription factors offers many exciting opportunities to define signaling pathways that regulate apoptosis, and this is a major goal of our HHMI-sponsored work.

EXAMPLE 4

Cell Killing by Reaper, Hid and Grim

Figure 2:
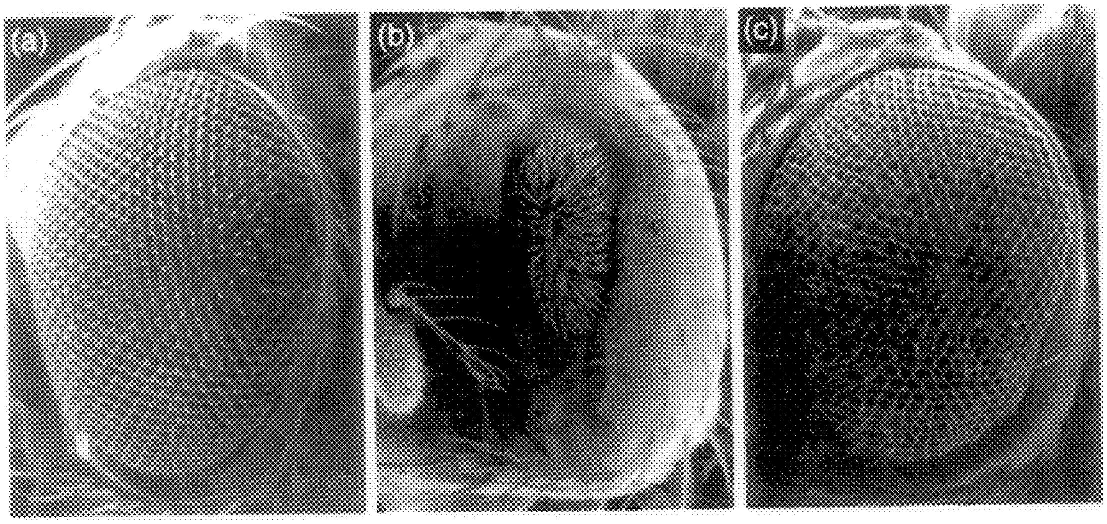
FIGS. 2(*a*), (*b*), (*c*) shows that hid-directed eye ablation requires caspase activity.

This example details the establishment of reaper, hid and grim expression in the induction of caspase regulated apoptotic death. The ectopic expression of either reaper, hid and grim induces apoptosis in cultured cells, and in many different cell types of transgenic animals (Grether et al. "The head involution defective gene of *Drosophila melanogaster* functions in programmed cell death" *Genes & Development* 9:1694–1708, 1995; White et al. "Genetic control of cell death in Drosophila" *Science* 264:677–683, 1994; Pronk et al. "Requirement of an ICE-like protease for induction of apoptosis and ceramide generation by REAPER" *Science* 271:808–810, 1996; Chen et al. "grim, a novel cell death gene in Drosophila" *Genes Dev.* 10:1773–1782, 1996; Zhou et al. "Cooperative functions of the reaper and head involotion defective genes in programmed celll death of Drosophila CNS midline cells" *Proc. Nat. Acad. Sci. U.S.A.* 94:5131–5136, 1997, McNabb et al. "Disruption of a behavioral sequence by targeted death of peptidergic neurons in Drosophila" *Neuron* 19:813–823, 1998). Particular useful approach has been the expression of cell death genes in the Drosophila compound eye. Expression of either reaper, hid and grim under the control of an eye specific promotor (GMR) induces apoptosis that results in eye ablation (White et al. "Genetic control of cell death in Drosophila" *Science* 264:677–683, 1994; Grether et al. "The head involution defective gene of *Drosophila melanogaster* functions in programmed cell death" *Genes & Development* 9:1694–1708, 1995; Chen et al. "grim, a novel cell death gene in Drosophila" *Genes Dev.* 10:1773–1782, 1996). The induction of apoptosis depends critically on gene dosage. At intermediate levels of expression, a reduced, rough eye phenotype is obtained. Significantly, coexpression of the anti-apoptotic baculovirus protein p35 completely suppresses these phenotypes and allows for essentially normal ommatidial differentiation. (White et al. "Genetic control of cell death in Drosophila" *Science* 264:677–683, 1994; Grether et al. "The head involution defective gene of *Drosophila melanogaster* functions in programmed cell death" *Genes & Development* 9:1694–1708, 1995; Chen et al. "grim, a novel cell death gene in Drosophila" *Genes Dev.* 10:1773–1782, 1996). FIG. 2 shows that eye ectopic hid-mediated eye ablation can be rescued by expression of the caspase inhibitor p35. Panel (a) is the control, panel (b) shows the effect of hid expression alone and panel (c) shows the effect of hid and p35 coexpression. Because p35 specifically inhibits cysteine proteases (Bumb et al. "Inhibition of ICE family proteases by baculovirus antiapoptotic protein p35" *Science* 269:1885–1888, 1995; Xue and Horvitz "Inhibition of the Caenorhabditis elegans cell-death protease CED-3 by a CED-3 cleavage site in baculovirus p35 protein" *Nature* 377:248–251, 1995), this result suggests that reaper, hid and grim kill by activating a caspase pathway (see FIG. 1). As explained in more detail below, the eye phenotypes caused by the ectopic expression of these genes provide an exquisitely sensitive and rapid assay for the identifying mutants in other cell death genes.

Figure 3:
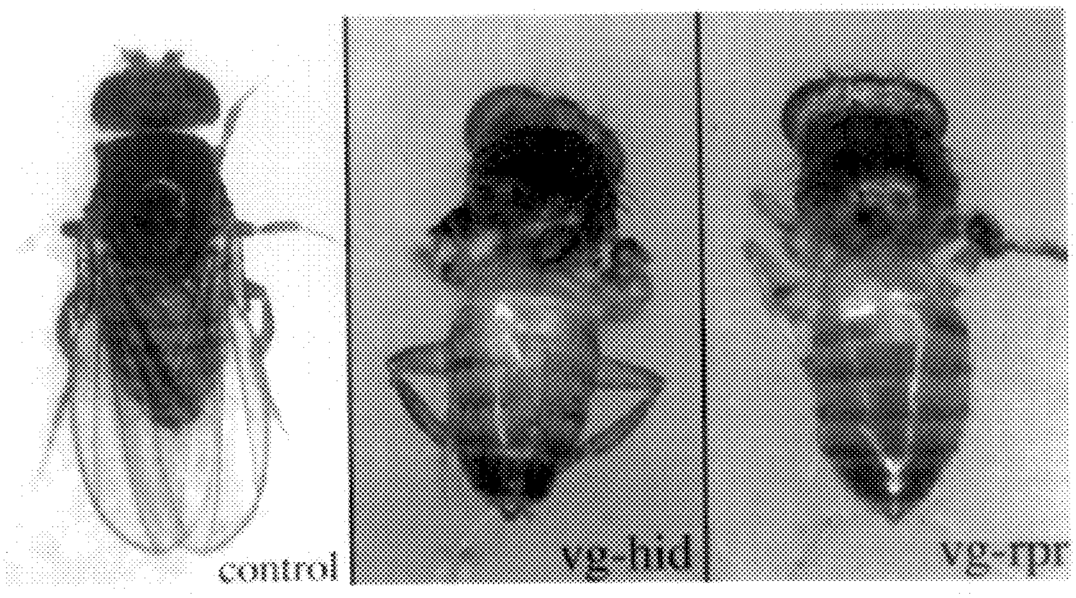
FIG. 3 shows wing ablation targeted by hid and reaper.

We have also generated Drosophila strains that are transgenic for UAS (upstream activating sequences)-reaper and UAS-hid constructs (Zhou et al. "Cooperative functions of the reaper and head involotion defective genes in programmed celll death of Drosophila CNS midline cells" *Proc. Nat. Acad. Sci. U.S.A.* 94:5131–5136, 1997, McNabb et al. "Disruption of a behavioral sequence by targeted death of peptidergic neurons in Drosophila" *Neuron* 19:813–823, 1998). These strains readily permit the expression of either reaper or hid in many different cells and tissues via the yeast Gal4 system (Brand and Perrimon "Targeting gene expression as a means of altering cell fates and generating dominant phenotypes" *Development* 118:401–415, 1993). For example, expression of reaper or hid in the developing wing causes complete wing ablation. FIG. 3 shows the effect of targeted reaper and hid expression on wing development in Drosophila. The left hand panel is the control, the middle panel is a hid transfectant and the right hand panel is a reaper trasnfectant. Many other tissues and cell types have been successfully ablated, but the efficiency of ablation caries between different cell types. The basis for these differences is not really understood, but it appears that survival signaling pathways, in particular MAP-kinase activity, can have a profound effect on cell killing. In any event, the ability to use many different transcriptional control elements to induced apoptosis in different cell types to establish trangenic animals and in transfected cultured cells is very useful for the study of apoptosis in numerous systems.

EXAMPLE 5

Genetic Screens for Novel Cell Death Genes

Figure 4:
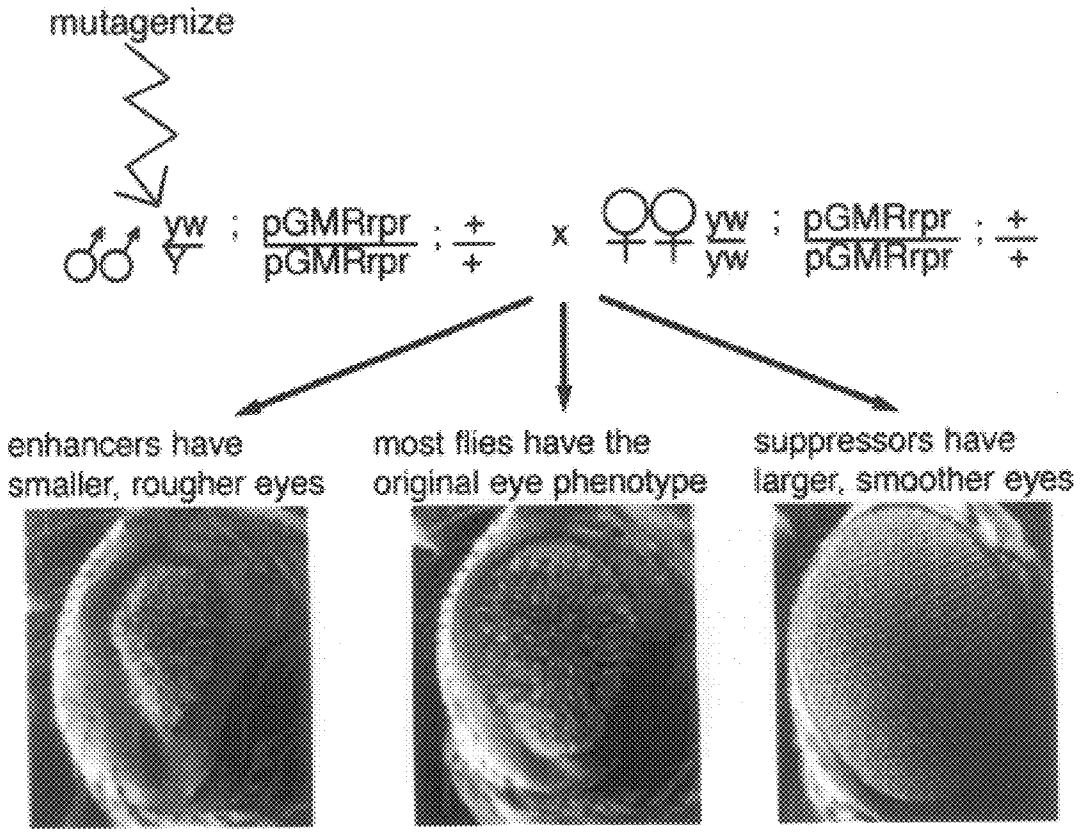
FIG. 4 shows the methodology used to isolate cell death modifiers.

This example details the discovery of the new diap1 cell death regulatory gene mutants. One of the major advantages for using Drosophila as a system for apoptosis research is the ability to employ the powerful genetic methods available in this organism for identifying new cell death genes. When expressed under the control of the eye-specific GMR promoter, reaper, hid and grim cause cell death, resulting in eye ablation (see FIG. 2; Grether et al. "The head involution defective gene of *Drosophila melanogaster* functions in programmed cell death" *Genes & Development* 9:1694–1708, 1995; White et al. "Genetic control of cell death in Drosophila" *Science* 264:677–683, 1994; Chen et al. "grim, a novel cell death gene in Drosophila" *Genes Dev.* 10:1773–1782, 1996). These eye phenotypes depend on transgene dosage, so that at intermediate levels of expression reduced and roughened eyes are obtained. Under conditions of partial eye ablation, cells are highly sensitive to alterations in the dosage of cell death genes acting downstream of reaper, hid and grim. This permits very simple and efficient F1 screens for genetic modifiers of reaper, hid and grim mediated cell killing: mutations that promote apoptosis can be identified as enhancers of eye defects, while mutations that inhibit death suppress this phenotype. FIG. 4 diagrams the methods used to isolate cell death modifier genes. Mutaginized males from a GMR-reaper transgenic strain were crossed to females of the same strain. The F1 progeny of these crosses were screened for flies with different eye morphology than the staring strain. Since the Drosophila eye is a nonessential and easily visible tissue, it is possible to screen large numbers of mutagenized flies and isolate not only inactivating alleles, but also rare gof mutations in cell death genes. Because mutants are recovered as heterozygotes in F1 screens, mutations that are homozygous lethal or sterile can be readily recovered.

Figure 5:
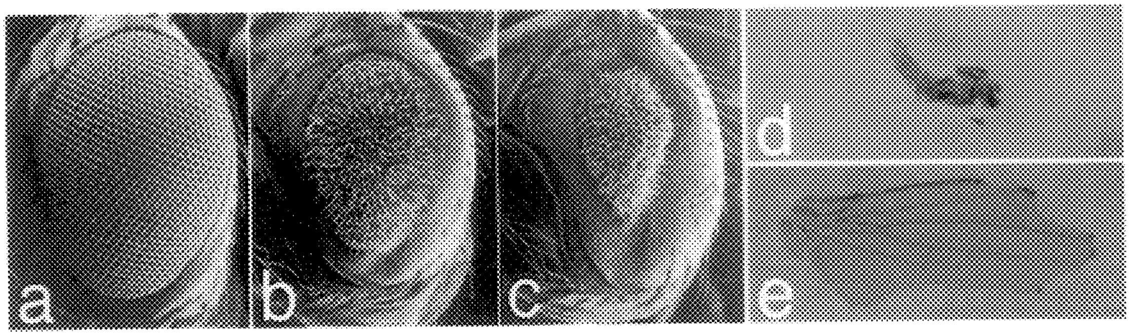
FIGS. 5(*a*), (*b*), (*c*) shows the effect of lof and gof DIAP1 mutations on cell death.

Initially we screened a collection of chromosomal deletions representing collectively approximately 65% of the genome. From this survey, we identified 10 regions that significantly modified GMRrpr and/or GMRhid. These deletions were later used to map recessive phenotypes associated with chemically induced modifier mutants (see below). Interestingly, we identified deletions that modified only the GMRrpr, only the GMRhid, or both, suggesting that there are common components of the reaper and hid pathways, and components unique to each. Next, we performed several chemical mutagenesis screens using either ENU or EMS as the mutagen. We embarked on large scale chemical mutagenesis because we expected that chemical mutagenesis would provide us with gof (increase in apoptotic function achieved through either activating inducers of apoptosis or through the inhibition of negative (i.e. dominant-negative) regulators of apoptosis) alleles of cell death genes, in addition to lof mutants. Many cell death genes may be part of a gene family (such as Bcl-2, IAPs and caspases) with partially redundant functions. A 50% reduction of the products of such genes (i.e. heterozygosity) may not be detectable in our F1 screen if other family members contribute similar functions. On the other hand, gof mutations that increase activity, or dominant-negative alleles may produce robust changes in our assay. As descussed in more detail below, we have indeed recovered many interesting gof alleles. From screening approximately 500,000 flies, more than 250 cell death modifier mutations were isolated. These modifiers were subject to a number of assays designed to test their specificity. First, in order to eliminate mutants affecting eye developement or expression of the transgene from the GMR promoter, we tested whether modifiers affected the eye phenotype of GMRphylopod (Chang et al. "phyllopod functions in the fate determination of a subset of photoreceptor death in rd, rds and rhodopsin mutant mice" *Cell* 80:463–472, 1995). Ectopic expression of this developmental gene from the GMR promoter alters cell fate and causes a rough-eye phenotype that is dosage sensitive, but largely independent of apoptosis. Therefore, mutations that affect apoptosis should not significantly modify this phenotype. The second type of screen tested whether our modifiers could affect cell death phenotype caused by expressing reaper, hid and grim from different promoters in other tissues, such as the embryo or wing (see FIG. 3). FIG. 5 shows the effect of lof and gof mutations in DIAP1 on the Drosophila eye ablation phenetype (a, GMR-hid/6-3S gof mutation inhibits the eye ablation phenotype; b, GMR-hid/+ control; c, GMR-hid/+; 11-3e/+ lof mutation enhances the eye ablation phenotype). Mutations in genes with a deletion screen demonstrated that some modifiers could be specific for GMRrpr or GMRhid, we tested the ability of all of our mutants to modify reaper, hid and grim.

Figure 6:
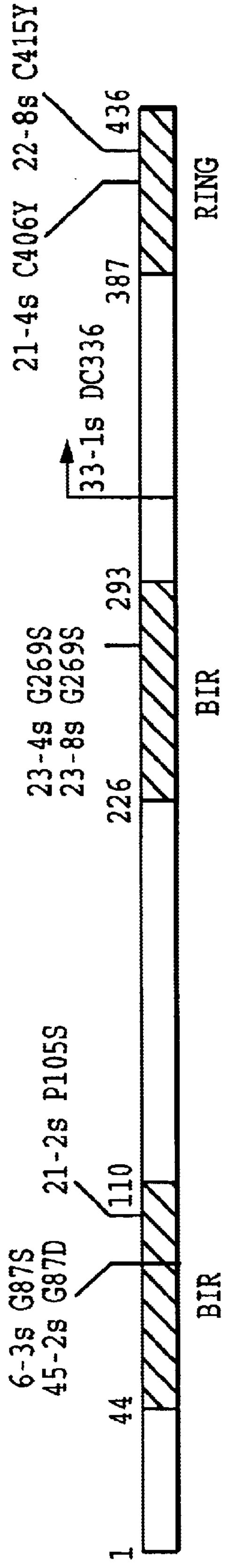
FIG. 6 shows the molecular changes associated with DIAP1 alleles and a schematic representation of where these mutations are located on the DIAP1 protein.

These analyses revealed an interesting group of mutations that, by all of our criteria, are likely to be involved in apoptosis. Many of these mutations were recombinant mapped and, where appropriate, recessive phenotypes associated with these mutants were also mapped against deletions (Greenspan "Fly pushing: The theory and practice of Drosophila genetics" Clod Spring Harbor Laboratory Press, New York, 1997). Of particular interest to this application are the mutations in thread, which encodes a Drosophila IAP gene, DIAP1. FIG. 6 shows the molecular changes associated with DIAP1 alleles. Genomic DNA of 9 different DIAP1 alleles was isolated from homozygous embryos, amplified by PCR, and multiple samples for each allele were directly sequenced. The consequence of the nucleotide changes associated with these mutations and their genetic properties are noted in the table. Also shown is a schematic representation of where these mutations are located in the DIAP1 protein.

What is claimed is:

1. A composition comprising isolated and purified DNA having the sequence of SEQ ID NO:2.

2. An isolated RNA transcribed from the DNA of claim 1.

3. Expression constructs comprising DNA of claim 1.

* * * * *

SEQUENCE LISTING

```
<160> NUMBER OF SEQ ID NOS: 20

<210> SEQ ID NO 1
<211> LENGTH: 1317
<212> TYPE: DNA
<213> ORGANISM: Drosophila melanogaster

<400> SEQUENCE: 1

atggcatctg ttgtagctga tcttccgtct tatggaccta tcgcttttga tcaggtggat      60

aacaacacga acgcgaccca gctattcaaa aataatataa acaaaaccag aatgaacgat     120

ttaaaccgcg aggagacgcg attaaagacc ttcaccgact ggccgctaga ttggctggat     180
```

-continued aaacgccaat tggcccaaac cggcatgtac ttcacacacg ccggcgacaa agttaaatgc 240
tttttctgcg gcgtggaaat cggttgctgg gagcaggagg atcagcccgt gccggaacat 300
cagcgatggt cgcccaactg tccactgttg cgccggcgca ctaccaacaa tgtgccgatc 360
aatgccgaag cattagatcg catcctgccg ccaataagct acgatatctg cggcgccaac 420
gactcgacgc tagagatgag ggagcacgcc tacgcagaag gcgtcatacc catgtcgcag 480
ctaattcagt cgattggcat gaatgcagta aatgcggcag gcagtgtaac tggaaccgca 540
gccccgcagc cgagggtaac ggtcgccacc catgcctcga cggcgacaca ggccactggc 600
gatgtccagc cggagacgtg tcgtccttca gccgccagtg gcaattattt tccccagtat 660
cccgaatacg ccatcgagac ggcacgcctg cgcaccttcg aggcttggcc gaggaacctg 720
aaacagaagc cccaccagct ggccgaggcg ggtttcttct atacaggcgt tggggatcgc 780
gtccgctgct tcagttgcgg cggtggtctc atggattgga acgacaacga cgagccctgg 840
gaacagcacg ctctctggct aagtcagtgc cgattcgtca agctgatgaa gggtcagctc 900
tatatcgata cggtggccgc caaaccagtg ctggccgagg agaaggagga gagcacttcg 960
attggagggg acacggtggc cagcacacag gcttcagagg aagagcagca gacatcactc 1020
tcatcggagg aggccgtttc gggggatgtg gctccgtccg tagctcccac ggcagccaca 1080
cgcatcttca acaagatcgt cgaggcgaca gcggtggcta ctccctcgac aaacagcagc 1140
ggctccacct ccatacccga ggaaaagttg tgcaagatct gctacggcgc cgagtacaat 1200
acggcattcc tgccatgcgg tcatgtggtg gcctgcgcca agtgcgcctc ctctgtgaca 1260
aagtgtccgc tgtgccggaa gcccttcacc gatgtgatgc gcgtatattt ttcttaa 1317

<210> SEQ ID NO 2
<211> LENGTH: 1317
<212> TYPE: DNA
<213> ORGANISM: Drosophila melanogaster

<400> SEQUENCE: 2
atggcatctg ttgtagctga tcttccgtct tatggaccta tcgcttttga tcaggtggat 60
aacaacacga acgcgaccca gctattcaaa aataatataa acaaaaccag aatgaacgat 120
ttaaaccgcg aggagacgcg attaaagacc ttcaccgact ggccgctaga ttggctggat 180
aaacgccaat tggcccaaac cggcatgtac ttcacacacg ccggcgacaa agttaaatgc 240
tttttctgcg gcgtggaaat cagttgctgg gagcaggagg atcagcccgt gccggaacat 300
cagcgatggt cgcccaactg tccactgttg cgccggcgca ctaccaacaa tgtgccgatc 360
aatgccgaag cattagatcg catcctgccg ccaataagct acgatatctg cggcgccaac 420
gactcgacgc tagagatgag ggagcacgcc tacgcagaag gcgtcatacc catgtcgcag 480
ctaattcagt cgattggcat gaatgcagta aatgcggcag gcagtgtaac tggaaccgca 540
gccccgcagc cgagggtaac ggtcgccacc catgcctcga cggcgacaca ggccactggc 600
gatgtccagc cggagacgtg tcgtccttca gccgccagtg gcaattattt tccccagtat 660
cccgaatacg ccatcgagac ggcacgcctg cgcaccttcg aggcttggcc gaggaacctg 720
aaacagaagc cccaccagct ggccgaggcg ggtttcttct atacaggcgt tggggatcgc 780
gtccgctgct tcagttgcgg cggtggtctc atggattgga acgacaacga cgagccctgg 840
gaacagcacg ctctctggct aagtcagtgc cgattcgtca agctgatgaa gggtcagctc 900
tatatcgata cggtggccgc caaaccagtg ctggccgagg agaaggagga gagcacttcg 960

-continued

```
attggagggg acacggtggc cagcacacag gcttcagagg aagagcagca gacatcactc   1020

tcatcggagg aggccgtttc gggggatgtg gctccgtccg tagctcccac ggcagccaca   1080

cgcatcttca acaagatcgt cgaggcgaca gcggtggcta ctccctcgac aaacagcagc   1140

ggctccacct ccatacccga ggaaaagttg tgcaagatct gctacggcgc cgagtacaat   1200

acggcattcc tgccatgcgg tcatgtggtg gcctgcgcca agtgcgcctc ctctgtgaca   1260

aagtgtccgc tgtgccggaa gcccttcacc gatgtgatgc gcgtatattt ttcttaa      1317
```

```
<210> SEQ ID NO 3
<211> LENGTH: 1317
<212> TYPE: DNA
<213> ORGANISM: Drosophila melanogaster

<400> SEQUENCE: 3

atggcatctg ttgtagctga tcttccgtct tatggaccta tcgcttttga tcaggtggat     60

aacaacacga acgcgaccca gctattcaaa aataatataa acaaaaccag aatgaacgat    120

ttaaaccgcg aggagacgcg attaaagacc ttcaccgact ggccgctaga ttggctggat    180

aaacgccaat tggcccaaac cggcatgtac ttcacacacg ccggcgacaa agttaaatgc    240

tttttctgcg gcgtggaaat cgattgctgg gagcaggagg atcagcccgt gccggaacat    300

cagcgatggt cgcccaactg tccactgttg cgccggcgca ctaccaacaa tgtgccgatc    360

aatgccgaag cattagatcg catcctgccg ccaataagct acgatatctg cggcgccaac    420

gactcgacgc tagagatgag ggagcacgcc tacgcagaag gcgtcatacc catgtcgcag    480

ctaattcagt cgattggcat gaatgcagta aatgcggcag gcagtgtaac tggaaccgca    540

gccccgcagc cgagggtaac ggtcgccacc catgcctcga cggcgacaca ggccactggc    600

gatgtccagc cggagacgtg tcgtccttca gccgccagtg gcaattattt tccccagtat    660

cccgaatacg ccatcgagac ggcacgcctg cgcaccttcg aggcttggcc gaggaacctg    720

aaacagaagc cccaccagct ggccgaggcg ggtttcttct atacaggcgt tggggatcgc    780

gtccgctgct tcagttgcgg cggtggtctc atggattgga acgacaacga cgagccctgg    840

gaacagcacg ctctctggct aagtcagtgc cgattcgtca agctgatgaa gggtcagctc    900

tatatcgata cggtggccgc caaaccagtg ctggccgagg agaaggagga gagcacttcg    960

attggagggg acacggtggc cagcacacag gcttcagagg aagagcagca gacatcactc   1020

tcatcggagg aggccgtttc gggggatgtg gctccgtccg tagctcccac ggcagccaca   1080

cgcatcttca acaagatcgt cgaggcgaca gcggtggcta ctccctcgac aaacagcagc   1140

ggctccacct ccatacccga ggaaaagttg tgcaagatct gctacggcgc cgagtacaat   1200

acggcattcc tgccatgcgg tcatgtggtg gcctgcgcca agtgcgcctc ctctgtgaca   1260

aagtgtccgc tgtgccggaa gcccttcacc gatgtgatgc gcgtatattt ttcttaa      1317
```

```
<210> SEQ ID NO 4
<211> LENGTH: 1317
<212> TYPE: DNA
<213> ORGANISM: Drosophila melanogaster

<400> SEQUENCE: 4

atggcatctg ttgtagctga tcttccgtct tatggaccta tcgcttttga tcaggtggat     60

aacaacacga acgcgaccca gctattcaaa aataatataa acaaaaccag aatgaacgat    120

ttaaaccgcg aggagacgcg attaaagacc ttcaccgact ggccgctaga ttggctggat    180

aaacgccaat tggcccaaac cggcatgtac ttcacacacg ccggcgacaa agttaaatgc    240
```

-continued

```
tttttctgcg gcgtggaaat cggttgctgg gagcaggagg atcagcccgt gccggaacat    300
cagcgatggt cgcccaactg tccactgttg cgccggcgca ctaccaacaa tgtgccgatc    360
aatgccgaag cattagatcg catcctgccg ccaataagct acgatatctg cggcgccaac    420
gactcgacgc tagagatgag ggagcacgcc tacgcagaag gcgtcatacc catgtcgcag    480
ctaattcagt cgattggcat gaatgcagta aatgcggcag gcagtgtaac tggaaccgca    540
gccccgcagc cgagggtaac ggtcgccacc catgcctcga cggcgacaca ggccactggc    600
gatgtccagc cggagacgtg tcgtccttca gccgccagtg gcaattattt tccccagtat    660
cccgaatacg ccatcgagac ggcacgcctg cgcaccttcg aggcttggcc gaggaacctg    720
aaacagaagc cccaccagct ggccgaggcg ggtttcttct atacaggcgt tggggatcgc    780
gtccgctgct tcagttgcgg cggtagtctc atggattgga acgacaacga cgagccctgg    840
gaacagcacg ctctctggct aagtcagtgc cgattcgtca agctgatgaa gggtcagctc    900
tatatcgata cggtggccgc caaaccagtg ctggccgagg agaaggagga gagcacttcg    960
attggagggg acacggtggc cagcacacag gcttcagagg aagagcagca gacatcactc   1020
tcatcggagg aggccgtttc gggggatgtg gctccgtccg tagctcccac ggcagccaca   1080
cgcatcttca acaagatcgt cgaggcgaca gcggtggcta ctccctcgac aaacagcagc   1140
ggctccacct ccatacccga ggaaaagttg tgcaagatct gctacggcgc cgagtacaat   1200
acggcattcc tgccatgcgg tcatgtggtg gcctgcgcca agtgcgcctc ctctgtgaca   1260
aagtgtccgc tgtgccggaa gcccttcacc gatgtgatgc gcgtatattt ttcttaa      1317
```

<210> SEQ ID NO 5
<211> LENGTH: 1317
<212> TYPE: DNA
<213> ORGANISM: Drosophila melanogaster

<400> SEQUENCE: 5

```
atggcatctg ttgtagctga tcttccgtct tatggaccta tcgcttttga tcaggtggat     60
aacaacacga acgcgaccca gctattcaaa aataatataa acaaaaccag aatgaacgat    120
ttaaaccgcg aggagacgcg attaaagacc ttcaccgact ggccgctaga ttggctggat    180
aaacgccaat tggcccaaac cggcatgtac ttcacacacg ccggcgacaa agttaaatgc    240
tttttctgcg gcgtggaaat cggttgctgg gagcaggagg atcagcccgt gccggaacat    300
cagcgatggt cgcccaactg tccactgttg cgccggcgca ctaccaacaa agtgccgatc    360
aatgccgaag cattagatcg catcctgccg ccaataagct acgatatctg cggcgccaac    420
gactcgacgc tagagatgag ggagcacgcc tacgcagaag gcgtcatacc catgtcgcag    480
ctaattcagt cgattggcat gaatgcagta aatgcggcag gcagtgtaac tggaaccgca    540
gccccgcagc cgagggtaac ggtcgccacc catgcctcga cggcgacaca ggccactggc    600
gatgtccagc cggagacgtg tcgtccttca gccgccagtg gcaattattt tccccagtat    660
cccgaatacg ccatcgagac ggcacgcctg cgcaccttcg aggcttggcc gaggaacctg    720
aaacagaagc cccaccagct ggccgaggcg ggtttcttct atacaggcgt tggggatcgc    780
gtccgctgct tcagttgcgg cggtggtctc atggattgga acgacaacga cgagccctgg    840
gaacagcacg ctctctggct aagtcagtgc cgattcgtca agctgatgaa gggtcagctc    900
tatatcgata cggtggccgc caaaccagtg ctggccgagg agaaggagga gagcacttcg    960
attggagggg acacggtggc cagcacacag gcttcagagg aagagcagca gacatcactc   1020
```

-continued

```
tcatcggagg aggccgtttc gggggatgtg gctccgtccg tagctcccac ggcagccaca   1080

cgcatcttca acaagatcgt cgaggcgaca gcggtggcta ctccctcgac aaacagcagc   1140

ggctccacct ccatacccga ggaaaagttg tgcaagatct gctacggcgc cgagtacaat   1200

acggcattcc tgccatgcgg tcatgtggtg gcctgcgcca agtgcgcctc ctctgtgaca   1260

aagtgtccgc tgtgccggaa gcccttcacc gatgtgatgc gcgtatattt ttcttaa      1317
```

<210> SEQ ID NO 6
<211> LENGTH: 1317
<212> TYPE: DNA
<213> ORGANISM: Drosophila melanogaster

<400> SEQUENCE: 6

```
atggcatctg ttgtagctga tcttccgtct tatggaccta tcgcttttga tcaggtggat     60

aacaacacga acgcgaccca gctattcaaa aataatataa acaaaaccag aatgaacgat    120

ttaaaccgcg aggagacgcg attaaagacc ttcaccgact ggccgctaga ttggctggat    180

aaacgccaat tggcccaaac cggcatgtac ttcacacacg ccggcgacaa agttaaatgc    240

tttttctgcg gcgtggaaat cggttgctgg gagcaggagg atcagcccgt gccggaacat    300

cagcgatggt cgcccaactg tccactgttg cgccggcgca ctaccaacaa tgtgccgatc    360

aatgccgaag cattagatcg catcctgccg ccaataagct acgatatctg cggcgccaac    420

gactcgacgc tagagatgag ggagcacgcc tacgcagaag gcgtcatacc catgtcgcag    480

ctaattcagt cgattggcat gaatgcagta aatgcggcag gcagtgtaac tggaaccgca    540

gccccgcagc cgagggtaac ggtcgccacc catgcctcga cggcgacaca ggccactggc    600

gatgtccagc cggagacgtg tcgtccttca gccgccagtg gcaattattt tccccagtat    660

cccgaatacg ccatcgagac ggcacgcctg cgcaccttcg aggcttggcc gaggaacctg    720

aaacagaagc cccaccagct ggccgaggcg ggtttcttct atacaggcgt tggggatcgc    780

gtccgctgct tcagttgcgg cggtggtctc atggattgga acgacaacga cgagccctgg    840

gaacagcacg ctctctggct aagtcagtgc cgattcgtca agctgatgaa gggtcagctc    900

tatatcgata cggtggccgc caaaccagtg ctggccgagg agaaggagga gagcacttcg    960

attggagggg acacggtggc cagcacacag gcttcagagg aagagcagca gacatcactc   1020

tcatcggagg aggccgtttc gggggatgtg gctccgtccg tagctcccac ggcagccaca   1080

cgcatcttca acaagatcgt cgaggcgaca gcggtggcta ctccctcgac aaacagcagc   1140

ggctccacct ccatacccga ggaaaagttg tgcaagatct gctacggcgc cgagtacaat   1200

acggcattcc tgccatgcgg tcatgtggtg gcctgcgcca agtacgcctc ctctgtgaca   1260

aagtgtccgc tgtgccggaa gcccttcacc gatgtgatgc gcgtatattt ttcttaa      1317
```

<210> SEQ ID NO 7
<211> LENGTH: 1317
<212> TYPE: DNA
<213> ORGANISM: Drosophila melanogaster

<400> SEQUENCE: 7

```
atggcatctg ttgtagctga tcttccgtct tatggaccta tcgcttttga tcaggtggat     60

aacaacacga acgcgaccca gctattcaaa aataatataa acaaaaccag aatgaacgat    120

ttaaaccgcg aggagacgcg attaaagacc ttcaccgact ggccgctaga ttggctggat    180

aaacgccaat tggcccaaac cggcatgtac ttcacacacg ccggcgacaa agttaaatgc    240

tttttctgcg gcgtggaaat cggttgctgg gagcaggagg atcagcccgt gccggaacat    300
```

-continued

```
cagcgatggt cgcccaactg tccactgttg cgccggcgca ctaccaacaa tgtgccgatc    360

aatgccgaag cattagatcg catcctgccg ccaataagct acgatatctg cggcgccaac    420

gactcgacgc tagagatgag ggagcacgcc tacgcagaag gcgtcatacc catgtcgcag    480

ctaattcagt cgattggcat gaatgcagta aatgcggcag gcagtgtaac tggaaccgca    540

gccccgcagc cgagggtaac ggtcgccacc catgcctcga cggcgacaca ggccactggc    600

gatgtccagc cggagacgtg tcgtccttca gccgccagtg gcaattattt tccccagtat    660

cccgaatacg ccatcgagac ggcacgcctg cgcaccttcg aggcttggcc gaggaacctg    720

aaacagaagc cccaccagct ggccgaggcg ggtttcttct atacaggcgt tggggatcgc    780

gtccgctgct tcagttgcgg cggtggtctc atggattgga acgacaacga cgagccctgg    840

gaacagcacg ctctctggct aagtcagtgc cgattcgtca agctgatgaa gggtcagctc    900

tatatcgata cggtggccgc caaaccagtg ctggccgagg agaaggagga gagcacttcg    960

attggagggg acacggtggc cagcacacag gcttcagagg aagagcagca gacatcactc   1020

tcatcggagg aggccgtttc gggggatgtg gctccgtccg tagctcccac ggcagccaca   1080

cgcatcttca acaagatcgt cgaggcgaca gcggtggcta ctccctcgac aaacagcagc   1140

ggctccacct ccatacccga ggaaaagttg tgcaagatct gctacggcgc cgagtacaat   1200

acggcattcc tgccatacgg tcatgtggtg gcctgcgcca agtgcgcctc ctctgtgaca   1260

aagtgtccgc tgtgccggaa gcccttcacc gatgtgatgc gcgtatattt ttcttaa      1317
```

<210> SEQ ID NO 8
<211> LENGTH: 1304
<212> TYPE: DNA
<213> ORGANISM: Drosophila melanogaster

<400> SEQUENCE: 8

```
atggcatctg ttgtagctga tcttccgtct tatggaccta tcgcttttga tcaggtggat     60

aacaacacga acgcgaccca gctattcaaa aataatataa acaaaaccag aatgaacgat    120

ttaaaccgcg aggagacgcg attaaagacc ttcaccgact ggccgctaga ttggctggat    180

aaacgccaat tggcccaaac cggcatgtac ttcacacacg ccggcgacaa agttaaatgc    240

tttttctgcg gcgtggaaat cggttgctgg gagcaggagg atcagcccgt gccggaacat    300

cagcgatggt cgcccaactg tccactgttg cgccggcgca ctaccaacaa tgtgccgatc    360

aatgccgaag cattagatcg catcctgccg ccaataagct acgatatctg cggcgccaac    420

gactcgacgc tagagatgag ggagcacgcc tacgcagaag gcgtcatacc catgtcgcag    480

ctaattcagt cgattggcat gaatgcagta aatgcggcag gcagtgtaac tggaaccgca    540

gccccgcagc cgagggtaac ggtcgccacc catgcctcga cggcgacaca ggccactggc    600

gatgtccagc cggagacgtg tcgtccttca gccgccagtg gcaattattt tccccagtat    660

cccgaatacg ccatcgagac ggcacgcctg cgcaccttcg aggcttggcc gaggaacctg    720

aaacagaagc cccaccagct ggccgaggcg ggtttcttct atacaggcgt tggggatcgc    780

gtccgctgct tcagttgcgg cggtggtctc atggattgga acgacaacga cgagccctgg    840

gaacagcacg ctctctggct aagtcagtgc cgattcgtca agctgatgaa gggtcagctc    900

tatatcgata cggtggccgc caaaccagtg ctggccgagg agaaggagga gagcacttcg    960

attggagggg acacggtggc cagcacacag gcttcagagg aagagcatca tcggaggagg   1020

ccgtttcggg ggatgtggct ccgtccgtag ctcccacggc agccacacgc atcttcaaca   1080
```

-continued agatcgtcga ggcgacagcg gtggctactc cctcgacaaa cagcagcggc tccacctcca 1140
tacccgagga aaagttgtgc aagatctgct acggcgccga gtacaatacg gcattcctgc 1200
catgcggtca tgtggtggcc tgcgccaagt gcgcctcctc tgtgacaaag tgtccgctgt 1260
gccggaagcc cttcaccgat gtgatgcgcg tatatttttc ttaa 1304

<210> SEQ ID NO 9
<211> LENGTH: 1317
<212> TYPE: DNA
<213> ORGANISM: Drosophila melanogaster

<400> SEQUENCE: 9
atggcatctg ttgtagctga tcttccgtct tatggaccta tcgcttttga tcaggtggat 60
aacaacacga acgcgaccca gctattcaaa aataatataa acaaaaccag aatgaacgat 120
ttaaaccgcg aggagacgcg attaaagacc ttcaccgact ggccgctaga ttggctggat 180
aaacgccaat tggcccaaac cggcatgtac ttcacacacg ccggcgacaa agttaaatgc 240
tttttctgcg gcgtggaaat cggttgctgg gagcaggagg atcagcccgt gccggaacat 300
cagcgatggt cgtccaactg tccactgttg cgccggcgca ctaccaacaa tgtgccgatc 360
aatgccgaag cattagatcg catcctgccg ccaataagct acgatatctg cggcgccaac 420
gactcgacgc tagagatgag ggagcacgcc tacgcagaag gcgtcatacc catgtcgcag 480
ctaattcagt cgattggcat gaatgcagta aatgcggcag gcagtgtaac tggaaccgca 540
gccccgcagc cgagggtaac ggtcgccacc catgcctcga cggcgacaca ggccactggc 600
gatgtccagc cggagacgtg tcgtccttca gccgccagtg gcaattattt tccccagtat 660
cccgaatacg ccatcgagac ggcacgcctg cgcaccttcg aggcttggcc gaggaacctg 720
aaacagaagc cccaccagct ggccgaggcg ggtttcttct atacaggcgt tggggatcgc 780
gtccgctgct tcagttgcgg cggtggtctc atggattgga acgacaacga cgagccctgg 840
gaacagcacg ctctctggct aagtcagtgc cgattcgtca agctgatgaa gggtcagctc 900
tatatcgata cggtggccgc caaaccagtg ctggccgagg agaaggagga gagcacttcg 960
attggagggg acacggtggc cagcacacag gcttcagagg aagagcagca gacatcactc 1020
tcatcggagg aggccgtttc gggggatgtg gctccgtccg tagctcccac ggcagccaca 1080
cgcatcttca acaagatcgt cgaggcgaca gcggtggcta ctccctcgac aaacagcagc 1140
ggctccacct ccatacccga ggaaaagttg tgcaagatct gctacggcgc cgagtacaat 1200
acggcattcc tgccatgcgg tcatgtggtg gcctgcgcca agtgcgcctc ctctgtgaca 1260
aagtgtccgc tgtgccggaa gcccttcacc gatgtgatgc gcgtatattt ttcttaa 1317

<210> SEQ ID NO 10
<211> LENGTH: 1317
<212> TYPE: DNA
<213> ORGANISM: Drosophila melanogaster

<400> SEQUENCE: 10
atggcatctg ttgtagctga tcttccgtct tatggaccta tcgcttttga tcaggtggat 60
aacaacacga acgcgaccca gctattcaaa aataatataa acaaaaccag aatgaacgat 120
ttaaaccgcg aggagacgcg attaaagacc ttcaccgact ggccgctaga ttggctggat 180
aaacgccaat tggcccaaac cggcatgtac ttcacacacg ccggcgacaa agttaaatgc 240
tttttctgcg gcgtggaaat cggttgctgg gagcaggagg atcagcccgt gccggaacat 300
cagcgatggt cgcccaactg tccactgttg cgccggcgca ctaccaacaa tgtgccgatc 360

-continued

```
aatgccgaag cattagatcg catcctgccg ccaataagct acgatatctg cggcgccaac    420

gactcgacgc tagagatgag ggagcacgcc tacgcagaag gcgtcatacc catgtcgcag    480

ctaattcagt cgattggcat gaatgcagta aatgcggcag gcagtgtaac tggaaccgca    540

gccccgcagc cgagggtaac ggtcgccacc catgcctcga cggcgacaca ggccactggc    600

gatgtccagc cggagacgtg tcgtccttca gccgccagtg gcaattattt tccccagtat    660

cccgaatacg ccatcgagac ggcacgcctg cgcaccttcg aggcttggcc gaggaacctg    720

aaacagaagc cccaccagct ggccgaggcg ggtttcttct atacaggcgt tggggatcgc    780

gtccgctgct tcagttgcgg cggtggtctc atggattgga acgacaacga cgagccctgg    840

gaacagcacg ctctctggct aagtcagtgc cgattcgtca agctgatgaa gggtcagctc    900

tatatcgata cggtggccgc caaaccagtg ctggccgagg agaaggagga gagcacttcg    960

attggagggg acacggtggc cagcacacag gcttcagagg aagagcagca gacatcactc   1020

tcatcggagg aggccgtttc gggggatgtg gctccgtccg tagctcccac ggcagccaca   1080

cgcatcttca acaagatcgt cgaggcgaca gcggtggcta ctccctcgac aaacagcagc   1140

ggctccacct ccatacccga ggaaaagttg tgcaagatct gctacggcgc cgagtacaat   1200

acggcattcc tgccatgcgg tcatgtggtg gcctgcgcca agtgcgcctc ctctgtgaca   1260

aagtgtctgc tgtgccggaa gcccttcacc gatgtgatgc gcgtatattt ttcttaa      1317


<210> SEQ ID NO 11
<211> LENGTH: 438
<212> TYPE: PRT
<213> ORGANISM: Drosophila melanogaster

<400> SEQUENCE: 11

Met Ala Ser Val Val Ala Asp Leu Pro Ser Tyr Gly Pro Ile Ala Phe
1               5                   10                  15

Asp Gln Val Asp Asn Asn Thr Asn Ala Thr Gln Leu Phe Lys Asn Asn
            20                  25                  30

Ile Asn Lys Thr Arg Met Asn Asp Leu Asn Arg Glu Glu Thr Arg Leu
        35                  40                  45

Lys Thr Phe Thr Asp Trp Pro Leu Asp Trp Leu Asp Lys Arg Gln Leu
    50                  55                  60

Ala Gln Thr Gly Met Tyr Phe Thr His Ala Gly Asp Lys Val Lys Cys
65                  70                  75                  80

Phe Phe Cys Gly Val Glu Ile Gly Cys Trp Glu Gln Glu Asp Gln Pro
                85                  90                  95

Val Pro Glu His Gln Arg Trp Ser Pro Asn Cys Pro Leu Leu Arg Arg
            100                 105                 110

Arg Thr Thr Asn Asn Val Pro Ile Asn Ala Glu Ala Leu Asp Arg Ile
        115                 120                 125

Leu Pro Pro Ile Ser Tyr Asp Ile Cys Gly Ala Asn Asp Ser Thr Leu
    130                 135                 140

Glu Met Arg Glu His Ala Tyr Ala Glu Gly Val Ile Pro Met Ser Gln
145                 150                 155                 160

Leu Ile Gln Ser Ile Gly Met Asn Ala Val Asn Ala Ala Gly Ser Val
                165                 170                 175

Thr Gly Thr Ala Ala Pro Gln Pro Arg Val Thr Val Ala Thr His Ala
            180                 185                 190

Ser Thr Ala Thr Gln Ala Thr Gly Asp Val Gln Pro Glu Thr Cys Arg
        195                 200                 205
```

-continued

Pro Ser Ala Ala Ser Gly Asn Tyr Phe Pro Gln Tyr Pro Glu Tyr Ala
    210                 215                 220

Ile Glu Thr Ala Arg Leu Arg Thr Phe Glu Ala Trp Pro Arg Asn Leu
225                 230                 235                 240

Lys Gln Lys Pro His Gln Leu Ala Glu Ala Gly Phe Phe Tyr Thr Gly
                245                 250                 255

Val Gly Asp Arg Val Arg Cys Phe Ser Cys Gly Gly Gly Leu Met Asp
            260                 265                 270

Trp Asn Asp Asn Asp Glu Pro Trp Glu Gln His Ala Leu Trp Leu Ser
        275                 280                 285

Gln Cys Arg Phe Val Lys Leu Met Lys Gly Gln Leu Tyr Ile Asp Thr
    290                 295                 300

Val Ala Ala Lys Pro Val Leu Ala Glu Glu Lys Glu Glu Ser Thr Ser
305                 310                 315                 320

Ile Gly Gly Asp Thr Val Ala Ser Thr Gln Ala Ser Glu Glu Glu Gln
                325                 330                 335

Gln Thr Ser Leu Ser Ser Glu Glu Ala Val Ser Gly Asp Val Ala Pro
            340                 345                 350

Ser Val Ala Pro Thr Ala Ala Thr Arg Ile Phe Asn Lys Ile Val Glu
        355                 360                 365

Ala Thr Ala Val Ala Thr Pro Ser Thr Asn Ser Ser Gly Ser Thr Ser
    370                 375                 380

Ile Pro Glu Glu Lys Leu Cys Lys Ile Cys Tyr Gly Ala Glu Tyr Asn
385                 390                 395                 400

Thr Ala Phe Leu Pro Cys Gly His Val Val Ala Cys Ala Lys Cys Ala
                405                 410                 415

Ser Ser Val Thr Lys Cys Pro Leu Cys Arg Lys Pro Phe Thr Asp Val
            420                 425                 430

Met Arg Val Tyr Phe Ser
        435

<210> SEQ ID NO 12
<211> LENGTH: 438
<212> TYPE: PRT
<213> ORGANISM: Drosophila melanogaster

<400> SEQUENCE: 12

Met Ala Ser Val Val Ala Asp Leu Pro Ser Tyr Gly Pro Ile Ala Phe
1               5                   10                  15

Asp Gln Val Asp Asn Asn Thr Asn Ala Thr Gln Leu Phe Lys Asn Asn
            20                  25                  30

Ile Asn Lys Thr Arg Met Asn Asp Leu Asn Arg Glu Glu Thr Arg Leu
        35                  40                  45

Lys Thr Phe Thr Asp Trp Pro Leu Asp Trp Leu Asp Lys Arg Gln Leu
    50                  55                  60

Ala Gln Thr Gly Met Tyr Phe Thr His Ala Gly Asp Lys Val Lys Cys
65                  70                  75                  80

Phe Phe Cys Gly Val Glu Ile Ser Cys Trp Glu Gln Glu Asp Gln Pro
                85                  90                  95

Val Pro Glu His Gln Arg Trp Ser Pro Asn Cys Pro Leu Leu Arg Arg
            100                 105                 110

Arg Thr Thr Asn Asn Val Pro Ile Asn Ala Glu Ala Leu Asp Arg Ile
        115                 120                 125

Leu Pro Pro Ile Ser Tyr Asp Ile Cys Gly Ala Asn Asp Ser Thr Leu

-continued

```
    130                 135                 140

Glu Met Arg Glu His Ala Tyr Ala Glu Gly Val Ile Pro Met Ser Gln
145                 150                 155                 160

Leu Ile Gln Ser Ile Gly Met Asn Ala Val Asn Ala Ala Gly Ser Val
                165                 170                 175

Thr Gly Thr Ala Ala Pro Gln Pro Arg Val Thr Val Ala Thr His Ala
            180                 185                 190

Ser Thr Ala Thr Gln Ala Thr Gly Asp Val Gln Pro Glu Thr Cys Arg
        195                 200                 205

Pro Ser Ala Ala Ser Gly Asn Tyr Phe Pro Gln Tyr Pro Glu Tyr Ala
    210                 215                 220

Ile Glu Thr Ala Arg Leu Arg Thr Phe Glu Ala Trp Pro Arg Asn Leu
225                 230                 235                 240

Lys Gln Lys Pro His Gln Leu Ala Glu Ala Gly Phe Phe Tyr Thr Gly
                245                 250                 255

Val Gly Asp Arg Val Arg Cys Phe Ser Cys Gly Gly Gly Leu Met Asp
            260                 265                 270

Trp Asn Asp Asn Asp Glu Pro Trp Glu Gln His Ala Leu Trp Leu Ser
        275                 280                 285

Gln Cys Arg Phe Val Lys Leu Met Lys Gly Gln Leu Tyr Ile Asp Thr
    290                 295                 300

Val Ala Ala Lys Pro Val Leu Ala Glu Glu Lys Glu Glu Ser Thr Ser
305                 310                 315                 320

Ile Gly Gly Asp Thr Val Ala Ser Thr Gln Ala Ser Glu Glu Glu Gln
                325                 330                 335

Gln Thr Ser Leu Ser Ser Glu Glu Ala Val Ser Gly Asp Val Ala Pro
            340                 345                 350

Ser Val Ala Pro Thr Ala Ala Thr Arg Ile Phe Asn Lys Ile Val Glu
        355                 360                 365

Ala Thr Ala Val Ala Thr Pro Ser Thr Asn Ser Ser Gly Ser Thr Ser
    370                 375                 380

Ile Pro Glu Glu Lys Leu Cys Lys Ile Cys Tyr Gly Ala Glu Tyr Asn
385                 390                 395                 400

Thr Ala Phe Leu Pro Cys Gly His Val Val Ala Cys Ala Lys Cys Ala
                405                 410                 415

Ser Ser Val Thr Lys Cys Pro Leu Cys Arg Lys Pro Phe Thr Asp Val
            420                 425                 430

Met Arg Val Tyr Phe Ser
        435


<210> SEQ ID NO 13
<211> LENGTH: 438
<212> TYPE: PRT
<213> ORGANISM: Drosophila melanogaster

<400> SEQUENCE: 13

Met Ala Ser Val Val Ala Asp Leu Pro Ser Tyr Gly Pro Ile Ala Phe
1               5                   10                  15

Asp Gln Val Asp Asn Asn Thr Asn Ala Thr Gln Leu Phe Lys Asn Asn
            20                  25                  30

Ile Asn Lys Thr Arg Met Asn Asp Leu Asn Arg Glu Glu Thr Arg Leu
        35                  40                  45

Lys Thr Phe Thr Asp Trp Pro Leu Asp Trp Leu Asp Lys Arg Gln Leu
    50                  55                  60
```

-continued

```
Ala Gln Thr Gly Met Tyr Phe Thr His Ala Gly Asp Lys Val Lys Cys
65                  70                  75                  80

Phe Phe Cys Gly Val Glu Ile Asp Cys Trp Glu Gln Glu Asp Gln Pro
                85                  90                  95

Val Pro Glu His Gln Arg Trp Ser Pro Asn Cys Pro Leu Leu Arg Arg
            100                 105                 110

Arg Thr Thr Asn Asn Val Pro Ile Asn Ala Glu Ala Leu Asp Arg Ile
        115                 120                 125

Leu Pro Pro Ile Ser Tyr Asp Ile Cys Gly Ala Asn Asp Ser Thr Leu
    130                 135                 140

Glu Met Arg Glu His Ala Tyr Ala Glu Gly Val Ile Pro Met Ser Gln
145                 150                 155                 160

Leu Ile Gln Ser Ile Gly Met Asn Ala Val Asn Ala Ala Gly Ser Val
                165                 170                 175

Thr Gly Thr Ala Ala Pro Gln Pro Arg Val Thr Val Ala Thr His Ala
            180                 185                 190

Ser Thr Ala Thr Gln Ala Thr Gly Asp Val Gln Pro Glu Thr Cys Arg
        195                 200                 205

Pro Ser Ala Ala Ser Gly Asn Tyr Phe Pro Gln Tyr Pro Glu Tyr Ala
    210                 215                 220

Ile Glu Thr Ala Arg Leu Arg Thr Phe Glu Ala Trp Pro Arg Asn Leu
225                 230                 235                 240

Lys Gln Lys Pro His Gln Leu Ala Glu Ala Gly Phe Phe Tyr Thr Gly
                245                 250                 255

Val Gly Asp Arg Val Arg Cys Phe Ser Cys Gly Gly Gly Leu Met Asp
            260                 265                 270

Trp Asn Asp Asn Asp Glu Pro Trp Glu Gln His Ala Leu Trp Leu Ser
        275                 280                 285

Gln Cys Arg Phe Val Lys Leu Met Lys Gly Gln Leu Tyr Ile Asp Thr
    290                 295                 300

Val Ala Ala Lys Pro Val Leu Ala Glu Glu Lys Glu Glu Ser Thr Ser
305                 310                 315                 320

Ile Gly Gly Asp Thr Val Ala Ser Thr Gln Ala Ser Glu Glu Glu Gln
                325                 330                 335

Gln Thr Ser Leu Ser Ser Glu Glu Ala Val Ser Gly Asp Val Ala Pro
            340                 345                 350

Ser Val Ala Pro Thr Ala Ala Thr Arg Ile Phe Asn Lys Ile Val Glu
        355                 360                 365

Ala Thr Ala Val Ala Thr Pro Ser Thr Asn Ser Ser Gly Ser Thr Ser
    370                 375                 380

Ile Pro Glu Glu Lys Leu Cys Lys Ile Cys Tyr Gly Ala Glu Tyr Asn
385                 390                 395                 400

Thr Ala Phe Leu Pro Cys Gly His Val Val Ala Cys Ala Lys Cys Ala
                405                 410                 415

Ser Ser Val Thr Lys Cys Pro Leu Cys Arg Lys Pro Phe Thr Asp Val
            420                 425                 430

Met Arg Val Tyr Phe Ser
        435
```

<210> SEQ ID NO 14
<211> LENGTH: 438
<212> TYPE: PRT
<213> ORGANISM: Drosophila melanogaster

<400> SEQUENCE: 14

-continued

```
Met Ala Ser Val Val Ala Asp Leu Pro Ser Tyr Gly Pro Ile Ala Phe
1               5                   10                  15

Asp Gln Val Asp Asn Asn Thr Asn Ala Thr Gln Leu Phe Lys Asn Asn
            20                  25                  30

Ile Asn Lys Thr Arg Met Asn Asp Leu Asn Arg Glu Glu Thr Arg Leu
        35                  40                  45

Lys Thr Phe Thr Asp Trp Pro Leu Asp Trp Leu Asp Lys Arg Gln Leu
    50                  55                  60

Ala Gln Thr Gly Met Tyr Phe Thr His Ala Gly Asp Lys Val Lys Cys
65                  70                  75                  80

Phe Phe Cys Gly Val Glu Ile Gly Cys Trp Glu Gln Glu Asp Gln Pro
                85                  90                  95

Val Pro Glu His Gln Arg Trp Ser Pro Asn Cys Pro Leu Leu Arg Arg
            100                 105                 110

Arg Thr Thr Asn Asn Val Pro Ile Asn Ala Glu Ala Leu Asp Arg Ile
        115                 120                 125

Leu Pro Pro Ile Ser Tyr Asp Ile Cys Gly Ala Asn Asp Ser Thr Leu
    130                 135                 140

Glu Met Arg Glu His Ala Tyr Ala Glu Gly Val Ile Pro Met Ser Gln
145                 150                 155                 160

Leu Ile Gln Ser Ile Gly Met Asn Ala Val Asn Ala Ala Gly Ser Val
                165                 170                 175

Thr Gly Thr Ala Ala Pro Gln Pro Arg Val Thr Val Ala Thr His Ala
            180                 185                 190

Ser Thr Ala Thr Gln Ala Thr Gly Asp Val Gln Pro Glu Thr Cys Arg
        195                 200                 205

Pro Ser Ala Ala Ser Gly Asn Tyr Phe Pro Gln Tyr Pro Glu Tyr Ala
    210                 215                 220

Ile Glu Thr Ala Arg Leu Arg Thr Phe Glu Ala Trp Pro Arg Asn Leu
225                 230                 235                 240

Lys Gln Lys Pro His Gln Leu Ala Glu Ala Gly Phe Phe Tyr Thr Gly
                245                 250                 255

Val Gly Asp Arg Val Arg Cys Phe Ser Cys Gly Gly Ser Leu Met Asp
            260                 265                 270

Trp Asn Asp Asn Asp Glu Pro Trp Glu Gln His Ala Leu Trp Leu Ser
        275                 280                 285

Gln Cys Arg Phe Val Lys Leu Met Lys Gly Gln Leu Tyr Ile Asp Thr
    290                 295                 300

Val Ala Ala Lys Pro Val Leu Ala Glu Glu Lys Glu Glu Ser Thr Ser
305                 310                 315                 320

Ile Gly Gly Asp Thr Val Ala Ser Thr Gln Ala Ser Glu Glu Glu Gln
                325                 330                 335

Gln Thr Ser Leu Ser Ser Glu Glu Ala Val Ser Gly Asp Val Ala Pro
            340                 345                 350

Ser Val Ala Pro Thr Ala Ala Thr Arg Ile Phe Asn Lys Ile Val Glu
        355                 360                 365

Ala Thr Ala Val Ala Thr Pro Ser Thr Asn Ser Ser Gly Ser Thr Ser
    370                 375                 380

Ile Pro Glu Glu Lys Leu Cys Lys Ile Cys Tyr Gly Ala Glu Tyr Asn
385                 390                 395                 400

Thr Ala Phe Leu Pro Cys Gly His Val Val Ala Cys Ala Lys Cys Ala
                405                 410                 415
```

-continued

```
Ser Ser Val Thr Lys Cys Pro Leu Cys Arg Lys Pro Phe Thr Asp Val
            420                 425                 430

Met Arg Val Tyr Phe Ser
        435


<210> SEQ ID NO 15
<211> LENGTH: 438
<212> TYPE: PRT
<213> ORGANISM: Drosophila melanogaster

<400> SEQUENCE: 15

Met Ala Ser Val Val Ala Asp Leu Pro Ser Tyr Gly Pro Ile Ala Phe
1               5                   10                  15

Asp Gln Val Asp Asn Asn Thr Asn Ala Thr Gln Leu Phe Lys Asn Asn
            20                  25                  30

Ile Asn Lys Thr Arg Met Asn Asp Leu Asn Arg Glu Glu Thr Arg Leu
        35                  40                  45

Lys Thr Phe Thr Asp Trp Pro Leu Asp Trp Leu Asp Lys Arg Gln Leu
    50                  55                  60

Ala Gln Thr Gly Met Tyr Phe Thr His Ala Gly Asp Lys Val Lys Cys
65                  70                  75                  80

Phe Phe Cys Gly Val Glu Ile Gly Cys Trp Glu Gln Glu Asp Gln Pro
                85                  90                  95

Val Pro Glu His Gln Arg Trp Ser Pro Asn Cys Pro Leu Leu Arg Arg
            100                 105                 110

Arg Thr Thr Asn Lys Val Pro Ile Asn Ala Glu Ala Leu Asp Arg Ile
        115                 120                 125

Leu Pro Pro Ile Ser Tyr Asp Ile Cys Gly Ala Asn Asp Ser Thr Leu
    130                 135                 140

Glu Met Arg Glu His Ala Tyr Ala Glu Gly Val Ile Pro Met Ser Gln
145                 150                 155                 160

Leu Ile Gln Ser Ile Gly Met Asn Ala Val Asn Ala Ala Gly Ser Val
                165                 170                 175

Thr Gly Thr Ala Ala Pro Gln Pro Arg Val Thr Val Ala Thr His Ala
            180                 185                 190

Ser Thr Ala Thr Gln Ala Thr Gly Asp Val Gln Pro Glu Thr Cys Arg
        195                 200                 205

Pro Ser Ala Ala Ser Gly Asn Tyr Phe Pro Gln Tyr Pro Glu Tyr Ala
    210                 215                 220

Ile Glu Thr Ala Arg Leu Arg Thr Phe Glu Ala Trp Pro Arg Asn Leu
225                 230                 235                 240

Lys Gln Lys Pro His Gln Leu Ala Glu Ala Gly Phe Phe Tyr Thr Gly
                245                 250                 255

Val Gly Asp Arg Val Arg Cys Phe Ser Cys Gly Gly Gly Leu Met Asp
            260                 265                 270

Trp Asn Asp Asn Asp Glu Pro Trp Glu Gln His Ala Leu Trp Leu Ser
        275                 280                 285

Gln Cys Arg Phe Val Lys Leu Met Lys Gly Gln Leu Tyr Ile Asp Thr
    290                 295                 300

Val Ala Ala Lys Pro Val Leu Ala Glu Glu Lys Glu Glu Ser Thr Ser
305                 310                 315                 320

Ile Gly Gly Asp Thr Val Ala Ser Thr Gln Ala Ser Glu Glu Glu Gln
                325                 330                 335

Gln Thr Ser Leu Ser Ser Glu Glu Ala Val Ser Gly Asp Val Ala Pro
            340                 345                 350
```

-continued

```
Ser Val Ala Pro Thr Ala Ala Thr Arg Ile Phe Asn Lys Ile Val Glu
        355                 360                 365

Ala Thr Ala Val Ala Thr Pro Ser Thr Asn Ser Ser Gly Ser Thr Ser
    370                 375                 380

Ile Pro Glu Glu Lys Leu Cys Lys Ile Cys Tyr Gly Ala Glu Tyr Asn
385                 390                 395                 400

Thr Ala Phe Leu Pro Cys Gly His Val Val Ala Cys Ala Lys Cys Ala
                405                 410                 415

Ser Ser Val Thr Lys Cys Pro Leu Cys Arg Lys Pro Phe Thr Asp Val
            420                 425                 430

Met Arg Val Tyr Phe Ser
        435


<210> SEQ ID NO 16
<211> LENGTH: 438
<212> TYPE: PRT
<213> ORGANISM: Drosophila melanogaster

<400> SEQUENCE: 16

Met Ala Ser Val Val Ala Asp Leu Pro Ser Tyr Gly Pro Ile Ala Phe
1               5                   10                  15

Asp Gln Val Asp Asn Asn Thr Asn Ala Thr Gln Leu Phe Lys Asn Asn
            20                  25                  30

Ile Asn Lys Thr Arg Met Asn Asp Leu Asn Arg Glu Glu Thr Arg Leu
        35                  40                  45

Lys Thr Phe Thr Asp Trp Pro Leu Asp Trp Leu Asp Lys Arg Gln Leu
    50                  55                  60

Ala Gln Thr Gly Met Tyr Phe Thr His Ala Gly Asp Lys Val Lys Cys
65                  70                  75                  80

Phe Phe Cys Gly Val Glu Ile Gly Cys Trp Glu Gln Glu Asp Gln Pro
                85                  90                  95

Val Pro Glu His Gln Arg Trp Ser Pro Asn Cys Pro Leu Leu Arg Arg
            100                 105                 110

Arg Thr Thr Asn Asn Val Pro Ile Asn Ala Glu Ala Leu Asp Arg Ile
        115                 120                 125

Leu Pro Pro Ile Ser Tyr Asp Ile Cys Gly Ala Asn Asp Ser Thr Leu
    130                 135                 140

Glu Met Arg Glu His Ala Tyr Ala Glu Gly Val Ile Pro Met Ser Gln
145                 150                 155                 160

Leu Ile Gln Ser Ile Gly Met Asn Ala Val Asn Ala Ala Gly Ser Val
                165                 170                 175

Thr Gly Thr Ala Ala Pro Gln Pro Arg Val Thr Val Ala Thr His Ala
            180                 185                 190

Ser Thr Ala Thr Gln Ala Thr Gly Asp Val Gln Pro Glu Thr Cys Arg
        195                 200                 205

Pro Ser Ala Ala Ser Gly Asn Tyr Phe Pro Gln Tyr Pro Glu Tyr Ala
    210                 215                 220

Ile Glu Thr Ala Arg Leu Arg Thr Phe Glu Ala Trp Pro Arg Asn Leu
225                 230                 235                 240

Lys Gln Lys Pro His Gln Leu Ala Glu Ala Gly Phe Phe Tyr Thr Gly
                245                 250                 255

Val Gly Asp Arg Val Arg Cys Phe Ser Cys Gly Gly Gly Leu Met Asp
            260                 265                 270

Trp Asn Asp Asn Asp Glu Pro Trp Glu Gln His Ala Leu Trp Leu Ser
```

-continued

```
        275                 280                 285

Gln Cys Arg Phe Val Lys Leu Met Lys Gly Gln Leu Tyr Ile Asp Thr
    290                 295                 300

Val Ala Ala Lys Pro Val Leu Ala Glu Glu Lys Glu Glu Ser Thr Ser
305                 310                 315                 320

Ile Gly Gly Asp Thr Val Ala Ser Thr Gln Ala Ser Glu Glu Glu Gln
                325                 330                 335

Gln Thr Ser Leu Ser Ser Glu Glu Ala Val Ser Gly Asp Val Ala Pro
            340                 345                 350

Ser Val Ala Pro Thr Ala Ala Thr Arg Ile Phe Asn Lys Ile Val Glu
        355                 360                 365

Ala Thr Ala Val Ala Thr Pro Ser Thr Asn Ser Ser Gly Ser Thr Ser
    370                 375                 380

Ile Pro Glu Glu Lys Leu Cys Lys Ile Cys Tyr Gly Ala Glu Tyr Asn
385                 390                 395                 400

Thr Ala Phe Leu Pro Cys Gly His Val Val Ala Cys Ala Lys Tyr Ala
                405                 410                 415

Ser Ser Val Thr Lys Cys Pro Leu Cys Arg Lys Pro Phe Thr Asp Val
            420                 425                 430

Met Arg Val Tyr Phe Ser
        435


<210> SEQ ID NO 17
<211> LENGTH: 438
<212> TYPE: PRT
<213> ORGANISM: Drosophila melanogaster

<400> SEQUENCE: 17

Met Ala Ser Val Val Ala Asp Leu Pro Ser Tyr Gly Pro Ile Ala Phe
1               5                   10                  15

Asp Gln Val Asp Asn Asn Thr Asn Ala Thr Gln Leu Phe Lys Asn Asn
            20                  25                  30

Ile Asn Lys Thr Arg Met Asn Asp Leu Asn Arg Glu Glu Thr Arg Leu
        35                  40                  45

Lys Thr Phe Thr Asp Trp Pro Leu Asp Trp Leu Asp Lys Arg Gln Leu
    50                  55                  60

Ala Gln Thr Gly Met Tyr Phe Thr His Ala Gly Asp Lys Val Lys Cys
65                  70                  75                  80

Phe Phe Cys Gly Val Glu Ile Gly Cys Trp Glu Gln Glu Asp Gln Pro
                85                  90                  95

Val Pro Glu His Gln Arg Trp Ser Pro Asn Cys Pro Leu Leu Arg Arg
            100                 105                 110

Arg Thr Thr Asn Asn Val Pro Ile Asn Ala Glu Ala Leu Asp Arg Ile
        115                 120                 125

Leu Pro Pro Ile Ser Tyr Asp Ile Cys Gly Ala Asn Asp Ser Thr Leu
    130                 135                 140

Glu Met Arg Glu His Ala Tyr Ala Glu Gly Val Ile Pro Met Ser Gln
145                 150                 155                 160

Leu Ile Gln Ser Ile Gly Met Asn Ala Val Asn Ala Ala Gly Ser Val
                165                 170                 175

Thr Gly Thr Ala Ala Pro Gln Pro Arg Val Thr Val Ala Thr His Ala
            180                 185                 190

Ser Thr Ala Thr Gln Ala Thr Gly Asp Val Gln Pro Glu Thr Cys Arg
        195                 200                 205
```

-continued

Pro Ser Ala Ala Ser Gly Asn Tyr Phe Pro Gln Tyr Pro Glu Tyr Ala
    210                 215                 220

Ile Glu Thr Ala Arg Leu Arg Thr Phe Glu Ala Trp Pro Arg Asn Leu
225                 230                 235                 240

Lys Gln Lys Pro His Gln Leu Ala Glu Ala Gly Phe Phe Tyr Thr Gly
                245                 250                 255

Val Gly Asp Arg Val Arg Cys Phe Ser Cys Gly Gly Gly Leu Met Asp
            260                 265                 270

Trp Asn Asp Asn Asp Glu Pro Trp Glu Gln His Ala Leu Trp Leu Ser
        275                 280                 285

Gln Cys Arg Phe Val Lys Leu Met Lys Gly Gln Leu Tyr Ile Asp Thr
    290                 295                 300

Val Ala Ala Lys Pro Val Leu Ala Glu Glu Lys Glu Glu Ser Thr Ser
305                 310                 315                 320

Ile Gly Gly Asp Thr Val Ala Ser Thr Gln Ala Ser Glu Glu Glu Gln
                325                 330                 335

Gln Thr Ser Leu Ser Ser Glu Glu Ala Val Ser Gly Asp Val Ala Pro
            340                 345                 350

Ser Val Ala Pro Thr Ala Ala Thr Arg Ile Phe Asn Lys Ile Val Glu
        355                 360                 365

Ala Thr Ala Val Ala Thr Pro Ser Thr Asn Ser Ser Gly Ser Thr Ser
    370                 375                 380

Ile Pro Glu Glu Lys Leu Cys Lys Ile Cys Tyr Gly Ala Glu Tyr Asn
385                 390                 395                 400

Thr Ala Phe Leu Pro Tyr Gly His Val Val Ala Cys Ala Lys Cys Ala
                405                 410                 415

Ser Ser Val Thr Lys Cys Pro Leu Cys Arg Lys Pro Phe Thr Asp Val
            420                 425                 430

Met Arg Val Tyr Phe Ser
        435

<210> SEQ ID NO 18
<211> LENGTH: 431
<212> TYPE: PRT
<213> ORGANISM: Drosophila melanogaster

<400> SEQUENCE: 18

Met Ala Ser Val Val Ala Asp Leu Pro Ser Tyr Gly Pro Ile Ala Phe
1               5                   10                  15

Asp Gln Val Asp Asn Asn Thr Asn Ala Thr Gln Leu Phe Lys Asn Asn
            20                  25                  30

Ile Asn Lys Thr Arg Met Asn Asp Leu Asn Arg Glu Glu Thr Arg Leu
        35                  40                  45

Lys Thr Phe Thr Asp Trp Pro Leu Asp Trp Leu Asp Lys Arg Gln Leu
    50                  55                  60

Ala Gln Thr Gly Met Tyr Phe Thr His Ala Gly Asp Lys Val Lys Cys
65                  70                  75                  80

Phe Phe Cys Gly Val Glu Ile Gly Cys Trp Glu Gln Glu Asp Gln Pro
                85                  90                  95

Val Pro Glu His Gln Arg Trp Ser Pro Asn Cys Pro Leu Leu Arg Arg
            100                 105                 110

Arg Thr Thr Asn Asn Val Pro Ile Asn Ala Glu Ala Leu Asp Arg Ile
        115                 120                 125

Leu Pro Pro Ile Ser Tyr Asp Ile Cys Gly Ala Asn Asp Ser Thr Leu
    130                 135                 140

-continued

Glu Met Arg Glu His Ala Tyr Ala Glu Gly Val Ile Pro Met Ser Gln
145 150 155 160

Leu Ile Gln Ser Ile Gly Met Asn Ala Val Asn Ala Ala Gly Ser Val
165 170 175

Thr Gly Thr Ala Ala Pro Gln Pro Arg Val Thr Val Ala Thr His Ala
180 185 190

Ser Thr Ala Thr Gln Ala Thr Gly Asp Val Gln Pro Glu Thr Cys Arg
195 200 205

Pro Ser Ala Ala Ser Gly Asn Tyr Phe Pro Gln Tyr Pro Glu Tyr Ala
210 215 220

Ile Glu Thr Ala Arg Leu Arg Thr Phe Glu Ala Trp Pro Arg Asn Leu
225 230 235 240

Lys Gln Lys Pro His Gln Leu Ala Glu Ala Gly Phe Phe Tyr Thr Gly
245 250 255

Val Gly Asp Arg Val Arg Cys Phe Ser Cys Gly Gly Gly Leu Met Asp
260 265 270

Trp Asn Asp Asn Asp Glu Pro Trp Glu Gln His Ala Leu Trp Leu Ser
275 280 285

Gln Cys Arg Phe Val Lys Leu Met Lys Gly Gln Leu Tyr Ile Asp Thr
290 295 300

Val Ala Ala Lys Pro Val Leu Ala Glu Glu Lys Glu Glu Ser Thr Ser
305 310 315 320

Ile Gly Gly Asp Thr Val Ala Ser Thr Gln Ala Ser Glu Glu Glu His
325 330 335

His Arg Arg Arg Pro Phe Arg Gly Met Trp Leu Arg Pro Leu Pro Arg
340 345 350

Gln Pro His Ala Ser Ser Thr Arg Ser Ser Arg Arg Gln Arg Trp Leu
355 360 365

Leu Pro Arg Gln Thr Ala Ala Ala Pro Pro Pro Tyr Pro Arg Lys Ser
370 375 380

Cys Ala Arg Ser Ala Thr Ala Pro Ser Thr Ile Arg His Ser Cys His
385 390 395 400

Ala Val Met Trp Trp Pro Ala Pro Ser Ala Pro Pro Leu Gln Ser Val
405 410 415

Arg Cys Ala Gly Ser Pro Ser Pro Met Cys Ala Tyr Ile Phe Leu
420 425 430

<210> SEQ ID NO 19
<211> LENGTH: 438
<212> TYPE: PRT
<213> ORGANISM: Drosophila melanogaster

<400> SEQUENCE: 19

Met Ala Ser Val Val Ala Asp Leu Pro Ser Tyr Gly Pro Ile Ala Phe
1 5 10 15

Asp Gln Val Asp Asn Asn Thr Asn Ala Thr Gln Leu Phe Lys Asn Asn
20 25 30

Ile Asn Lys Thr Arg Met Asn Asp Leu Asn Arg Glu Glu Thr Arg Leu
35 40 45

Lys Thr Phe Thr Asp Trp Pro Leu Asp Trp Leu Asp Lys Arg Gln Leu
50 55 60

Ala Gln Thr Gly Met Tyr Phe Thr His Ala Gly Asp Lys Val Lys Cys
65 70 75 80

Phe Phe Cys Gly Val Glu Ile Gly Cys Trp Glu Gln Glu Asp Gln Pro

-continued

```
                85                  90                  95

Val Pro Glu His Gln Arg Trp Ser Ser Asn Cys Pro Leu Leu Arg Arg
            100                 105                 110

Arg Thr Thr Asn Asn Val Pro Ile Asn Ala Glu Ala Leu Asp Arg Ile
        115                 120                 125

Leu Pro Pro Ile Ser Tyr Asp Ile Cys Gly Ala Asn Asp Ser Thr Leu
    130                 135                 140

Glu Met Arg Glu His Ala Tyr Ala Glu Gly Val Ile Pro Met Ser Gln
145                 150                 155                 160

Leu Ile Gln Ser Ile Gly Met Asn Ala Val Asn Ala Ala Gly Ser Val
                165                 170                 175

Thr Gly Thr Ala Ala Pro Gln Pro Arg Val Thr Val Ala Thr His Ala
            180                 185                 190

Ser Thr Ala Thr Gln Ala Thr Gly Asp Val Gln Pro Glu Thr Cys Arg
        195                 200                 205

Pro Ser Ala Ala Ser Gly Asn Tyr Phe Pro Gln Tyr Pro Glu Tyr Ala
    210                 215                 220

Ile Glu Thr Ala Arg Leu Arg Thr Phe Glu Ala Trp Pro Arg Asn Leu
225                 230                 235                 240

Lys Gln Lys Pro His Gln Leu Ala Glu Ala Gly Phe Phe Tyr Thr Gly
                245                 250                 255

Val Gly Asp Arg Val Arg Cys Phe Ser Cys Gly Gly Gly Leu Met Asp
            260                 265                 270

Trp Asn Asp Asn Asp Glu Pro Trp Glu Gln His Ala Leu Trp Leu Ser
        275                 280                 285

Gln Cys Arg Phe Val Lys Leu Met Lys Gly Gln Leu Tyr Ile Asp Thr
    290                 295                 300

Val Ala Ala Lys Pro Val Leu Ala Glu Glu Lys Glu Glu Ser Thr Ser
305                 310                 315                 320

Ile Gly Gly Asp Thr Val Ala Ser Thr Gln Ala Ser Glu Glu Glu Gln
                325                 330                 335

Gln Thr Ser Leu Ser Ser Glu Glu Ala Val Ser Gly Asp Val Ala Pro
            340                 345                 350

Ser Val Ala Pro Thr Ala Ala Thr Arg Ile Phe Asn Lys Ile Val Glu
        355                 360                 365

Ala Thr Ala Val Ala Thr Pro Ser Thr Asn Ser Ser Gly Ser Thr Ser
    370                 375                 380

Ile Pro Glu Glu Lys Leu Cys Lys Ile Cys Tyr Gly Ala Glu Tyr Asn
385                 390                 395                 400

Thr Ala Phe Leu Pro Cys Gly His Val Val Ala Cys Ala Lys Cys Ala
                405                 410                 415

Ser Ser Val Thr Lys Cys Pro Leu Cys Arg Lys Pro Phe Thr Asp Val
            420                 425                 430

Met Arg Val Tyr Phe Ser
        435


<210> SEQ ID NO 20
<211> LENGTH: 438
<212> TYPE: PRT
<213> ORGANISM: Drosophila melanogaster

<400> SEQUENCE: 20

Met Ala Ser Val Val Ala Asp Leu Pro Ser Tyr Gly Pro Ile Ala Phe
1               5                   10                  15
```

-continued

```
Asp Gln Val Asp Asn Asn Thr Asn Ala Thr Gln Leu Phe Lys Asn Asn
            20                  25                  30

Ile Asn Lys Thr Arg Met Asn Asp Leu Asn Arg Glu Glu Thr Arg Leu
        35                  40                  45

Lys Thr Phe Thr Asp Trp Pro Leu Asp Trp Leu Asp Lys Arg Gln Leu
    50                  55                  60

Ala Gln Thr Gly Met Tyr Phe Thr His Ala Gly Asp Lys Val Lys Cys
65                  70                  75                  80

Phe Phe Cys Gly Val Glu Ile Gly Cys Trp Glu Gln Glu Asp Gln Pro
                85                  90                  95

Val Pro Glu His Gln Arg Trp Ser Pro Asn Cys Pro Leu Leu Arg Arg
            100                 105                 110

Arg Thr Thr Asn Asn Val Pro Ile Asn Ala Glu Ala Leu Asp Arg Ile
        115                 120                 125

Leu Pro Pro Ile Ser Tyr Asp Ile Cys Gly Ala Asn Asp Ser Thr Leu
    130                 135                 140

Glu Met Arg Glu His Ala Tyr Ala Glu Gly Val Ile Pro Met Ser Gln
145                 150                 155                 160

Leu Ile Gln Ser Ile Gly Met Asn Ala Val Asn Ala Ala Gly Ser Val
                165                 170                 175

Thr Gly Thr Ala Ala Pro Gln Pro Arg Val Thr Val Ala Thr His Ala
            180                 185                 190

Ser Thr Ala Thr Gln Ala Thr Gly Asp Val Gln Pro Glu Thr Cys Arg
        195                 200                 205

Pro Ser Ala Ala Ser Gly Asn Tyr Phe Pro Gln Tyr Pro Glu Tyr Ala
    210                 215                 220

Ile Glu Thr Ala Arg Leu Arg Thr Phe Glu Ala Trp Pro Arg Asn Leu
225                 230                 235                 240

Lys Gln Lys Pro His Gln Leu Ala Glu Ala Gly Phe Phe Tyr Thr Gly
                245                 250                 255

Val Gly Asp Arg Val Arg Cys Phe Ser Cys Gly Gly Gly Leu Met Asp
            260                 265                 270

Trp Asn Asp Asn Asp Glu Pro Trp Glu Gln His Ala Leu Trp Leu Ser
        275                 280                 285

Gln Cys Arg Phe Val Lys Leu Met Lys Gly Gln Leu Tyr Ile Asp Thr
    290                 295                 300

Val Ala Ala Lys Pro Val Leu Ala Glu Glu Lys Glu Glu Ser Thr Ser
305                 310                 315                 320

Ile Gly Gly Asp Thr Val Ala Ser Thr Gln Ala Ser Glu Glu Glu Gln
                325                 330                 335

Gln Thr Ser Leu Ser Ser Glu Glu Ala Val Ser Gly Asp Val Ala Pro
            340                 345                 350

Ser Val Ala Pro Thr Ala Ala Thr Arg Ile Phe Asn Lys Ile Val Glu
        355                 360                 365

Ala Thr Ala Val Ala Thr Pro Ser Thr Asn Ser Ser Gly Ser Thr Ser
    370                 375                 380

Ile Pro Glu Glu Lys Leu Cys Lys Ile Cys Tyr Gly Ala Glu Tyr Asn
385                 390                 395                 400

Thr Ala Phe Leu Pro Cys Gly His Val Val Ala Cys Ala Lys Cys Ala
                405                 410                 415
```

-continued

```
Ser Ser Val Thr Lys Cys Leu Leu Cys Arg Lys Pro Phe Thr Asp Val
            420                 425                 430

Met Arg Val Tyr Phe Ser
        435
```